US007700756B2

(12) United States Patent
Bender et al.

(10) Patent No.: US 7,700,756 B2
(45) Date of Patent: Apr. 20, 2010

(54) METABOLIC PRIMERS FOR THE DETECTION OF PERCHLORATE-REDUCING BACTERIA AND METHODS OF USE THEREOF

(75) Inventors: Kelly S. Bender, Pickneyville, IL (US); Laurie Achenbach, Carbondale, IL (US)

(73) Assignee: Southern Illinois University, Carbondale, IL (US)

( * ) Notice: Subject to any disclaimer, the term of this patent is extended or adjusted under 35 U.S.C. 154(b) by 0 days.

(21) Appl. No.: 11/828,994

(22) Filed: Jul. 26, 2007

(65) Prior Publication Data

US 2008/0249295 A1 Oct. 9, 2008

Related U.S. Application Data

(60) Provisional application No. 60/833,825, filed on Jul. 27, 2006.

(51) Int. Cl.
C07H 21/04 (2006.01)
C12Q 1/68 (2006.01)
C12P 19/34 (2006.01)

(52) U.S. Cl. ................. 536/24.33; 435/6; 435/91.1; 435/91.2

(58) Field of Classification Search .................. None
See application file for complete search history.

(56) References Cited

U.S. PATENT DOCUMENTS

| | | | |
|---|---|---|---|
| 4,458,006 | A | 7/1984 | Donges et al. |
| 4,683,195 | A | 7/1987 | Mullis et al. |
| 4,683,202 | A | 7/1987 | Mullis |
| 4,800,159 | A | 1/1989 | Mullis et al. |
| 5,066,584 | A | 11/1991 | Gyllensten et al. |
| 5,691,146 | A | 11/1997 | Mayrand |
| 6,059,975 | A | 5/2000 | Alexandratos et al. |
| 6,183,698 | B1 | 2/2001 | Vassiliou et al. |
| 6,287,850 | B1 | 9/2001 | Besemer et al. |
| 6,291,183 | B1 | 9/2001 | Pirrung et al. |
| 6,297,018 | B1 | 10/2001 | French et al. |
| 6,306,643 | B1 | 10/2001 | Gentalen et al. |
| 6,308,170 | B1 | 10/2001 | Balaban |
| 6,391,544 | B1 | 5/2002 | Salituro et al. |
| 6,642,000 | B1 | 11/2003 | Strizhkov et al. |
| 6,664,053 | B1 | 12/2003 | Kovacs et al. |
| 2003/0134307 | A1 | 7/2003 | Beckman et al. |

FOREIGN PATENT DOCUMENTS

WO WO 2006/088445 8/2006

OTHER PUBLICATIONS

Achenbach et al., "Dechloromonas agitata gen. nov., sp. nov. and Dechlorosoma suillum gen. nov:, sp. nov., two novel environmentally dominant (per) chlorate-reducing bacteria and their phylogenetic position", Int. J. Syst. Evol. Microbiol. 51:527-533, 2001.

Altschul et al., "Gapped BLAST and PSI-BLAST: a new generation of protein database search programs," Nucl. Acid Res. 25:3389-39402, 1997.

Amann et al., "Phylogenetic Identification and In Situ Detection of Individual Microbial Cells without Cultivation," Microbiol. Rev. 59:143-169, 1995.

Bagasra et al., In Situ PCR Techniques, 1997.

Beaucage et. al., "Deoxynucleoside Phosphoramidites—A New Class of Key Intermediates for Deoxypolynucleotide Synthesis," 1981, Tetrahedron Letts., 22(20):1859-1862.

Bender et al., "Sequencing and Transcriptional Analysis of the Chlorite Dismutase Gene of *Dechloromonas agitata* and Its Use as a Metabolic Probe," Applied and Environmental Microbiology, Oct. 2002, vol. 68. No. 10, pp. 4820-4826.

Bender et al. "Metabolic Primers for Detection of (Per)chlorate-Reducing Bacteria in the Environment and Phylogenetic analysis of cld Gene Sequences," Applied and Environmental Microbiology. Sep. 2004, vol. 70. No. 9, pp. 5651-5658.

Berks, "A common export pathway for proteins binding complex redox cofactors", Mol. Microbiol., 22:393-404, 1996.

Berks et al., "The Tat protein export pathway," Mol. Microbiol., 35:260-274, 2000.

Braker et al., "Development of PCR Primer Systems for Amplification of Nitrite Reductase Genes (nirK and nirS) To Detect Denitrifying Bacteria in Environmental Samples," Appl. Environ. Microbiol., 64:3769-3775, 1998.

Bruce et al., "Reduction of (per)chlorate by a novel organism isolated from paper mill waste," Environ. Microbiol. 1:319-329, 1999.

Bustin, "Absolute quantification of mRNA using real-time reverse transcription polymerase chain reaction assays," Journal of Molecular Endocrinology 25:169-193, 2000.

Chaudhuri et al., "Environmental Factors That Control Microbial Perchlorate Reduction," Appl. Environ. Microbiol., 68:4425-2230, 2002.

Coates et al., "Ubiquity and Diversity of Dissimilatory (Per)chlorate-Reducing Bacteria," Appl. Environ. Microbiol. 65:5234-5241, 1999.

Danielsson-Thorell, "A Gene Cluster for Chlorate Metabolism in *Ideonella dechloratans*," Appl. Environ. Microbiol. 69:5585-5592, 2003.

Dunbar et al., "Genetic Diversity through the Looking Glass: Effect of Enrichment Bias," Appl. Envirion. Microbiol. 63:1326-1331, 1997.

Griffin, Hugh G. and Griffin, Annette M., eds., "PCR Technology: Current Innovations," CRC Press, 1994.

Guigliarelli et al., "Complete Coordination of the Four Fe-S Centers of the β Subunit from *Escherichia coli* Nitrate Reductase. Physiological, Biochemical, and EPR Characterization of Site-Directed Mutants Lacking the Highest or Lowest Potential [4Fe-4S] Clusters," Biochemistry, 35:4828-4836, 1996.

Hunter, "Bioremediation of Chlorate or Perchlorate Contaminated Water Using Permeable Barriers Containing Vegetable Oil," Curr. Microbiol. 45:287-292, 2002.

Innis et al. eds. "PCR Protocols: A Guide to Methods and Applications," Academic Press Inc., San Diego, Calif, 1990.

(Continued)

*Primary Examiner*—Young J Kim
(74) *Attorney, Agent, or Firm*—Marshall, Gerstein & Borun LLP

(57) ABSTRACT

The present invention is directed to metabolic primers for the detection of perchlorate-reducing bacteria and methods and compositions for use of the same in environmental bioremediation.

19 Claims, 8 Drawing Sheets

OTHER PUBLICATIONS

Iverson et al., "Heme packing motifs revealed by the crystal structure of the tetra-heme cytochrome c554 from, *Nitrosomonas europaea*," Nat. Struct. Biol., 5:1005-1012, 1998.

Jormakka et al., "Architecture of NarGH Reveals a Structural Classification of Mo-bisMGD Enzymes," Structure, 12:95-104, 2004.

Kaeberlein et al., "Isolating "Uncultivable" Microorganisms in Pure Culture in a Simulated Natural Environment," Science, 296:1127-1129, 2002.

Kengen et al., "Purification and Characterization of (Per)Chlorate Reductase from the Chlorate-Respiring Strain GR-1," J. Bacteriol 181:6706-6711, 1999.

Kisker et al., "Molybdenum-CoFactor—Containing Enzymes: Structure and Mechanism," Annu Rev. Biochem., 66:233-267, 1997.

Kim et al., "Microbial Reduction of Perchlorate in Pure and Mixed Culture Packed-Bed Bioreactors," Water Res. 35:3071-3076, 2001.

Krafft et al., "Cloning and Sequencing of the Genes Encoding the Periplasmic-Cytochrome B-Containing Selenate Reductase of *Thauera selenatis*," DNA Sequence 10:365-377, 2000.

Logan et al., "Kinetics of Perchlorate- and Chlorate-Respiring Bacteria," Appl. Environ. Microbiol. 67:2499-2506, 2001.

Mackay et al., "Real-time PCR in virology," Nucleic Acids Research 30:1292-1305, 2002.

McDevitt et al., "Molecular analysis of dimethyl sulphide dehydrogenase from *Rhodovulum sulfidohilum*: its place in the dimethyl sulphoxide reductase family of microbial molybdopterin-containing enzymes," Molecular Microbiology 44:1575-1587, 2002.

McDevitt et al., "Characterization of the Redox Centers in *Dimethyl sulfide* Dehydrogenase fro *Rhodovulum sulfidophilum*," Biochemistry 41:15234-15244, 2002.

McEwan et al., "The DMSO Reductase Family of Microbial Molybdenum Enzymes; Molecular Properties and Role in the Dissimilatory Reduction of Toxic Elements," Geomicrobiology Journal 19:3-21, 2002.

Mesarch et al., "Development of Catechol 2,3-Dioxygenase-Specific Primers for Monitoring Bioremediation by Competitive Quantitative PCR," Appl. Environ. Microbiol. 66:678-683, 2000.

Needham-Vandevanter et al., "Characterization of an adduct between CC-1065 and a defined oligodeoxynucleotide duplex," Nucleic Acids Res. 12:6159-6168, 1984.

Nielsen et al., "Sequence-Selective Recognition of DNA by Strand Displacement with a Thymine-Substituted Polyamide," Science 254:1497-1500, 1991.

Olsen et al., "Microbial Ecology and Evolution: A Ribosomal RNA Approach," Annu. Rev. Microbiol. 40:337-365, 1986.

Poddar, "Symmetric vs asymmetric PCR and molecular beacon probe in the detection o a target gene o adenovirus," Molecular and Cellular Probes 14:25-32, 2000.

Rabus et al., "Genes involved in the anaerobic degradation of ethylbenzene in a denitrifying bacterium, strain EbN1," Arch Microbiol 178:506-516, 2002.

Renner et al., "Perchlorate-tainted wells spur government action," Environmental Science & Technology, Environmental News 32:210A, May 1, 1998.

Richardson, "Bacterial respiration: a flexible process for a changing environment," Microbiology 146:551-571, 2000.

Rikken et al., "Transformation of (per)chlorate into chloride by a newly isolated bacterium: reduction and dismutation," Appl. Microbiol. Biotechnol. 45:420-426, 1996.

Roldan et al., "Spectroscopic Characterization of a Novel Multiheme c-Type Cytochrome Widely Implicated in Bacterial Electron Transport," J. Biol. Chem. 273:28785-28790, 1998.

Sambrook et al., "Molecular Cloning: A Laboratory Manual," 3rd ed., vol. 1-3, Cold Spring Harbor Laboratory, Cold Spring Harbor, N.Y., 2001.

Shaw et al., "Boranophosphate Backbone: a Mimic of Phosphodiesters, Phosphorothioates, and Methyl Phosphonates," Methods In Enzymol. 313:226-257, 1999.

Shaw et al., "Oligonucleoside Boranophosphate (Borane Phosphonate)," in Methods in Molecular Biology, vol. 20, Protocols for Oligonucleotides and Analogs, 225-243, Sudhir Agrawal, ed., Humana Press Inc., 1993.

Thompson et al., "Clustal W: improving the sensitivity of progressive multiple sequence alignment through sequence weighting, position-specific gap penalties and weight matrix choice," Nucleic Acids Research, vol. 22, 22:4673-4680, 1994.

Thorell et al. "Cloning, characterisation, and expression of a novel gene encoding chlorite dismutase from *Ideonella dechloratans*," Biochimica et Biophysica Acta. Sep. 2002, vol. 1577. No. 3, pp. 445-451.

Tipton et al., "Transport and Biodegradation of Perchlorate in Soils," J. Environ. Qual. 32:40-46, 2003.

Urbansky, "Perchlorate Chemistry: Implications for Analysis and Remediation," Bioremediation Journal, vol. 2, 2:81-95, 1998.

Vanden Heuvel, ed., "PCR Protocols in Molecular Toxicology," CRC Press 1997.

Van Ginkel, et al., "Purification and characterization of chlorite dismutase: a novel oxygen-generating enzyme," Arch Microbiol 166:321-326, 1996.

Wallace et al., "Identification of an anaerobic bacterium which reduces perchlorate and chlorate as *Wolinella succinogenes*," Journal of Industrial Microbiology 16:68-72, 1996.

Wheeler et al., "Database resources of the National Center for Biotechnology Information: update, "Nucleic Acids Research, Database issue, 32:D35-40, 2004.

International Search Report in International Application No. PCT/US05/04657, dated Dec. 26, 2006.

Written Opinion of the International Searching Authority in International Application No. PCT/US05/04657, dated Dec. 26, 2006.

FIG. 2

```
St.GR1 PcrB   ----------ANVMKAPRRQLTYVTDXN (SEQ ID NO: 55)
D.agit PcrB   ----------MSNMTKSPKRQLAYADLNKCIGCQTCTVACKTLWTSGPGQDYMYWRNVETAPGLGYPRNWQSKGGG---YKDGVLQKGKIPPMID
D.arom PcrB   ----------MANVMKAPKRQLTYVTDLNKCIGCQTCTVACKKLWTTGPGQDFMYWRNVETTPGLGYPRNWQTKGGG---YKNGELQKGKIPPMID
T.sele SerB   -----MSRQLAYVFDLNKCIGCHTCIMACKQLWTNRDGREYMYMWNVESRPGKGYPKNWEQKGGGFD-KDGKLKTNGIIPIRAD
I.dech ClrB   -----MSRQVAVVFDLNKCIGCHTCIMACKQLWTNRDGREYMYMWNVETRPGKGYPKNWEGKGGGFD-QEGKLKTNGIIPIMAD
A.EbN1 EbdB   --MTYVQDGNKSELRKAKRQLVTVIDLNKCLGCQTCIVACKNIWTKRPGTEHMRWNNVTTYPGKGYPRDYERKGGGFL---RGEPQPGVLPTLID
R.sulf DdhB   --MVKRQISMVLDLNKCIGCQTCTSACKLQWINRNGREYMYWNVETHPGPGYPRNYEHSGGGFD--EEGALKIGITPSAED
H.mars NarH   MSSDQQDDQGEEDTLVNADGVDHQVAMVMDLNKCIGCQTCTIACKNLWTEDGGSEYMYWNNVETKPGEGYPRGWENSGGGWKSGEHKERQPGEIPDEED D.agit PcrB   YGVPFEFDYAGR-LFEGKKERARPSP-------TPRYAPNWDEDQGAGEYPNNSFFYVPRMCNHCAKPACLEACPNEAIYKREQDGLVVHQEKCKGAQA
D.arom PcrB   YGIPFEFDYAGR-LFEGKKERVRPSP-------TPRSAPNWDEDQGAGEYPNNSFFYLPRMCNHCYKPACLEACPNEAIYKREQDGIVVHQDKCKGAQA
T.sele SerB   YGGTWNYNLLET-LVEGKSNQVVPDE-------KPTWGPNWDEDEGKGEFPNNHYFYLPRICNHCSNPACLAACPTKAIYKREDGLVVDQSRCKGYRY
I.dech ClrB   YGGRIGDFNLNEVLLEGKADQVVPHE-------KATWGPNWDEDEGKGEFPNNHSFYLPRICNHCSNPACLAACPTKAIYKPEDGIVVDQTRCRGYRY
A.EbN1 EbdB   SGDDFQFNHKEV-FYEGKGQTVHFHPTSKSTGKDPAWGYNWDEDQGGGKWPNPFFFYLARMCNHCTNPACLAACPTGAIYKREDNGIVLVDQERCKGHRH
R.sulf DdhB   YGIPWEYNYEEA-LMTGTDPWLRPNV-------KPTWGANWNEDEGRGEYPNSYFYLPRICNHCANPGCLAACARNAIYKQEDGIVLVDQERCGYRY
H.mars NarH   YGRAWEFNHEEI-MYEGSDEPLRPRD-------GAEWGPNWDEDQGAGEYPNSYFYLPRICNHCTHPSCVEACPRSALYKQEDGIVLVDQDRCRGYRY D.agit PcrB   CIQSCPYFNAQVNKANKCIGCFPRIEK-GV------APACVAECAGRAMHVGFIDDQESSVFKLVKRFGVALPLHPEYGTEPNVFYVPVL-GPRVE
D.arom PcrB   CVQSCPYAKPYFNPVANKANKCIGCFPRIEQ-GV------APCCVAQCVGRAMHVGFIDDTNSSVHKLIRLYKVALPLHPEFGTEPNVFYVPVL-GPRME
T.sele SerB   CVKACPYGKMYFNLQKGTSEKCIGCYPRVEK-GE------APACVKQCSGRIRFWGYRDDKDGPIYKLVDQWKVALPLHAEYGTEPNVFYVPPMNTTPPPF
I.dech ClrB   CVKACPYGKMYFNLQKGKSEKCIGCYPRVEK-GE------APACVKQCSGRIRFWGYRDKNGPIYKLVEQWKVALPLHAEYGTEPNVFYVPPMNTTPPPF
A.EbN1 EbdB   CVEACPYKAIYFNPVSQTSEKCILCYPRIEK-GI------ANACNRQCPGRVRAFGYLDDTTSHVHKLVKKWKVALPLHAEYGTGPNIYYVPPM--GARGF
R.sulf DdhB   CITACPYKKVYFNEQISKAEKCIFCYPRIEK-GL------PTACAKQCVGRIRFIGYLDDEAGPVHLLVERYKVAIPLHPEWGTKPSVFVYPL--APPRI
H.mars NarH   CVEGCPYKKVYNTVSKKSEKCIFCYPRIEGEGPDGETFAPACAEECPPQLRLVGFLDDEEGPIHKLVNEYEVALPLHPEFRTQPNVYIPPF--APGQH D.agit PcrB   MPNGEHTADPKISMTQLEQLFGKQVREVLKTLQAEREKKIKNQPSELMDILIGRRSADMMISPMT------(SEQ ID NO: 30)
D.arom PcrB   LPNGELSTDPKIPLAQLEGLFGKQVRDVLAILQTEREKKMKGLASDLMDVLIGRRSADMMISPLT------(SEQ ID NO: 56)
T.sele SerB   EEDGRLGDKPRIPIEDLEALFGPGVKQALATLGGEMAKRRKAQASELTDILIGYTNKDRYGI--------(SEQ ID NO: 35)
I.dech ClrB   EEDGRLGDKPRIPIEDLEALFGPGVKQALATLGGEMAKRRKAQASELTDILIGFTNKDRYGV--------(SEQ ID NO: 36)
A.EbN1 EbdB   GEDGEITDKTRIPLDVLEGIFGPEVKRVLAVLHTRENMRAGRGSELMDLLISKKWSDRFGGFTNDPLTQS (SEQ ID NO: 37)
R.sulf DdhB   GDDGEPTEETRVPLAYLKELFGEAVVPALEFTLKTERAKKQSGAESELMDTLIGYRHPEMFKLS------(SEQ ID NO: 38)
H.mars NarH   TEDGETVDIDRIPRQYLRDLFGDGVDQALDTIERERQRARQGEDSELMELLQDKNPAKQYRLEVFDDE--(SEQ ID NO: 39)
```

FIG. 3

```
D.arom PcrC   MIKILALATLLISGFLPGVTVAQQAE--YIGFRACTKCHDSQGETWRASAHAKAFDSLKPNAKSEAKTKAKLDPKKDYTQDKNCVGCHVTGYGEPGGPVS
N.euro c554   MKIMIACGLVAAALFTLTSGQSLAADAPFEGRKKCSSCHKAQAQSWKDTAHAKAMESLKPNVKKEAKQKAKLDPAKDYTQDKDCVGCHVDGFGQKGGY--

D.arom PcrC   GASLDDMKTLVGVTCBSCHGAGGKFRNLHGEASDRLKNQGETSERKQIVTAGQNFDMEKACARCHLNFEGSTKHDAKAPFTPFSPSVGSKYQFDRQKSYM
N.euro c554   -TIESPKPMLTGVGCESCHGPGRNFRGDHRKSGQAFEKSGKKTPRKDLAKKGQDFHFEERCSACHLNYEGSPWKGAKAPYTPFTPEVDAKYTFKFDEMVK D.arom PcrC   TTGAGNPIHTHFKLRGVPKGDPVPAVRAKLQEDAPEPE---   (SEQ ID NO: 57)
N.euro c554   ---EVKAMHEHYKLEGVFEGEPKFKFHDEFQASAKPAKKGK   (SEQ ID NO: 40)
```

METABOLIC PRIMERS FOR THE DETECTION OF PERCHLORATE-REDUCING BACTERIA AND METHODS OF USE THEREOF

This application is a U.S. Utility Application that claims the benefit of U.S. Provisional Application No. 60/833,825, which was filed Jul. 27, 2006. The entire disclosure of the foregoing application is incorporated herein by reference.

Certain aspects of the studies described herein were Federally-funded with the support of grant # DACA72-00-C-0016 from the Department of Defense.

BACKGROUND

1. Field of the Invention

This invention relates to bioremediation of contaminants in the environmental samples, including for example, contamination in particulates such as soil and also in fluids such as groundwater. More particularly, the present invention is directed to methods and compositions for the detection of perchlorate-reducing bacteria at target decontamination site.

2. Background of the Related Art

Chemical contamination of the environment, particularly of soil and groundwater, is a widespread problem throughout the industrialized world. Industrial pollution has contaminated millions of acres of soil and associated aquifers. Often, cleanup of the contamination is hindered because the cost of remediation is significant. Moreover, many of the remediation techniques create additional problems which cause the land to remain unused or abandoned.

Recently, widespread perchlorate contamination of drinking water wells throughout the United States and especially throughout the southwest has become a significant cause for concern. Perchlorate contamination of ground and surface waters originates from, and is a direct effect of, unregulated ammonium perchlorate disposal practices from 1950 to 1997 (Renner et al., Environ. Sci. Technol. News 32:210A, 1998). Ammonium perchlorate is an oxidant that is widely used in the aerospace, munitions, and fireworks industries. Widespread contamination has been documented in the waterways of California, and at least 19 other states in the United States. Similar contaminations have been reported in other countries that have aerospace, munitions and fireworks industries.

Perchlorate has been linked to a number of problems in human health. Excessive intake of perchlorate blocks iodine uptake and inhibits thyroid function and production of thyroid hormones, in addition, gastrointestinal irritation and skin rash, and hematological effects including agranulocytosis and lymphadenopathy have also been observed. In addition, it has been established that there is neurodevelopmental toxicity associated with perchlorate ingestion. As a result of these significant health concerns, drinking water utilities have begun monitoring and reporting perchlorate levels to the State agencies. In some states the Health Services Departments have set maximum limits on the amount of perchlorate in drinking water; this figure is typically in the order of 18 parts per billion (ppb) in order to minimize the risks to human health. The Environmental Protection Agency has established a provisional reference dose ("RFD") of 14 mg of perchlorate per kg of body weight per day. Practical and efficient methods to treat water contaminated by perchlorate are needed to insure a safe drinking water supply in many communities.

Current methods of perchlorate remediation rely on the use of ion exchange resins to sequester perchlorate ions. (see e.g., U.S. Pat. No. 6,059,975). Conventional perchlorate-removal ion exchange resins have low selectivity coefficients and as such these resins are capable of loading only a few kilograms of perchlorate per cubic meter of removal resin. This produces a waste mass of loaded resin that must be disposed through, e.g., incineration. Disposal costs for these resins are therefore prohibitive because of the bulk volume of loaded to be disposed relative to the amount of perchlorate removed from the environmental target site. Other methods of perchlorate removal are actively being pursued, with bioremediation technologies emerging as a cost-effective and less-invasive alternative to physical or chemical practices (Urbansky et al., Biorem. J.: 81-95, 1998).

Natural attenuation of perchlorate is a cost-effective alternative to current methods of perchlorate remediation. Such natural attenuation systems have been used in bioremediation of other contaminants and include the use of microbial populations to accelerate the breakdown of solids and the various contaminants associated with waste water. Such microbes are permitted to act upon the waste water or contaminated soils and they act to remove the pollutants faster than if nothing were used, and do so without the hazards and difficulties associated with chemical treatment.

The success of natural perchlorate remediation is dependent on the presence and activity of dissimilatory (per)chlorate-reducing bacteria (DPRB) within the target site that is undergoing remediation. Within the last 7 years, more than 40 different strains of dissimilatory (per)chlorate-reducing bacteria (DPRB) have been isolated from a diverse range of environments (Bruce et al., Environ. Microbiol. 1:319-329, 1999; Coates et al., Appl. Environ. Microbiol. 65:5234-5241., 1999; Kim et al., Water Res. 35:3071-3076., 2001; Logan et al., Appl. Environ. Microbiol. 67:2499-2506, 2001, 18, Rikken et al., Appl. Microbiol. Biotechnol., 45:420-426, 1996; Wallace et al., J. Ind. Microbiol. 16:68-72, 1996). Because of the metabolic capability and ubiquity of DPRB (Coates et al., Appl. Environ. Microbiol. 65:5234-5241., 1999), natural attenuation of perchlorate is garnering more and more interest. While studies by various groups have shown the ability of microbes to remediate perchlorate under environmental conditions (Hunter, Curr. Microbiol. 45:287-292., 2002; Kim et al., Water Res. 35:3071-3076., 2001; Tipton et al., J. Environ. Qual. 32:40-46, 2003), a quick, reliable method for detecting the presence and effectiveness of DPRB is needed to determine the natural attenuation candidacy of a contaminated site as well as for monitoring active degradation.

Traditionally, contaminant site evaluation for the presence of DPRB has been performed using labor-intensive enumeration and isolation techniques. However, it is well known that cultivation techniques are time-consuming and often prove unsuccessful in isolating the target bacteria due to both media selectivity and organism culturability (Dunbar et al., Appl. Environ. Microbiol. 63:1326-1331, 1997; Kaeberlein et al., Science, 296:1127-1129, 2002). To alleviate the limitations of cultivation-based methods, molecular techniques using the 16S rRNA gene have been employed to examine bacterial diversity in the environment (Aman et al., Microbiol. Rev. 59:143-169, 1995, Olsen et al., Annu. Rev. Microbiol. 40:337-365, 1986), and numerous primer sets have been developed for the 16S rRNA gene that target specific groups of bacteria. However, due to the fact that there is significant phylogenetic diversity of DPRB and because of their close phylogenetic relationships to non-(per)chlorate-reducing relatives, detection of DPRB using 16S ribosomal DNA (rDNA) primers is not recommended (Achenbach et al., Int. J. Syst. Evol. Microbiol. 51:527-533, 2001). As such, there remains a need to identify a more inclusive approach to the detection of DPRB that would allow an efficient molecular identification technique that will facilitate the rapid identification of the presence of DPRB at a given target site and/or allow prediction of whether a given target site is capable of undergoing perchlorate remediation.

SUMMARY OF THE INVENTION

The present invention is directed to methods and compositions for use in bioremediation-related applications. Specific detection of chlorate reducing bacteria is facilitated by the present invention because it involves determining the presence of perchlorate reductase in a given sample. Perchlorate reductase is only present in perchlorate reducing bacteria as opposed to chlorite dismutase, which is present in both chlorate reducing bacteria and perchlorate reducing bacteria.

A specific aspect of the present invention, which in one aspect provides a composition comprising a first primer and a second primer, wherein the first primer has a nucleic acid sequence that comprises a sequence of SEQ ID NO:1 or SEQ ID NO:11 and the second primer has a nucleic acid sequence that comprises a sequence of SEQ ID NO:2 or SEQ ID NO:12, wherein the first and second primers are capable of hybridizing to a perchlorate reductase gene, more particularly, capable of hybridizing to pcrA gene. In preferred embodiments, the pcrA gene has the sequence of SEQ ID NO: 27 (from Genbank Accession No. AY180108).

In additional embodiments, the composition may further comprise a third primer and a fourth primer, wherein the third primer has a nucleic acid sequence that comprises a sequence of SEQ ID NO:3 and the fourth primer has a nucleic acid sequence that comprises a sequence of SEQ ID NO:4, wherein the third and fourth primers are capable of hybridizing to a perchlorate reductase gene.

In an alternative embodiment, the composition is one in which there is third primer and a fourth primer, wherein the third primer has a nucleic acid sequence that comprises a sequence of SEQ ID NO:5 or SEQ ID NO:13 and the fourth primer has a nucleic acid sequence that comprises a sequence of SEQ ID NO:6 or SEQ ID NO:14, wherein the third and fourth primers are capable of hybridizing to a perchlorate reductase gene.

In yet another alternative embodiment, the composition is one in which there is a third primer and a fourth primer wherein the third primer has a nucleic acid sequence that comprises a sequence of SEQ ID NO:7 and the fourth primer has a nucleic acid sequence that comprises a sequence of SEQ ID NO:8 wherein the third and fourth primers are capable of hybridizing to a perchlorate reductase gene.

In other specific embodiments, there is a composition that comprises a first primer and a second primer, wherein the first primer has a nucleic acid sequence that comprises a sequence of SEQ ID NO:3 and the second primer has a nucleic acid sequence that comprises a sequence of SEQ ID NO:4, wherein the first and second primers are capable of hybridizing to a perchlorate reductase gene. In other embodiments, such a composition may further comprise a third primer and a fourth primer, wherein the third primer has a nucleic acid sequence that comprises a sequence of SEQ ID NO:5 or SEQ ID NO:13 and the fourth primer has a nucleic acid sequence that comprises a sequence of SEQ ID NO:6 or SEQ ID NO:14, wherein the third and fourth primers are capable of hybridizing to a perchlorate reductase gene. In still other embodiments, the composition is one in which the third primer has a nucleic acid sequence that comprises a sequence of SEQ ID NO:7 and the fourth primer has a nucleic acid sequence that comprises a sequence of SEQ ID NO:8 wherein the third and fourth primers are capable of hybridizing to a perchlorate reductase gene.

Still other compositions of the invention comprise a first primer and a second primer, wherein the first primer has a nucleic acid sequence that comprises a sequence of SEQ ID NO:5 or SEQ ID NO:13 and the second primer has a nucleic acid sequence that comprises a sequence of SEQ ID NO:6 or SEQ ID NO:14, wherein the first and second primers are capable of hybridizing to a perchlorate reductase gene. In exemplary embodiments, such compositions may further comprise a third primer and a fourth primer, wherein the third primer has a nucleic acid sequence that comprises a sequence of SEQ ID NO:7 and the fourth primer has a nucleic acid sequence that comprises a sequence of SEQ ID NO:8 wherein the third and fourth primers are capable of hybridizing to a perchlorate reductase gene.

Additional aspects contemplate compositions that further comprise a fifth primer and a sixth primer, such that in addition to SEQ ID NO:1 or 11, SEQ ID NO:2 or 12, SEQ ID NO:3, SEQ ID NO:4, the composition further comprises a fifth primer and a sixth primer, wherein the fifth primer has a nucleic acid sequence that comprises a sequence of SEQ ID NO:5 or SEQ ID NO:13 and the sixth primer has a nucleic acid sequence that comprises a sequence of SEQ ID NO:6 or SEQ ID NO:14, wherein the fifth and sixth primers are capable of hybridizing to a perchlorate reductase gene. In still other alternatives, the composition is one in which the fifth primer has a nucleic acid sequence that comprises a sequence of SEQ ID NO:7 and the sixth primer has a nucleic acid sequence that comprises a sequence of SEQ ID NO:8, wherein the fifth and sixth primers are capable of hybridizing to a perchlorate reductase gene.

Other preferred compositions are those in which further comprise a seventh primer and an eighth primer, wherein the seventh primer has a nucleic acid sequence that comprises a sequence of SEQ ID NO:7 and the eighth primer has a nucleic acid sequence that comprises a sequence of SEQ ID NO:8, wherein the seventh and eighth primers are capable of hybridizing to a perchlorate reductase gene.

Preferably, each of the primers each independently comprise between 20 and 30 nucleotide bases in length. Other preferred embodiments contemplate that the primers each independently comprise between 20 and 40 nucleotide bases in length. Still additional embodiments contemplate that each of the primers each independently comprise between 20 and 50 nucleotide bases in length.

In specific aspects of the invention, it is contemplated that the perchlorate reductase gene is from dissimilatory perchlorate-reducing bacteria (DPRB) species. DPRB species are well known to those of skill in the art, and simply by way of example, include, but are not limited to a bacterium from the *Dechloromonas* spp., *Azoarcus* spp., *Dechlorospirillum* spp., *Dechloromarinus* spp., *Ideonella* spp., *Magnetospirillum* spp., *Pseudomonas* spp., *Rhodocyclus* spp., *Rhodospirillum* spp., *Azospirillum* spp., *Wolinella* spp., *Xanthomonas* spp. In specific embodiments, the DPRB is selected from the group consisting of *Dechloromonas agitate, Dechloromonas aromatica, Azospira suillum, Dechlorospirillum anomalous, Dechloromarinus chlorophilus, Ideonella dechloratans*, and *Magnetospirillum magnetotacticum*.

In specific embodiments, the primer is detectably labeled.

Also contemplated herein is an oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12. Other preferred oligonucleotide primer pairs are those in which the first primer of the primer pair comprises a sequence of SEQ ID NO:3 and the second primer of the primer pair comprises a sequence of SEQ ID NO:4. Yet further preferred primer pairs include those in which the first primer of the primer pair comprises a sequence of SEQ ID NO:5 or SEQ ID NO:13 and the second primer of the primer pair comprises a sequence of SEQ ID NO:6 or SEQ ID NO:14. In still another exemplary embodiment, the first primer of the primer pair comprises a sequence of SEQ ID NO:7 and the second primer of the primer pair comprises a sequence of SEQ ID NO:8. Preferably, in such compositions, at least one of the primers in a primer pair of the invention is detectably labeled.

Other aspects specifically contemplated an oligonucleotide primer which has the nucleotide sequence defined in any one of SEQ ID NOs: 1, 2, 3, 4, 5, 6, 7, 8, 11, 12, 13, or 14. Such an oligonucleotide may be between 20 and 50 nucleotide bases. Preferably, the oligonucleotide primer is detectably labeled. The label may be any label that is conventionally used to facilitate detection of the primer or the product of the reaction in which the primer is used. For example, the primer is labeled with an epitope, fluorophore, metal particle, enzyme, carbohydrate, polypeptide, radioactive isotope, dye, biotin, or digitonin.

The oligonucleotide primer pairs discussed above may be such that at least on the oligonucleotides in the pair is labeled with an epitope, fluorophore, metal particle, enzyme, carbohydrate, polypeptide, radioactive isotope, dye, biotin, or digitonin.

The present invention particularly contemplates methods of detecting the presence of chlorate reducing bacteria in a sample comprising subjecting DNA of bacterial cells in the sample to a first polymerase chain reaction amplification using a pair of primers of an oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8; and detecting the product or products of the first polymerase chain reaction amplification, thereby identifying the presence of the perchlorate-reducing bacteria in the sample.

In additional embodiments, the method may advantageously further comprise subjecting the DNA to a second polymerase chain reaction amplification using a pair of primers of oligonucleotide primer pair (e.g., wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8), as long as the primer pair in the second polymerase chain reaction amplification is one that is a different primer set than the primer set that is used in first polymerase chain reaction amplification; and detecting the product or products of the second polymerase chain reaction amplification thereby identifying the presence of the perchlorate-reducing bacteria in the sample.

In specific embodiments, the methods of the invention can be used to distinguish whether there are perchlorate reducing bacteria in a sample. As noted above, perchlorate reductase is present only in perchlorate reducing bacteria and is not present in chlorate reducing bacteria. Chlorite dismutase, the only other enzyme in the perchlorate reduction pathway to have been characterized, is useful for identifying both perchlorate reducing bacteria and chlorate reducing bacteria. Hence, using the methods of the invention it is possible to specifically identify perchlorate reducing bacteria in a sample that contains both chlorate and perchlorate reducing bacteria. Exemplary such methods may utilize the chlorite dismutase detection methods described in e.g., PCT application PCT/US2005/004657 (inventors Achenbach et al., filed Feb. 11, 2005) to identify bacteria that are capable of reducing both perchlorate and chlorate, and then subsequently use the perchlorate reductase-based detection methods discussed herein to further identify only those bacteria that are perchlorate reducers.

Other methods of the invention involve detecting the presence of perchlorate reducing bacteria in a sample comprising subjecting DNA from the sample to a first polymerase chain reaction amplification using a pair of primers of (e.g., oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8); and detecting the product or products of the first polymerase chain reaction amplification, thereby identifying the presence of the perchlorate-reducing bacteria in the sample.

Also contemplated is a method of detecting the presence of perchlorate-reducing bacteria in a sample comprising: (a) subjecting DNA from the sample to a first polymerase chain reaction amplification using a pair of primers (e.g., oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8); (b) isolating the amplification products from step (a); (c) using the amplification products isolated in step (b) as a template for a second polymerase chain reaction amplification using a second primer pair that is different from the primer pair used in the first polymerase chain reaction; and (d) detecting the product or products of the second polymerase chain reaction amplification, thereby identifying the presence of the perchlorate-reducing bacteria in the sample.

Another method of the invention comprises three amplification steps for detecting the presence of perchlorate-reducing bacteria in a sample, wherein the method comprises subjecting DNA from the sample to a first polymerase chain reaction amplification using a pair of primers (e.g., oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8); (b) isolating the amplification products from step (a); (c) using the amplification products isolated in step (b) as a template for a second polymerase chain reaction amplification using a second primer pair that is different from the primer pair used in the first polymerase chain reaction; (d) isolating the amplification products from step (c); (e) using the amplification products isolated in step (d) as a template for a third polymerase chain reaction amplification using a third primer pair that is different from the primer pair used in the first or the second polymerase chain reaction; and (f) detecting the product or products of the third polymerase chain reaction amplification, thereby identifying the presence of the perchlorate-reducing bacteria in the sample.

Still a further method is one which employs four amplification reaction steps for detecting the presence of perchlorate-reducing bacteria in a sample comprising (a) subjecting DNA from the sample to a first polymerase chain reaction amplification using a pair of primers (oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8); (b) isolating the amplification products from step (a); (c) using the amplification products isolated in step (b) as a template for a second polymerase chain reaction amplification using a second primer pair that is different from the primer pair used in the first polymerase chain reaction; (d) isolating the amplification products from step (c); (e) using the amplification products isolated in step (d) as a template for a third polymerase chain reaction amplification using a third primer pair that is different from the primer pair used in the first or the second polymerase chain reaction; (f) isolating the amplification products from step (e); (g) using the amplification products isolated in step (d) as a template for a fourth polymerase chain reaction amplification using a fourth primer pair from claim 20, claim 21, claim 22 or claim 23 that is different from the primer pair used in the first, second or the third polymerase chain reaction; and (h) detecting the product or products of the third polymerase chain reaction amplification, thereby identifying the presence of the perchlorate-reducing bacteria in the sample.

In such methods, the DNA is preferably isolated from a bacterial lysate from the bioremediation formulation prior to the initial first polymerase chain reaction amplification step. In specific embodiments, the bioremediation formulation is a cocktail of microorganisms that are used to remove contaminants from a sample of soil or water in need of decontamination, wherein the cocktail of microorganisms comprises a mixture of DPRBs. In preferred embodiments, the cocktail of microorganisms further microorganisms that are denitrifiers. Preferably, the cocktail of microorganisms further comprises microorganisms that can degrade toluene, xylene, benzene, petroleum, and creosote.

The soil or water samples have been contaminated with perchlorate as a result of for example, waste disposal from paper mill waste, airbag production, firework manufacture and use, fertilizer manufacture and use.

Also provided are methods of determining whether a bioremediation formulation that comprises bacteria will be effective at decreasing perchlorate contamination, wherein the method comprises subjecting DNA from the bioremediation formulation to a first polymerase chain reaction amplification using a pair of primers (oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8); and detecting the product or products of the first polymerase chain reaction amplification, wherein the presence of the amplification products indicates the presence of perchlorate reducing bacteria in bioremediation formulation thereby indicating that the formulation is effective at reducing perchlorate contamination. The method may further comprise subjecting the DNA to a second, third or fourth polymerase chain reaction amplification using a second, third or fourth pair of primers that is different from the first (and corresponding second, and third where there are three or four amplifications) pair of primers; and detecting the presence of perchlorate-reducing bacteria in the bioremediation formulation by visualizing the product or products of the second polymerase chain reaction amplification, wherein the presence of the amplification products indicates that the formulation is effective at reducing perchlorate contamination.

Also taught is a method of determining whether a bioremediation formulation that comprises bacteria will be effective at decreasing perchlorate contamination comprising (a) subjecting the DNA from the bioremediation formulation to a first polymerase chain reaction amplification using a pair of primers (e.g., an oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8); (b) isolating the amplification products from step (a); (c) using the amplification products isolated in step (b) as a template for a second polymerase chain reaction amplification using a primer pair that is different from the pair of primers used in the first polymerase chain reaction amplification; and (d) detecting the perchlorate-reducing bacteria by visualizing the product or products of the second polymerase chain reaction amplification.

Still another method is one for determining whether a bioremediation formulation that comprises bacteria will be effective at decreasing perchlorate contamination comprising (a) subjecting the DNA from the bioremediation formulation to a first polymerase chain reaction amplification using a pair of primers (e.g., oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8); (b) isolating the amplification products from step (a); (c) using the amplification products isolated in step (b) as a template for a second polymerase chain reaction amplification using a primer pair that is different from the pair of primers used in the first polymerase chain reaction amplification; (d) isolating the amplification products from step (c); (e) using the amplification products isolated in step (d) as a template for a third polymerase chain reaction amplification using a primer pair that is different from the pair of primers used in the first and second polymerase chain reaction amplification; and (f) detecting the perchlorate-reducing bacteria by visualizing the product or products of the second polymerase chain reaction amplification.

Still another method for determining whether a bioremediation formulation that comprises bacteria will be effective at decreasing perchlorate contamination comprises (a) subjecting the DNA from the bioremediation formulation to a first polymerase chain reaction amplification using a pair of primers (e.g., oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8); (b) isolating the amplification products from step (a); (c) using the amplification products isolated in step (b) as a template for a second polymerase chain reaction amplification using a primer pair that is different from the pair of primers used in the first polymerase chain reaction amplification; (d) isolating the amplification products from step (c); (e) using the amplification products isolated in step (d) as a template for a third polymerase chain reaction amplification using a primer pair that is different from the pair of primers used in the first and second polymerase chain reaction amplification; (f) isolating the amplification products from step (e); (g) using the amplification products isolated in step (f) as a template for a fourth polymerase chain reaction amplification using a primer pair that is different from the pair of primers used in the first second and third polymerase chain reaction amplification; and (h) detecting the perchlorate-reducing bacteria by visualizing the product or products of the second polymerase chain reaction amplification.

These methods may be supplemented by further determining the presence of chlorite dismutase in the sample prior to determining the presence of perchlorate reductase in the sample. Such further methods advantageously may use polymerase chain reactions using primers selected from the group consisting of SEQ ID NO:15 through SEQ ID NO:24.

Also contemplated by the invention is a method of determining whether a sample contains bacteria that is reducing perchlorate in the sample comprising: isolating nucleic acid from the sample; incubating the nucleic acid with a DNase to isolate RNA; performing a reverse transcription reaction on the RNA using one or more of the primers selected from the group consisting of SEQ ID NO:1, 2, 3, 4, 5, 6, 7, 8, 11, 12, 13 and 14; and detecting the product or products of the reverse transcription reaction that are expressing perchlorate reductase, thereby identifying the presence of bacteria in the sample that are expressing perchlorate reductase for reducing the perchlorate content of the sample.

Another aspect contemplated is a method of determining whether a sample contains bacteria that is reducing perchlorate in the sample comprising: (a) isolating nucleic acid from the sample; (b) incubating the nucleic acid with a DNase to isolate RNA; (c) performing a reverse transcriptase reaction on the RNA using one or more of the primers selected from the group consisting of SEQ ID NO:1, 2, 3, 4, 5, 6, 7, 8, 11, 12, 13 and 14; (d) isolating the reaction products from step (c); (e) using the reaction products isolated in step (d) as a template for a polymerase chain reaction amplification using a primer pair (e.g., oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12; or where the first primer of the primer pair comprises a sequence of SEQ ID NO:3 and the second primer of the primer pair comprises a sequence of SEQ ID NO:4; or where the first primer of the primer pair comprises a sequence of SEQ ID NO:5 or SEQ ID NO:13 and the second primer of the primer pair comprises a sequence of SEQ ID NO:6 or SEQ ID NO:14 or where the first primer of the primer pair comprises a sequence of SEQ ID NO:7 and the second primer of the primer pair comprises a sequence of SEQ ID NO:8); and (f) detecting the product or products of the polymerase chain reaction amplification of step (e), thereby identifying the presence of bacteria in the sample that are expressing perchlorate reductase for reducing the perchlorate content of the sample.

In some embodiments, the method may further comprise determining the presence of chlorite dismutase in the sample prior to determining the presence of perchlorate reductase in the sample, for example, determining the presence of chlorite dismutase in the sample comprises performing polymerase chain reactions using primers selected from the group consisting of SEQ ID NO:15 through SEQ ID NO:24.

Further methods contemplate performing additional rounds of amplifications using primer pairs that are distinct from the first round of amplification.

The invention also is directed to kits for amplifying perchlorate reductase polynucleotide, the kit comprising: composition or an oligonucleotide pair or an oligonucleotide as described herein above, wherein the composition; and instructions for carrying out any one or more of the methods discussed above. Preferably, each of the primers are in separate containers. In specific embodiments, the kits further comprise an oligonucleotide primer or primer pair for amplifying chlorite dismutase, e.g., an oligonucleotide primer selected from the group consisting of SEQ ID NO:15 through SEQ ID NO:24. Preferably, the kits may further comprise enzymes and nucleotide components of a PCR reaction. The kits of the invention also may comprise one or more solid supports. In certain embodiments, the primers described herein are preferably arranged as arrays on a solid support. Preferably, the arrays are addressable and/or detectable such that the skilled individual may readily detect the primer from a signal or from a specific "address" or location on the solid support. Other embodiments contemplated are those in which the primers are provided in separate containers.

Also contemplated herein is a library of primers for the detection of a perchlorate reductase gene from DPRB, the library comprising at least 6 primers derived from the sequences set forth in SEQ ID NO:1, 2, 3, 4, 5, 6, 7, 8, 11, 12 13, or 14. Another library of primers is one for the detection of DPRB, the library comprising at least 6 primers derived from the sequences set forth in SEQ ID NO:1, 2, 3, 4, 5, 6, 7, 8, 11, 12, 13, or 14 for detecting perchlorate reductase and the sequences set forth in SEQ ID NO:15, 16, 17, 18, 19, 20, 21, 22, 23, or 24 for detecting chlorite dismutase.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 2. Amino acid alignment of the □-subunit of perchlorate reductases (PcrB) from strain GR-1 (St.GR1) (N-terminal sequence only), *D. agitata* (D.agit), and *D. aromatica* (D.arom), selenate reductase B (SerB) from *T. selenatis* (T.sele), chlorate reductase (ClrB) from *I. dechloratans* (I.dech), ethylbenzene dehydrogenase B (EbdB) from *Azoarcus* sp. strain EbN1 (A.EbN1), dimethyl sulfide dehydrogenase B (DdhB) from *R. sulfidophilum* (R.sulf), and nitrate reductase H (NarH) from *H. marismortui* (H.mars). Light shading indicates amino acids identical to amino acids in both perchlorate reductases. Dark shading indicates conserved cysteine clusters for Fe—S center binding. The numbers below the cysteine residues indicate the associated Fe—S centers.

FIG. 3. Amino acid alignment of the □-subunit of perchlorate reductase (PcrC) from *D. aromatica* (D.arom) and cytochrome c554 from *N. europaea* (N.euro). Shading indicates identical residues, while boldface and underlining indicate residues shown to bind heme in cytochrome c554

DESCRIPTION OF THE PREFERRED EMBODIMENTS

Figure 1:
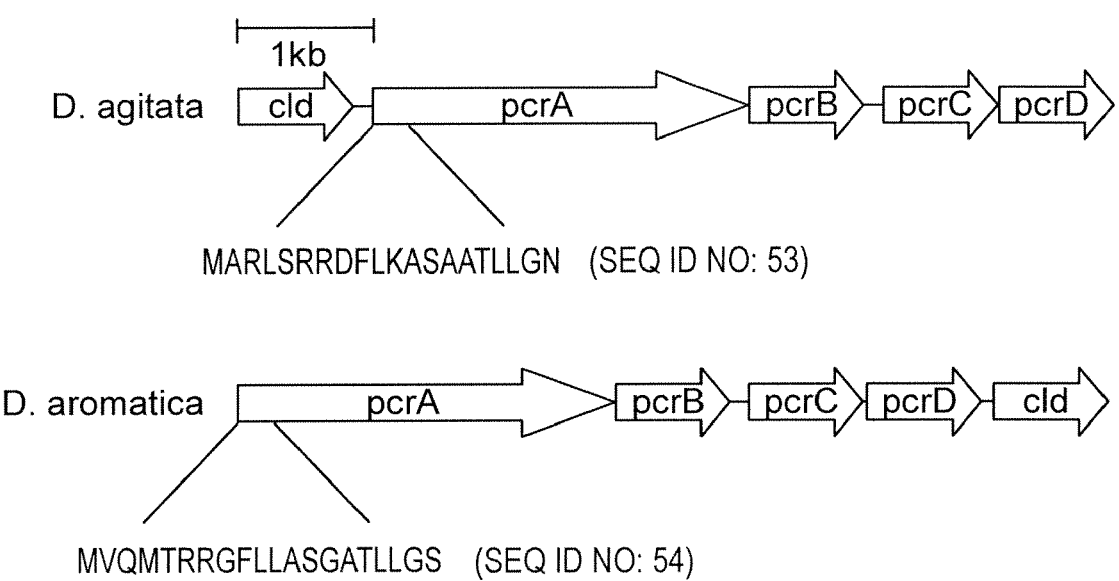
FIG. 1. Diagram of the pcrABCD genes of *D. agitata* and *D. aromatica*. The N-terminal sequences of PcrA are indicated, and the twin-arginine motif is in boldface type.

There are significant environmental problems associated with the presence of perchlorate in the ground water and soil compositions of areas where there has previously been significant activities from the aerospace, munitions, and fireworks industries. These industries have produced significant quantities of ammonium perchlorate and the unchecked disposal of this compound over the last 5 decades has resulted in the contamination the ground and surface waters throughout the United States and other countries (Renner et al., Environ. Sci. Technol. News 32:210A, 1998). Remediation of soils and water to remove the perchlorate contaminants has typically involved resin-based ion exchange chromatography, which is an inefficient method because of the bulk of resin required and the fact that the perchlorate-loaded resin ultimately must be disposed.

Biological methods for remediation or clean-up of the environment are compelling in that they employ natural organisms. Microorganisms have been used to clean-up oil spills, sewage effluent, chlorinated solvents, pesticides and the like. The ability of microorganisms to remove the contaminants from a contaminated site is nature's way of cleaning-up the environment. In the present application, there are provided methods and compositions for determining the presence and efficacy of one such set of microorganisms.

DPRB are excellent microbial bioremediators in that they are able to live in a diverse range of environments and are able to metabolize (per)chlorate. As such, natural attenuation of (per)chlorate contaminants is of significant economic and environmental interest. The present invention specifically is directed to identification of the presence of these bacteria and compositions that may be used in the field to determine whether a given target site will undergo bioremediation naturally or whether additional intervention is required. As noted above and described in PCT application PCT/US2005/004657 (inventors Achenbach et al., filed Feb. 11, 2005, which is incorporated herein by reference in its entirety), chlorite dismutase is an enzyme useful for the identification of both chlorate and perchlorate reducing bacteria. Perchlorate reductase, and the compositions and methods described herein is useful for further identifying the bacteria that can be used in perchlorate bioremediative processes in that the methods and compositions of the present invention are suitable for specifically identifying perchlorate reducing bacteria to such a specificity level that they can be distinguished from chlorate reducing bacteria.

Metabolic primer sets have been applied to a variety of bioremediative studies for the detection of specific bacteria. For example, since many denitrifiers are able to degrade toluene and xylene, Braker and colleagues developed primer sets targeting two nitrate reductase genes that allowed for the qualitative detection of denitrifiers in the environment (Braker et al., Appl. Environ. Microbiol., 64:3769-3775, 1998). And while primers for the catechol 2,3-dioxygenase were used to detect bacteria capable of aerobically degrading benzene, toluene, and xylene, they were also used in quantitative PCR to show an increase in gene copy number after soil samples were amended with petroleum (Mesearch et al., Appl. Environ. Microbiol. 66:678-683, 2000). In specific embodiments, the invention is directed to primers that are able to target a gene that is essential to the metabolic pathway of (per)chlorate reducing bacteria but do not target their close phylogenetic non-(per)chlorate-reducing relatives. These primers allow for the rapid, sensitive and inexpensive identification of presence of DPRB. Certain aspects of the invention are described in further detail herein below.

To date, chlorite dismutase and perchlorate reductase are the only enzymes in the perchlorate reduction pathway that have been isolated and characterized. The use of primers for the detection of chlorite dismutase have been described in PCT application PCT/US2005/004657 (inventors Achenbach et al., filed Feb. 11, 2005, which is incorporated herein by reference). Together with the chlorite dismutase gene, the gene for perchlorate reductase, and more particularly the pcrA gene (GenBank Accession No. AY180108), is a good candidate for the environmental detection of DPRB and can be used to particularly identify perchlorate reducing activity in a sample.

Just as studies have shown that chlorite dismutation is essential to the (per)chlorate reduction pathway (Bruce et al., Environ. Microbiol. 1:319-329., 1999; Coates et al., Appl. Environ. Microbiol. 65:5234-5241., 1999; van Ginkel et al., Arch. Microbiol. 166:321-326, 1996), the first step in microbial perchlorate reduction is the reduction of perchlorate ($ClO_4^-$) to chlorite ($ClO_2^-$) by the perchlorate reductase enzyme.

In the present invention there is provided a metabolic primer set targeting the perchlorate reductase gene (and more particularly the pcrA gene (GenBank Accession No. AY180108)). Such a primer set would be useful for the molecular detection of DPRB in the environment. However, the efficacy of this metabolic primer set is dependent upon regions of sequence conservation within the perchlorate reductase gene, information which is currently unavailable due to the paucity of gene sequences in the publicly available databases. The primers of the present invention are designed to universally detect this gene. Hence, this gene is the target nucleic acid for the methods of the present invention. As used herein, the term "target nucleic acid" or "nucleic acid target" refers to a particular nucleic acid sequence of interest. The "target" can exist in the presence of other nucleic acid molecules or within a larger nucleic acid molecule.

In the present invention, target nucleic acid is a sequence that is a perchlorate reductase gene and more particularly the pcrA gene, from any DPRB. The DPRB may be present in any sample, including soil samples, groundwater samples, isolated populations of DPRBs, cocktails of bacterial populations used in bioremediation processes and the like. The inventors have developed the primers of the present invention such that they hybridize to the pcrA gene from DPRB. The results and discussion of the studies leading to the identification of these primers is provided in the Examples.

It is particularly contemplated that the primers designed to identify the pcrA gene may be provided in kits or compositions which are designed to detect the chlorite dismutase gene, a gene that is unique to and required by all DPRB.

A. PRIMERS, OLIGONUCLEOTIDES AND PRODUCTION THEREOF

The following section provides a discussion of preferred primer and oligonucleotide compositions of the invention. The term "nucleic acid" as used herein refers to a linear sequence of nucleotides (bases) linked to one another by a phosphodiester bond between 3'-position of a pentose of one nucleotide and 5'-position of a pentose of another nucleotide. The term "polynucleotide" refers to a nucleic acid including a sequence of nucleotides more than about 100 bases. The term "oligonucleotide" refers to a short polynucleotide or a portion of polynucleotide including about 2-100 bases.

As used herein a "primer" refers to an oligonucleotide, which is capable of acting as a point of initiation of nucleic acid synthesis when the primer is placed under conditions in which synthesis of a primer extension product that is complementary to a nucleic acid strand is induced, i.e. in the presence of nucleotides and an inducing agent such as DNA polymerase and at a suitable temperature and pH. The primer may be a naturally occurring oligonucleotide or may be a purified restriction digest or produced synthetically. The oligonucleotide primers may be used, for example, in a PCR method as a primer for polymerization, in specific embodiments, the same primer may be in reverse transcription reaction in which the enzyme catalyzing the polymerization is a reverse transcriptase. Herein, oligonucleotides and primers of the invention may contain some modified linkages such as a phosphorothioate bond. The primers may also comprise a degenerate base, such as N base. Alternatively, one or more of the bases may be a universal base, such as e.g., hypoxanthine, as its ribo- or 2'-deoxyribonucleoside which is known for its ability to form base pairs with the other natural DNA/RNA bases. Nucleotide analog can be incorporated into the primers by methods well known in the art. The only requirement is that the incorporated nucleotide analog must serve to base pair with target polynucleotide sequences. For example, certain guanine nucleotides can be substituted with hypoxanthine, which base pairs with cytosine residues. Alternatively, adenine nucleotides can be substituted with 2,6-diaminopurine, which can form stronger base pairs than those between adenine and thymidine.

In exemplary embodiments of the present invention, primer sets targeting the perchlorate reductase gene were designed based on areas of amino acid and nucleotide sequence conservation in the pcrA gene.

The primers of SEQ ID NO:1 through 8 were developed based on the amino acid conservation of the pcrA sequence of the perchlorate reductase operon from *Dechloromonas agitata*, and *Dechloromonas aromatica*. Primers were synthesized by Integrated DNA Technologies, Coralville, Iowa. The primers include the following:

```
DPR.F SEQ ID NO:1:
GCNCCNCCNGTNGCNTT(T/C)ATG

DPR.R SEQ ID NO:2
(G/A)TC(G/A)TTNAC(T/C)TCNGC(G/A)TG(A/G/T)AT

DPR1.F SEQ ID NO:3
ACAGCGA(G/C/T)(G/C/T)TGCT(A/G/T)(A/G/T)TGCG

DPR1.R SEQ ID NO:4
(A/G/C)GCCGAAGG(A/G/C)A(A/G/T)AACCA(G/C/T)(A/G/C)

UPR.F SEQ ID NO:5
GA(T/C)CCNGCNCTNGA(G/A)GGNAA(G/A)

UPR.R SEQ ID NO:6
CCA(A/G/T)ATNGTNGT(T/C)TG(G/A)CA

UPR1.F SEQ ID NO:7
AGACCAC(G/C/T)ATCTGGACCTATGTC

UPR1.R SEQ ID NO:8
GG(A/G/C)A(A/G/T)AACCA(G/C/T)(A/G/C)TC(A/G/C)GAATA (T/C)A
```

Each of the above primers is a degenerate primer. Degenerate primers are useful for pulling out one part of a gene sequence when the gene sequence in related organisms is unknown. Degenerate primers are thus designed to match an amino acid sequence. Typically, one gathers sequences from a large range of organisms and translates them to amino acid sequence and aligns them. Based on these amino acid alignments, regions of the sequence that are highly conserved at the amino acid level are readily identified. These conserved regions become possible locations for degenerate primers. Preferably, at least 2 blocks of conserved amino acids should be present to enable the design of PCR primers. A further alignment can be done at nucleotide level if desired.

Typically, the conserved regions chosen as the basis for the primer design should be at least 5 amino acids in length, more preferably 6, 7, 8, 9, 10 or more amino acids in length. As such, the primers should be 20-30 mer in length and it is preferred that the minimum size is 20 bases in length (i.e., a 20 mer). In certain embodiments, the efficiency of the degenerate primers may be increased by adding an oligonucleotide tail to the degenerate primers on the 5' ends. This helps to increase the PCR efficiencies of these primers by increasing primer length and hence allows an increase in the annealing temperature. Although the tails do not help in the first few rounds of PCR when only the genomic template is being amplified, the tails do match in subsequent PCR cycles when the short PCR products containing the primers at each end are being amplified. Tails from commonly used restriction sites are particularly useful. For example a tail from an EcoRI site e.g., GCGCGGAATTC (SEQ ID NO:9) can be added to the 5' end of the degenerate primer. Another useful tail, GCGCGCAAGCTT (SEQ ID NO:10), from the HindIII restriction site could be added to the 5' end of a primer of the present invention.

Degeneracy of the primers depends on a multitude of factors including the template. 1000-10,000 fold degeneracy have been done. However the degeneracy can be lowered with the use of inosines for substituting 4 base wobbles instead of using all 4 base substitutions Thus, one or more of the "N" sequences in the above primers may be replaced with an inosine residue. To obtain the degeneracy of the primers, all the degeneracy values incorporated into the primer sequence are multiplied. Thus, other specific primers of the present invention include:

```
SEQ ID NO:11:
GC(I/N)CC(I/N)CC(I/N)GT(I/N)GC(I/N)TT(T/C)ATG

SEQ ID NO:12
(G/A)TC(G/A)TT(I/N)AC(T/C)TC(I/N)GC(G/A)TG(A/G/T)

AT

SEQ ID NO:13
GA(T/C)CC(I/N)GC(I/N)CT(I/N)GA(G/A)GG(I/N)AA(G/A)

SEQ ID NO:14
CCA(A/G/T)AT(I/N)GT(I/N)GT(T/C)TG(G/A)CA
```

The above specific primers for the detection of perchlorate reductase may be provided in remediation detection kits which comprise primers for the detection of chlorite dismutase. Exemplary primers for detection of chlorite dismutase include:

```
SEQ ID NO:15:
[5'-GA(A/G)CGCAA(A/G)(A/G)GNGCNGCNG(A/C)NGA(A/G)

GT-3']

SEQ ID NO:16:
[5'-TC(A/G)AA(A/G)TANGT(A/T/G)AT(A/G)AA(A/G)TC-3']

SEQ ID NO:17
[5'-T(C/T)GA(A/C/G)AA(A/G)CA(C/T)AAGGA(A/T/C)AA (A/C/G)GT-3']

SEQ ID NO:18:
[5'-GAGTGGTA(A/C/G)A(A/G)(C/T)TT(A/C/G)CG(C/T)

TT-3']

SEQ ID NO:19
[5'-GANCGNAANNGNGCNGCNGNNGANGT-3']

SEQ ID NO:20
[5'- TCNAANTANGTNATNAANTC-3']
```

Exemplary chlorite dismutase primers where one or more of the "N" residues are replaced with inosine include for example:

```
SEQ ID NO:21:
[5'-GA(A/G)CGCAA(A/G)(A/G)G(I/N)GCIGC(I/N)G(A/C)

(I/N)GA(A/G)GT-3']

SEQ ID NO:22:
[5'-TC(A/G)AA(A/G)TA(I/N)GT(A/T/G)AT(A/G)AA(A/G)

TC-3']

SEQ ID NO:23:
[5'-GA(I/N)CG(I/N)AA(I/N)(I/N)G(I/N)GC(I/N)GC(I/N)

G(I/N)(I/N)GA(I/N)GT-3']

SEQ ID NO:24:
[5'-TC(I/N)AA(I/N)TA(I/N)GT(I/N)AT(I/N)AA(I/N)

TC-3']
```

In the primers described herein, according to standard nomenclature "N" refers to any one of the bases A, C, G, or T and it is presented at the third "wobble" position of the nucleic acid codons. Those of skill in the art could modify these primers by fixing one or more of the "N" residues in any of the primers with a specific nucleotide. It is specifically contemplated that the individual sequences derived from the degenerate primers in which the "N" is a set base are specifically part of the present invention. Simply by way of example, SEQ ID NO:2, which is (G/A)TC(G/A)TTNAC(T/C)TCNGC(G/A)TG(A/G/T)AT, a 21 nucleotide-base primer may yield the primer: GTCGTTNACTTCNGCGTGAAT (SEQ ID NO:25) derived by fixing the "G/A" choice at position 1 of the oligonucleotide as "G," fixing the "G/A" choice at position 4 of the oligonucleotide as "G", fixing the "T/C" choice at position 10 of the oligonucleotide as "T", fixing the "G/A" choice at position 16 of the oligonucleotide as "G", fixing the "A\G\T" choice at position 19 of the oligonucleotide as "A". In like manner, the other permutations of the above degenerate primers also can be readily determined. Each of these permutations is particularly part of this invention and the specific sequences have not been written out as individual primer sequence, simply for the purposes of clarity and not because they are excluded from the written description.

One embodiment of the invention contemplates a library of primers that are generated from any one or more of the primers of SEQ ID NO:1 through SEQ ID NO:8 and SEQ ID NO:12 through SEQ ID NO:16, including permutations of each of these primers where one or other of the "N," "Y," "R," "B," "D," "V" residues in SEQ ID NO:1 through 8 is fixed as a specific nucleotide. In certain exemplary embodiments, it may be desirable to array such a library of primers on a sequencing chip or other nucleic acid microarray. The above library of primers is one which is for detection of perchlorate reductase. The library also may contain primers for the detection of chlorite dismutase, including all permutations of any one or more of the primers of SEQ ID NO:15 through SEQ ID NO:24.

Sequences of about 17 bases long should occur only once in the genome and, therefore, suffice to specify a unique target sequence. The primers of the present invention are typically of this size. As used herein, an oligonucleotide that "specifically hybridizes" to a given target nucleic acid (e.g., DNA; RNA) means that hybridization under suitably (e.g., high) stringent conditions allows discrimination of that target nucleic acid from other genes. Although shorter oligomers are easier to make, numerous other factors are involved in determining the specificity of hybridization. Both binding affinity and sequence specificity of an oligonucleotide to its complementary target increases with increasing length. It is contemplated that exemplary oligonucleotides of 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 or more base pairs can be prepared. In preferred aspects of the invention the oligonucleotide primers are between about 17 to about 50 bases in length and serve as primers in amplification reactions to amplify the sequence of any perchlorate reductase gene sequence from a DPRB sample.

The oligonucleotides may include the degenerate primers (which may be anywhere from 17 to 50 bases in length) but may also include 5' or 3' flanking regions or tails to facilitate amplification of the products. In particular, as discussed above, 5' tails on the degenerate primers are useful for increasing amplification efficiency. Thus, as used herein, the "primer" sequence is the degenerate primer discussed above, an oligonucleotide sequence may be the primer sequence alone, or it may be the primer sequence in addition to other nucleic acids.

The term "complementary" is used when defining a pair of nucleotide sequences, for example, a base pair of A/T or C/G, that match each other according to the base pairing rules. For example, a sequence of 5'-A-G-T-3' is complementary to a sequence of 3'-T-C-A-5'. Nucleotide sequences may be "partially" or "perfectly" complementary to one another so that they form partially matching base pairs or perfectly matching base pairs.

Methods for the production of primers are well known to those of skill in the art as routine synthesis techniques. For example, oligonucleotides can be synthesized chemically according to the solid phase phosphoramidite triester method described by Beaucage and Caruthers (1981), Tetrahedron Letts., 22(20):1859-1862, e.g., using a commercially available automated synthesizer, e.g., as described in Needham-VanDevanter et al. (1984) Nucleic Acids Res., 12:6159-6168. Synthesis of modified oligonucleotides (e.g., oligonucleotides comprising 2'-O-methyl nucleotides and/or phosphorothioate, methylphosphonate, or boranophosphate linkages, e.g., for use as nuclease resistant primers) are described in e.g., Oligonucleotides and Analogs (1991), IRL Press, New York; Shaw et al. (1993), Methods Mol. Biol. 20:225-243; Nielsen et al. (1991), Science 254:1497-1500; and Shaw et al. (2000) Methods Enzymol. 313:226-257. Detailed procedures for the phospho-triester and hydrogen phosphonate methods of oligonucleotide synthesis are described in the U.S. Pat. No. 4,458,066.

Oligonucleotides, including modified oligonucleotides (e.g., oligonucleotides comprising fluorophores and quenchers, 2'-O-methyl nucleotides, and/or phosphorothioate, methylphosphonate, or boranophosphate linkages) can also be ordered from a variety of commercial sources known to persons of skill. There are many commercial providers of oligo synthesis services, and thus, this is a broadly accessible technology. Companies such as The Midland Certified Reagent Company (www.mcrc.com), The Great American Gene Company (www.genco.com), ExpressGen Inc. (www.expressgen.com), QIAGEN (http://oligos.qiagen.com) and many others provide a readily available commercial service for the synthesis of oligonucleotide and as such the primers and oligonucleotides of the present invention may be commercially synthesized once the identity of the oligonucleotides is provided herein. The probes used herein were prepared by Integrated DNA Technologies, (Coralville, Iowa).

The present invention requires the use of a probe or primer pairs that are specific for perchlorate reductase and/or chlorite dismutase from a DPRB. To develop these probes or primers, one must first determine what genetic sequences are conserved between the many strains of DPRB. If one were to use a sequence derived from only a few strains, one would risk not detecting bacterial strain that had mutated slightly from this group.

The inventors compared the perA sequence from *D. agitata*, and *D. aromatica*, with other like sequences and looked for highly conserved nucleotide sequences. As discussed above, the design of degenerate primers typically employs an amino acid sequence of at least 5 amino acids, which would produce a 15-mer, however, it is preferred that the primers should be greater than or equal to 20 nucleotides in length. FIG. 1 describes the amino acid sequences identities of proteins that were compared.

A probe of the invention suitable to hybridize with a perchlorate reductase gene sequence will be at least 20 nucleotides in length and may be chosen from the entire length of the perchlorate reductase sequence. The probe should preferably have a GC content of approximately 50%. Similar considerations, of course are applicable to for example compositions for the detection of chlorite dismutase.

To derive primers from the perchlorate reducatase sequences, one must first choose sequences that when amplified would produce a DNA segment of sufficient length. An exemplary product length is a DNA segment of at least 100 nucleotides. If one wishes to visualize a PCR fragment on an electrophoretic gel, a smaller fragment would suffice. However, for optimum PCR amplification, a fragment of 100 nucleotides is still preferred. Preferably in both cases, the fragment should exceed 150 nucleotides.

The primer should be chosen so that the two primers are not complementary at the 3' ends. This situation would lead to a hybridization reaction between the primers before the primers hybridize to the substrate material. A complementary region of equal to or greater than 2 nucleotides will cause an unwanted primer hybridization. Preferably, there will be no complementary region at the 3' end. Also preferred are primers that do not have internal complementary segments that allow formation of hairpins.

B. AMPLIFICATION METHODS AND DETECTION OF PRODUCTS

The primers and oligonucleotide probes of the invention are used in methods of detecting the presence of (per)chlorate reducing bacteria. The presence of such bacteria is detected by determining the presence of the perchlorate reductase gene to which the degenerate primers of the present invention hybridize. The detection of the hybridized nucleotides is effected through the use of a polymerization chain reaction, a technique that is widely known in the field (U.S. Pat. Nos. 4,683,195; 4,683,202; and 4,800,159).

Nucleic acid amplification by template-directed, enzyme-dependent extension of primers is well known in the art. For example, amplification by the polymerase chain reaction (PCR) has been described. Details regarding various PCR methods, including, e.g., asymmetric PCR, reverse transcription-PCR, in situ PCR, quantitative PCR, real time PCR, and multiplex PCR, are well described in the literature. Details regarding PCR methods and applications thereof are found, e.g., in Sambrook et al., Molecular Cloning—A Laboratory Manual (3rd Ed.), Vol. 1-3, Cold Spring Harbor Laboratory, Cold Spring Harbor, N.Y. (2000); F. M. Ausubel et al. (eds.), Current Protocols in Molecular Biology, Current Protocols, a joint venture between Greene Publishing Associates, Inc. and John Wiley & Sons, Inc., (supplemented through 2002); Innis et al. (eds.), PCR Protocols: A Guide to Methods and Applications, Academic Press Inc., San Diego, Calif. (1990); J. P. V. Heuvel, PCR Protocols in Molecular Toxicology, CRC Press (1997); H. G. and A. Griffin, PCR Technology: Current Innovations, CRC Press (1994); Bagasra et al., (1997) In Situ PCR Techniques, Jossey-Bass; Bustin (2000) "Absolute quantification of mRNA using real-time reverse transcription polymerase chain reaction assays" Journal of Molecular Endocrinology 25:169-193; Poddar (2000) "Symmetric vs. asymmetric PCR and molecular beacon probe in the detection of a target gene of adenovirus" Molecular and Cellular Probes 14: 25-32; and Mackay et al. (2002) "Real-time PCR in virology" Nucleic Acids Res. 30:1292-1305, and references therein, among many other references.

Additional details regarding PCR methods, including asymmetric PCR methods, are found in the patent literature, e.g., U.S. Pat. No. 6,391,544 (May 21, 2002) to Salituro et al. entitled "Method for using unequal primer concentrations for generating nucleic acid amplification products"; U.S. Pat. No. 5,066,584 (Nov. 19, 1991) to Gyllensten et al. entitled "Methods for generating single stranded DNA by the polymerase chain reaction"; U.S. Pat. No. 5,691,146 (Nov. 25, 1997) to Mayrand entitled "Methods for combined PCR amplification and hybridization probing using doubly labeled fluorescent probes"; and U.S. patent application Ser. No. 10/281,054 (filed Oct. 24, 2002) by Beckman et al. entitled "Asymmetric PCR with nuclease-free polymerase or nuclease-resistant molecular beacons."

The PCR reaction is achieved by repeated cycles of denaturation, annealing for hybridizing a target sequence of a sample with a complementary primer, and polymerization using a thermally stable DNA polymerase to extend a DNA double helix from the hybridized primer. If no nucleotide primer hybridizes to the target nucleic acid, there is no PCR product. The PCR primer acts as a hybridization probe.

In brief, PCR typically uses at least one pair of primers (typically synthetic oligonucleotides). Each primer hybridizes to a strand of a double-stranded nucleic acid target that is amplified (the original template may be either single-stranded or double-stranded). A pair of primers typically flanks a nucleic acid target that is amplified. Template-dependent extension of the primers is catalyzed by a DNA polymerase, in the presence of deoxyribonucleoside triphosphates (typically dATP, dCTP, dGTP, and dTTP, although these can be replaced and/or supplemented with other dNTPs, e.g., a dNTP comprising a base analog that Watson-Crick base pairs like one of the conventional bases, e.g., uracil, inosine, or 7-deazaguanine), an aqueous buffer, and appropriate salts and metal cations (e.g., $Mg^{2+}$). The PCR process typically involves cycles of three steps: denaturation (e.g., of double-stranded template and/or extension product), annealing (e.g., of one or more primers to template), and extension (e.g., of one or more primers to form double-stranded extension products). The PCR process can instead, e.g., involve cycles of two steps: denaturation (e.g., of double-stranded template and/or extension product) and annealing/extension (e.g., of one or more primers to template and of one or more primers to form double-stranded extension products). The cycles are typically thermal cycles; for example, cycles of denaturation at temperatures greater than about 90° C., annealing at 50-75° C., and extension at 60-78° C. A thermostable enzyme is thus preferred.

Other suitable hybridization conditions for the PCR reaction will be well known to those of skill in the art. In certain applications, it is appreciated that lower stringency conditions may be required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results. Those of skill in the art will understand the salt concentrations and temperature parameters can be varied without departing from the nature of the invention.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C. Formamide and SDS also may be used to alter the hybridization conditions.

In specific preferred embodiments the annealing temperatures may range from 42° to 55° C., the MgCl$_2$ concentrations may be varied ranging from 1.0 to 3.0 mM, the primer amounts ranging from 15 to 60 μmol. In addition, the PCR methods were carried out in the presence of PCR additives, such as 0.25 mg of bovine serum albumin (BSA)/ml, 5% (vol/vol) dimethyl sulfoxide, and 1 M betaine. In the exemplary reaction mixtures employed in the present application, the reaction mixtures contained 1× Mg-free buffer, 1.0 to 3.0 mM MgCl$_2$, 200 μM of (each) deoxynucleoside triphosphates, 2.5 U of Taq polymerase (Sigma, St. Louis, Mo.), 1 μl of gDNA or environmental DNA, and nuclease-free double-distilled H$_2$O to a final volume of 50 μl. All components were purchased from Promega (Madison, Wis.) except for the polymerase.

In a particularly preferred PCR reaction, the following PCR conditions produced amplicons of the desired size using the forward and reverse primer set: 44° C. annealing temperature, 60 pmol (each) primer, 1.5 mM MgCl$_2$, and 0.25 mg of BSA/ml. In another exemplary reaction with a different primer set PCR conditions were 50° C. annealing temperature, 40 pmol (each) primer, 1.5 mM MgCl$_2$, and 0.25 mg of BSA/ml. Of course, the skilled artisan could vary these conditions and still achieve appropriate results in connection with the detection techniques of the present invention.

In the exemplary embodiments, the cycling parameters were as follows: reactions were initially heated to 94° C. for 2 min, followed by 30 cycles of 94° C. (1 min), annealing temperature (1 min), 72° C. (1 min), with a final 10-min 72° C. extension period. For touchdown cycling, the parameters consisted of a denaturation step at 94° C. for 1 min, a primer-annealing step for 1 min, and an extension step at 72° C. for 1 min. After 38 cycles, a final 10-min incubation was performed at 72° C. During the first 18 cycles, the annealing temperature was decreased by 1.0° C. every two cycles, starting at 59° C., until reaching a touchdown temperature of 50° C.

Automated thermal cyclers, including integrated systems for real time detection of product, are commercially available for performing PCR and other amplification reactions, e.g., the ABI Prism®7700 sequence detection system from Applied Biosystems, the iCycler iQ® real-time PCR detection system from Bio-Rad, or the DNA Engine Opticon® continuous fluorescence detection system from MJ Research, Inc. In particularly preferred embodiments, the PCR reactions were performed in a Perkin-Elmer 2400 thermocycler (Applied Biosystems, Foster City, Calif.).

Thermostable enzymes (including *Thermus aquaticus* Taq DNA polymerase, as well as enzymes substantially lacking 5' to 3' nuclease activity), appropriate buffers, etc. are also widely commercially available, e.g., from Clontech (Palo Alto, Calif., USA), Invitrogen (Carlsbad, Calif., USA), Sigma-Aldrich (St. Louis, Mo., USA), and New England Biolabs (Beverley Ma, USA). For example, thermostable polymerases lacking 5' to 3' nuclease activity are commercially available, e.g., Titanium™ Taq (Clontech, Palo Alto, Calif., USA, www.clontech.com), KlenTaq DNA polymerase (Sigma-Aldrich, St. Louis, Mo., USA, www.sigma-aldrich.com), Vent™ and DeepVent™ DNA polymerase (New England Biolabs, Beverley Ma, USA, www.neb.com), Tgo DNA polymerase and FastStart DNA polymerase (Roche, Indianapolis, Ind., USA www.roche-applied-science.com), ABgene's Thermoprime Plus DNA Polymerase (Rochester, N.Y., USA), SuperTaq or SuperTaq Plus™ (Ambion, Austin, Tx, USA), FideliTaq™ DNA Polymerase (USB Corp., Cleveland, Ohio, USA, www.usb.com), Tfl DNA Polymerase (Promega, Madison, Wis., www.promega.com), and PfuTurbo® Cx Hotstart DNA Polymerase (Stratagene, La Jolla, Calif., USA, www.stratagene.com).

While it is preferred that the amplification reaction is the PCR reaction, there are other suitable amplification techniques such as CPR (Cycling Probe Reaction), bDNA (Branched DNA Amplification), SSR (Self-Sustained Sequence Replication), SOA (Strand Displacement Amplification), QBR (Q-Beta Replicase), Re-AMP (Formerly RAMP), NASBA (Nucleic Acid Sequence Based Amplification), RCR (Repair Chain Reaction), LCR (Ligase Chain Reaction), TAS (Transorbtion Based Amplification System), and HCS (amplifies ribosomal RNA), all of which may be used as the amplification method.

In one embodiment of the invention, this assay comprises the steps of exposing a nucleic acid isolated from a biological sample to oligonucleotide primers chosen from the group consisting of SEQ ID NO:1 through SEQ ID NO:8 and SEQ ID NO: 11 through SEQ ID NO:14, including permutations of each of these primers where one or other of the "N," "Y," "R," "B," "D," "V" residues in SEQ ID NO:1 through 8 is fixed as a specific nucleotide. In specific embodiments, the PCR or transcription reaction is conducted directly on a bacterial lysate without isolating the nucleic acid therefrom. In other embodiments, nucleic acid is isolated from the sample, RNA is prepared therefrom and cDNA created from RNA. The reaction is allowed to incubate using PCR or other amplification or transcription conditions and the sample may then be examined for the presence of an amplification or other reaction product. In addition, these methods also could be performed using primer pairs specific for the cld gene (e.g., including all permutations of any one or more of the primers of SEQ ID NO:15 through SEQ ID NO:24.)

In PCR, the method begins with exposing a biological sample to a primer pair specific for the gene of interest, e.g., the perchlorate reductase gene or the cld gene. More particularly, nucleic acid is isolated from the biological sample and contacted with the primer pairs. In certain embodiments, RNA is prepared from the nucleic acids. RNA is preferably isolated from biological samples by adding a guanidinium solution. Other methods known in the art of isolating RNA would also be suitable.

To perform the method of the present invention, one must first select a probe and primer pair of the present invention and expose the perchlorate reductase cDNA to the primer pair. After amplification, the PCR product is detected. In certain embodiments, performing PCR with SEQ ID NO:1 and 2 alone is sufficient. In other preferred embodiments, however, it is contemplated that a nested PCR is performed in which the amplification product from the PCR reaction with SEQ ID NO:1 and 2 (or alternatively, SEQ ID NO:11 and 12) is used as a template for a second PCR reaction in which the probes are primers SEQ ID NO:3 and 4. Additional nested PCR reactions can be performed using the other primers described herein (including permutations of each of these primers where one or other of the "N," "Y," "R," "B," "D," "V" residues in SEQ ID NO:1 through 8 is fixed as a specific nucleotide).

In specific embodiments, it is contemplated that a reverse transcription reaction is carried out to determine the presence of perchlorate reductase mRNA in the sample. The reverse transcription reaction performed alone would be sufficient to identify the presence of the DPRB in the biological sample being tested. However, in other specific embodiments, it is contemplated that the reaction product from the reverse transcription reaction is employed as a template for a further PCR reaction in which a pair of primers described herein are used. Thus, in certain embodiments, it is contemplated that a method is carried out in which a reverse transcription reaction is carried out using a primer selected from the group consisting of SEQ ID NO:1 through SEQ ID NO:8 and SEQ ID NO:11 through SEQ ID NO:14 (including permutations of each of these primers where one or other of the "N," "Y," "R," "B," "D," "V" residues in SEQ ID NO:1 through 8 is fixed as a specific nucleotide). In yet another embodiment, a contemplated method involves performing such a reverse transcription reaction, isolating the product of the reaction and using it as a template for a PCR reaction using a pair of primers selected from the group consisting of SEQ ID NO:1 through SEQ ID NO:8 and SEQ ID NO:11 through SEQ ID NO:14 (including permutations of each of these primers where one or other of the "N," "Y," "R," "B," "D," "V" residues in SEQ ID NO:1 through 8 is fixed as a specific nucleotide).

In performing the reverse transcription, once RNA is isolated from the biological sample, and exposed to reverse transcriptase enzyme and deoxyribonucleotides so that a cDNA molecule may be created that corresponds to the initial RNA molecule. Exemplary reverse transcriptases that may be used include, but are not limited to AMV Reverse Transcriptase (GEHealthcare and Amersham Biosciences, Piscataway, N.J., USA, AMV Reverse Transcriptase (Stratagene, La Jolla, Calif., USA www.stratagene.com), AMV RT (CHIMERx, Madison, Wis. USA, www.chimerx.com), cloned AMV Reverse Transcriptase (Invitrogen, Carlsbad, Calif., USA www.invitrogen.com), AMV Reverse Transcriptase (Ambion, Austin Tx, USA, www.ambion.com), AMV Reverse Transcriptase (www.MJResearch.com), AMV Reverse Transcriptase (Promega, Madison Wis., USA www-.promega.com), and Reverse Transcriptase AMV (Roche, Indianapolis, Ind., USA, www.roche-applied-science.com)

For a PCR reaction, one would choose to use a pair of primers and examine the final product for presence of a PCR amplification product. This examination could involve examining the products of the reaction on an electrophoretic gel and determining whether an amplified product of the appropriate size had been created. One of skill in the art of molecular biology will be aware of many protocols designed to optimize PCR reactions. Particularly useful protocols are described in PCR Protocols, Ed. M. Innis, et al. Academic Press, San Diego.

The PCR reaction can be coupled to, for example, an ELISA detection procedure. In such a procedure, one would anchor the PCR amplification product to a solid support and examine the support for the presence of the PCR product. This procedure could be done in several ways. For example, one first attaches the amplified product to a solid support, such as a microtiter dish. For example, a streptavidin-coated plate may be provided. One of the selected primers may be attached to a biotin molecule so that an amplification product will be labelled with biotin and bind to the streptavidin plate. This is yet a further use of the probes of the present invention in that the primers/probes of the invention can be used to "fish-out" and identify/isolate the amplified product. For such embodiments, hybridization conditions discussed above could be used. In these embodiments, the plate and product are then exposed to perchlorate-reductase-specific oligonucleotide probe of the invention containing a segment of the perchlorate-reductase sequence. This probe is attached to a marker enzyme, such as horseradish peroxidase (HRP), which may be detected via its enzymatic properties.

In another method, one would attach a protein molecule capable of binding to the solid support, e.g., BSA, to an oligonucleotide probe/primer of the present invention. The plate is then coated with these protein-attached oligonucleotides, and these oligonucleotides are available to hybridize with an amplified product. This amplified product is preferably attached to a label molecule, such as biotin, that is capable of being detected. In one embodiment, the biotin-labelled PCR product may be complexed to a streptavidin-horse radish peroxidase conjugate. One may then detect this complex with the appropriate substrate.

The amplified products can be identified using various techniques, for example, by inserting a labeled nucleotide into the strands amplified using labeled primers. Examples of standard labeling materials include, but are not limited to, radioactive materials ($^{32}P$, $^{35}S$, $^{131}I$, $^{125}I$, $^{14}C$, $^{3}H$), fluorescent labels (e.g., fluorescein, Texas Red, rhodamine, BODIPY, resorufin or arylsulfonate cyanines, digoxygenin, horseradish peroxidase, alkaline phosphatases, acridium ester), chemiluminescent labels (e.g., acridinium esters), biotin, and jack beam urease. Furthermore, the PCR products obtained using non-labeled primers can be identified by combination of gel separation using electrophoresis and a dye-based visualizing technique. Thus it is particularly contemplated that the primers of the invention are labeled with such detectable labels.

A label or quencher can be incorporated into the primers and probes of the invention during oligonucleotide synthesis by using a specialized phosphoramidite including the label or quencher, or a modified base phosphoramidite including an alkyl spacer can be incorporated during oligonucleotide synthesis and the label or quencher can be linked to the spacer after synthesis is complete. As a specific example, fluorescein can be incorporated at the 5' end of a probe of the invention by using a fluorescein phosphoramidite in the last step of the synthesis. As another specific example, a modified T including a C6 spacer with a primary amino group can be incorporated into the oligonucleotide, and a succinimidyl ester of 4-(4'-dimethylaminophenylazo)benzoic acid (DABCYL) can be attached to the primary amino group. (Such modified phosphoramidites are commercially available, e.g., Amino-Modifier C6 dT from Glen Research.) Similarly, 4-dimethylaminophenylazophenyl-4'-maleimide (DABMI) can be used when the site of attachment is a sulphydryl group.

As other examples, fluorescein can be introduced into oligonucleotides, either by using a fluorescein phosphoramidite that replaces a nucleoside with fluorescein, or by using a fluorescein dT phosphoramidite that introduces a fluorescein moiety at a thymidine ring via a spacer. To link a fluorescein moiety to a terminal location, iodoacetoamidofluorescein can be coupled to a sulphydryl group. Tetrachlorofluorescein (TET) can be introduced during automated synthesis using a 5'-tetrachloro-fluorescein phosphoramidite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonylchloride of Texas red coupled to a sulphydryl group.

C. ASSAYS AND KITS

In one embodiment, the present invention is an assay for the presence of DPRB in a sample. In other embodiments, this assay may be combined in an assay for at least one other microorganism that can effect remediation. For example, in contaminated soils or water samples, it may be desirable to remove the (per)chlorate contamination using DPRB and to remove contamination of other contaminants using other reclamation and/or bioremediation techniques. Preferably, such assays examine a biological sample for presence or absence of the appropriate contaminants as well as microorganisms that can remove such contaminants.

The perchlorate reductase gene may be derived from any DPRB. The presence of this gene in a sample being tested is indicative of the sample possessing bacteria that will effect remediation of the sample and clean-up any (per)chlorate contamination thereof. The organisms from which the perchlorate reductase gene may be detected and whose presence is desired in the samples to effect bioremediation of a (per) chlorate contaminated sample include, but are not limited to, *Dechloromonas* spp., *Azoarcus* spp., *Dechlorospirillum* spp., *Dechloromarinus* spp., *Ideonella* spp., *Magnetospirillum* spp., *Pseudomonas* spp., *Rhodocyclus* spp., *Rhodospirillum* spp., *Azospirillum* spp., *Wolinella* spp., and *Xanthomonas* spp. Exemplary bacteria from these species include for example, *Dechloromonas agitata*, *Dechloromonas aromatica*, *Azospira suillum*, *Dechlorospirillum anomalous*, *Dechloromarinus chlorophilus*, and *Ideonella dechloratans*. These are merely exemplary DPRBs and many others will be known to those of skill in the art.

In another embodiment, the present invention provides a kit for assaying DPRB present in a sample. In a preferred embodiment, the kit comprises a pair of primers selected from SEQ ID NO:1 through SEQ ID NO:8 and SEQ ID NO:11 through SEQ ID NO:14 (including permutations of each of these primers where one or other of the "N," "Y," "R," "B," "D," "V" residues in SEQ ID NO:1 through 8 is fixed as a specific nucleotide). In another embodiment, the kit comprises at least one additional pair of primers designed to amplify a 16S RNA from one or more of the organisms indicated above. In a more preferred embodiment of the kit, the kit additionally comprises primers SEQ ID NO:1 or SEQ ID NO:11 and SEQ ID NO:2 or SEQ ID NO:12; in another embodiment, the kit comprises primers SEQ ID NO:3 and SEQ ID NO:4, is still a further embodiment, the kit comprises primers of SEQ ID NO:5 or SEQ ID NO:13 and SEQ ID NO:6 or SEQ ID NO:14; in yet a further embodiment the kit comprises in another embodiment, the kit comprises primers SEQ ID NO:7 and SEQ ID NO:8. Kits that comprise SEQ ID NO:1, SEQ ID NO:2; SEQ ID NO:3 and SEQ ID NO: 4 are specifically contemplated. In some kits the perchlorate reductase primers are provided with primers that detect chlorite dismutase. Specific such chlorite dismutase detection primers include but are not limited to SEQ ID NO:15 through SEQ ID NO:24. Preferably, the primers of each SEQ ID NO are provided in separate containers.

In addition, the kits may comprise one or more enzymes for the PCR amplification and/or for the reverse transcription reactions. Thus, the kits optionally also includes one or more of: a polymerase (e.g., a polymerase having or substantially lacking 5' to 3' nuclease activity), a buffer, a standard template for calibrating a detection reaction, instructions for extending the primers to amplify at least a portion of the target nucleic acid sequence or reverse complement thereof, instructions for using the components to amplify, detect and/or quantitate the target nucleotide sequence or reverse complement thereof, or packaging materials. The kits may also preferably include the deoxyribonucleoside triphosphates (typically dATP, dCTP, dGTP, and dTTP, although these can be replaced and/or supplemented with other dNTPs, e.g., a dNTP comprising a base analog that Watson-Crick base pairs like one of the conventional bases, e.g., uracil, inosine, or 7-deazaguanine), an aqueous buffer, and appropriate salts and metal cations (e.g., $Mg^{2+}$)

The kit may comprise a solid support on which the present the primers. Alternatively, the primers may be bound to a solid support. The solid support may be any support that is typically used to in nucleic acid preparation and analysis. Such supports include, but are not limited to plastic, glass, beads, microtiter plates. Indeed, glass, plastics, metals and the like are often used, and the nucleic acid amplification method of the present invention can be used irrespective of the type of the substrate. In some aspects, the probes of the invention may be effectively used for assaying nucleic acid molecules using a DNA chip or DNA micro-array where a large number of DNA probes are immobilized on a flat substrate. Furthermore, other than the flat DNA chips, the nucleic acid assay method using beads on which DNA probes are immobilized has become popular in recent years, and the nucleic acid amplification method of the present invention is also applicable to preparation of a sample in the nucleic acid detection method using the DNA probes immobilized on the surfaces of beads.

The primers in the kits may be provided in the form of nucleic acid-based arrays. Microarray chips are well known to those of skill in the art (see, e.g., U.S. Pat. Nos. 6,308,170; 6,183,698; 6,306,643; 6,297,018; 6,287,850; 6,291,183, each incorporated herein by reference). These are exemplary patents that disclose nucleic acid microarrays and those of skill in the art are aware of numerous other methods and compositions for producing microarrays. The term "microarray" refers to an ordered arrangement of hybridizable array elements. The array elements are arranged so that there are preferably at least two or more different array elements, more preferably at least 20 array elements, and more preferably at least 100 array elements, on a 1 $cm^2$ substrate surface. The hybridization signal from each of the array elements is individually distinguishable a specific location, or address of the probe. In a preferred embodiment, the array elements comprise polynucleotide primers of the present invention.

In addition to the above, the kits may comprises components as standards. For example, the kits may comprise known perchlorate reductase or a chlorite dismutase sequences such that the signal received from the environmental/biological sample can be compared with that received from the standard to ensure the integrity of the assay components and conditions.

D. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Growth conditions. *Dechloromonas agitata* and *Dechloromonas aromatica* were grown both anaerobically and aerobically in basal media as previously described (Bender et al., Appl. Environ. Microbiol. 68:4820-4826, 2002; Bruce et al., Environ. Microbiol., 1:319-329, 1999). For anaerobic cultures, 10 mM acetate and 10 mM perchlorate, chlorate, or nitrate were used as the electron donor and the electron acceptor, respectively. For aerobic growth, (per)chlorate was omitted and oxygen was added to the same basal media. To check for induction under aerobic conditions, 1 mM sodium nitrate, chlorate, or perchlorate was added to aerobically grown cultures.

Nucleic acid extraction and mutant construction. Both genomic DNA and RNA were extracted as previously described using a PUREGENE DNA isolation kit (Gentra Systems Inc., Minneapolis, Minn.) and the RNAwiz reagent (Ambion, Austin, Tex.), respectively (Bender et al., Appl. Environ. Microbiol. 68:4820-4826, 2002). A pcrA mutant of *D. aromatica* was constructed by replacement of the pcrA gene with a tetracycline resistance cassette. Briefly, a region upstream of the pcrA start codon and a region downstream of the pcrA stop codon were PCR amplified and inserted on either side of a 1.6-kb pBR322 tetracycline resistance cassette that had been cloned into a suicide vector. This construct was used to transform *D. aromatica* cells; double-recombination mutants in which the pcrA gene on the chromosome had been replaced with the resistance cassette were verified by PCR amplification.

Sequence analysis. DNA sequences obtained from *D. agitata* lambda library screening (Bender et al., Appl. Environ. Microbiol. 68:4820-4826, 2002), as well as the complete genome sequence of *D. aromatica*, obtained courtesy of the Joint Genome Institute (http://www.jgi.doe.gov), were subjected to BLAST analysis (Altschul et al., Nucl. Acid Res. 25:3389-3402, 1997). DNA sequence manipulations were performed using the MacVector sequence analysis software for the Macintosh (version 7.0; Oxford Molecular) and the Se—Al sequence alignment editor, v. 1.0 (A. Rambaut, University of Oxford).

Hybridization analyses. Northern blotting was performed using the Northern-Max-Gly glyoxal-based system (Ambion) as previously described (Bender et al., Appl. Environ. Microbiol. 68:4820-4826, 2002). For all growth conditions, 5 µg of total RNA was loaded onto a 1% (wt/vol) glyoxal agarose gel. Following RNA transfer, the blot was hybridized at 50° C. in Easyhyb hybridization solution (Roche Applied Science, Indianapolis, Ind.) with a digoxigenin-labeled probe corresponding to 436 bp in the 5' half of the *D. agitata* pcrA gene. This probe was generated via PCR at an annealing temperature of 55° C. with the following primers: PR-750F (5'-CGCGAAGGTAGTCAGCATCT-3'; SEQ ID NO:26) and PR-1185R (5'-TCCATCCTGCAACTTGACCT-3'). For DNA slot blotting, genomic DNAs from known DPRB and non-perchlorate-reducing close relatives were blotted as previously described (Bender et al., Appl. Environ. Microbiol. 68:4820-4826, 2002). The blot was hybridized at 45° C. with the same perchlorate reductase probe used in the Northern blot analysis.

Phylogenetic analysis. Protein sequences from the α-subunits of known DMSO reductase enzymes were obtained from the GenBank database (Bensen et al., Nucleic Acid Res. 32:D35-D40, 2004) and aligned with the α-subunit of perchlorate reductase using the CLUSTALW 1.82 program (Thompson et al., Nucl. Acid Res. 22:4773-4680, 1994). A phylogenetic tree was constructed with the PAUP* v 4.0 program (D. L. Swofford, Sinauer Associates) using distance as the criterion and neighbor joining as the drawing method.

Figure 7:
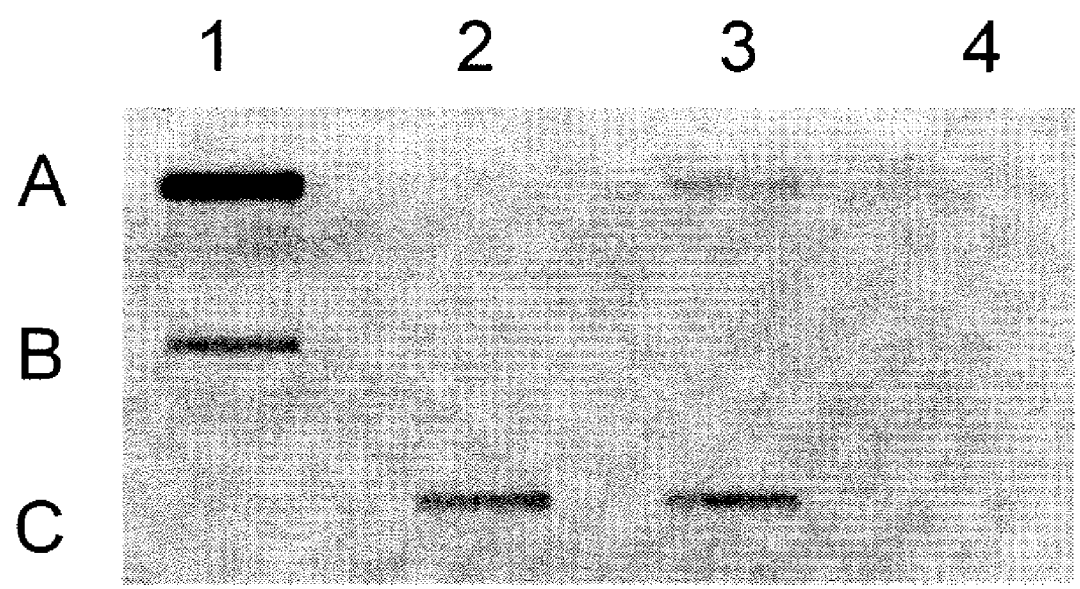
FIG. 7. Slot blot hybridization of genomic DNAs from DPRB and non-perchlorate-reducing close relatives of DPRB using the *D. agitata*, pcrA probe. A total of 250 ng of genomic DNA was loaded for each strain. Row A (left to right): 1, *D. agitata*; 2, *R. tenuis*; 3, *D. aromatica*; 4, *Dechloromonas* sp. strain JJ. Row B: 1, *D. anomolous* strain WD; 2, *M. magnetotacticum*; 3, *Pseudomonas* sp. strain PK; 4, *P. stutzeri*. Row C: 1, *D. chlorophilus* strain NSS; 2, *A. suillum*; 3, *Dechloromonas* sp. strain LT-1; 4, *I. dechloratans*. *D. agitata*, *D. aromatica*, *D. anomalous*, *A. suillum*, and *Dechloromonas* sp. strain LT-1 are capable of perchlorate reduction; *Pseudomonas* sp. strain PK, *D. chlorophilus* strain NSS, and *I. dechloratans* are capable of only chlorate reduction.

GenBank accession numbers. The GenBank accession numbers for the *D. agitata* perchlorate reductase genes are as follows: pcrA, AY180108; pcrB, AY953269; pcrC, AY953270; and pcrD, AY953271. The accession numbers for the protein sequences shown in FIG. 2 are as follows: SerB, Q9S1G9; ClrB, P60069; EbdB, CAD58340; DdhB, AAN46633; and NarH, CAD22070. The accession number for the *Nitrosomonas europaea* cytochrome $c_{554}$ shown in FIG. 3 is NP_842334. The GenBank accession numbers for the 16S rRNA gene sequences of the organisms shown in FIG. 7 are as follows: *D. agitata*, AF047462; *Rhodocyclus tenuis*, D16209; *D. aromatica*, AY032610; *Dechloromonas* sp. Strain JJ, AY032611; *Dechlorospirillum anomolous* strain WD, AF170352; *Magnetospirillum magnetotacticum*, Y10110; *Pseudomonas* sp. strain PK, AF170358; *Pseudomonas stutzeri*, U26415; *Dechloromarinus chlorophilus* strain NSS, AF170359; *Azospira suillum*, AF170348; *Dechloromonas* sp. strain LT-1, AY124797; and *I. dechloratans*, X72724.

TABLE 1

BLAST analysis of the pcrABCD translation products

| Gene | GenBank BLAST hit | % Amino acid identity |
|---|---|---|
| pcrA | CAD22069, *Haloarcula marismortui* nitrate reductase α-subunit (NarG) | 41 |
| | CAF21906, *Haloferax mediterranei* nitrate reductase α-subunit (NarG) | 40 |
| | AAN46632, *Rhodovulum sulfidophilum* dimethyl sulfide dehydrogenase α-subunit (DdhA) | 34 |
| | Q9S1H0, *Thauera selenatis* selenate reductase α-subunit (SerA) | 33 |
| | P60068, *Ideonella dechloratans* chlorate reductase α subunit (ClrA) | 33 |
| pcrB | Q9S1G9, *Thauera selenatis* selenate reductase β-subunit (SerB) | 54 |
| | P60069, *Ideonella dechloratans* chlorate reductase β-subunit (ClrB) | 54 |
| | CAD58340, *Azoarcus* sp. strain EbN1 ethylbenzene dehydrogenase β-subunit (EbdB) | 53 |
| | AAN46633, *Rhodovulum sulfidophilum* dimethyl sulfide dehydrogenase β-subunit (DdhB) | 52 |
| pcrC | NP_842334, *Nitrosomonas europaea* cytochrome $c_{554}$ precursor | 49 |
| pcrD | Q9S1G8, *Thauera selenatis* selenate reductase (SerD) | 35 |
| | AAN46634, *Rhodovulum sulfidophilum* dimethyl sulfide dehydrogenase δ-subunit (DdhD) | 29 |
| | CAD58338, *Azoarcus* sp. strain EbN1 ethylbenzene dehydrogenase δ-subunit (EbdD) | 25 |
| | CAD22073, *Haloarcula marismortui* nitrate reductase molybdenum chaperone (NarJ) | 25 |

Example 2

Results And Discussion

Identification of pcrABCD genes. In the course of characterizing the chlorite dismutase (cld) gene (Bender et al., Appl. Environ. Microbiol. 68:4820-4826, 2002), we identified a proximal operon putatively encoding perchlorate reductase in the genomes of two DPRB, *D. agitata* and *D. aromatica*. The orientation of the perchlorate reductase genes was the same in both DPRB with exception of the position of the cld gene (FIG. 1). BLAST analysis of the open reading frames, designated pcrABCD, revealed amino acid similarities to subunits of microbial nitrate reductase, selenate reductase (serABDC), dimethyl sulfide dehydrogenase (ddhABDC), ethylbenzene dehydrogenase (ebdABCD), and chlorate reductase (clrABDC), all of which are members of the type II DMSO reductase family (Table 1). While the serABDC (Kengen et al., J. Bacteriol 181:6706-6711, 1999), ddhABDC (Kisker et al., Annu Rev. Biochem., 66:233-267, 1997), and clrABDC (Danielsson-Thorell, Appl. Environ. Microbiol. 69:5585-5592, 2003) operons all have the same gene order, the pcrABCD operon mimics the ebdABCD (McEwan et al., Geomicrobiol., J., 19:3-21, 2002) operon arrangement.

pcrA. Translational analysis of the 2,784-bp pcrA gene identified a molybdopterin-binding domain (data not shown), as well as a twin-arginine signal motif, (S/T)RRXFLK (FIG. 1). Previous studies have suggested that the twin-arginine motif tags proteins involved in electron transfer reactions, whose prosthetic groups are formed in the cytoplasm prior to secretion, for transport to the periplasm via Sec-independent transport (Tat pathway) (Berks et al., Mol. Microbiol., 35:260-274, 2000). This motif is also commonly found in electron transfer proteins possessing a pterin molybdenum cofactor and iron-sulfur (Fe—S) centers (Berks, Mol. Microbiol., 22:393-404, 1996). Since the perchlorate reductase of GR-1 was located in the periplasm and contained molybdenum and Fe—S centers (Kengen et al., J. Bacteriol 181:6706-6711, 1999), the presence of this signal peptide further supports identification of the pcrA gene as the gene encoding the α-subunit of the perchlorate reductase. In addition, the calculated molecular mass of the PcrA subunit is 105 kDa, a value that corresponds well to the 95 kDa predicted for the α-subunit of the purified perchlorate reductase from GR-1 (Kengen et al., J. Bacteriol 181:6706-6711, 1999)

pcrB. The inferred amino acid sequence of the 1,002-bp pcrB gene product indicated the presence of four cysteine-rich clusters for Fe—S center binding, a feature shared with β-subunits of type II DMSO reductase enzymes (FIG. 2). This cysteine organization has been shown to bind one 3Fe-4S center and three 4Fe-4S centers in both dimethyl sulfide dehydrogenase (McDevitt et al., Biochemistry, 41:15234-15244, 2002) and nitrate reductase (Jormakka et al., Structure, 12:95-104, 2004) β-subunits. Based on data for the β-subunit of the *Escherichia coli* nitrate reductase (Guigliarelli et al., Biochemistry, 35:4828-4836, 1996), these Fe—S centers may be responsible for electron transfer to the molybdopterin-containing α-subunit of perchlorate reductase.

The predicted N-terminal amino acid sequences of the *D. agitata* and *D. aromatica* PcrB proteins were aligned with the N-terminal sequence of purified PcrB from GR-1 (Kengen et al., J. Bacteriol 181:6706-6711, 1999). This alignment reinforced the identity of the pcrB gene (FIG. 2). The predicted *D. agitata* PcrB N terminus contained 10 of the 18 residues and the predicted *D. aromatica* PcrB sequence contained 16 of the 18 residues reported for the purified perchlorate reductase β-subunit from strain GR-1. Since no signal sequence was detected, the β-subunit of perchlorate reductase is likely translocated with the β-subunit in a manner similar to that proposed for selenate reductase (Krafft et al., DNA Seq., 10:365-377, 2000), dimethyl sulfide dehydrogenase (McDevitt et al., Mol. Microbiol., 44:1575-1587, 2002), and chlorate reductase (Danielsson-Thorell, Appl. Environ. Microbiol. 69:5585-5592, 2003). The calculated molecular mass of the PcrB subunit was 37 kDa, a value similar to the 40 kDa reported for the β-subunit of the purified perchlorate reductase from GR-1 (Kengen et al., J. Bacteriol 181:6706-6711, 1999).

pcrC. Although a γ-subunit was not detected in the enzyme analysis of the perchlorate reductase from strain GR-1, a third cytochrome-type subunit responsible for connecting the reductase to the membrane was believed to have been lost during purification of the enzyme (Kengen et al., J. Bacteriol 181:6706-6711, 1999). This observation was borne out by our identification of a 711-bp open reading frame immediately downstream of the pcrB gene in both *D. aromatica* and *D. agitata*, whose product exhibited sequence similarity to cytochrome $c_{554}$ from *N. europaea* (Table 1). Amino acid alignment indicated that PcrC also has the unique tetraheme organization of cytochrome $c_{554}$ from *N. europaea* (Iverson et al., Nat. Struct. Biol., 5:1005-1012, 1998) (FIG. 3). The lack of amino acid sequence similarity between PcrC (ca. 25 kDa) and other type II DMSO reductase γ-subunits was not surprising due to the overall sequence diversity noted in the SerC, EbdC, DhdC, and ClrC subunits (Danielsson-Thorell, Appl. Environ. Microbiol. 69:5585-5592, 2003).

Figure 4:
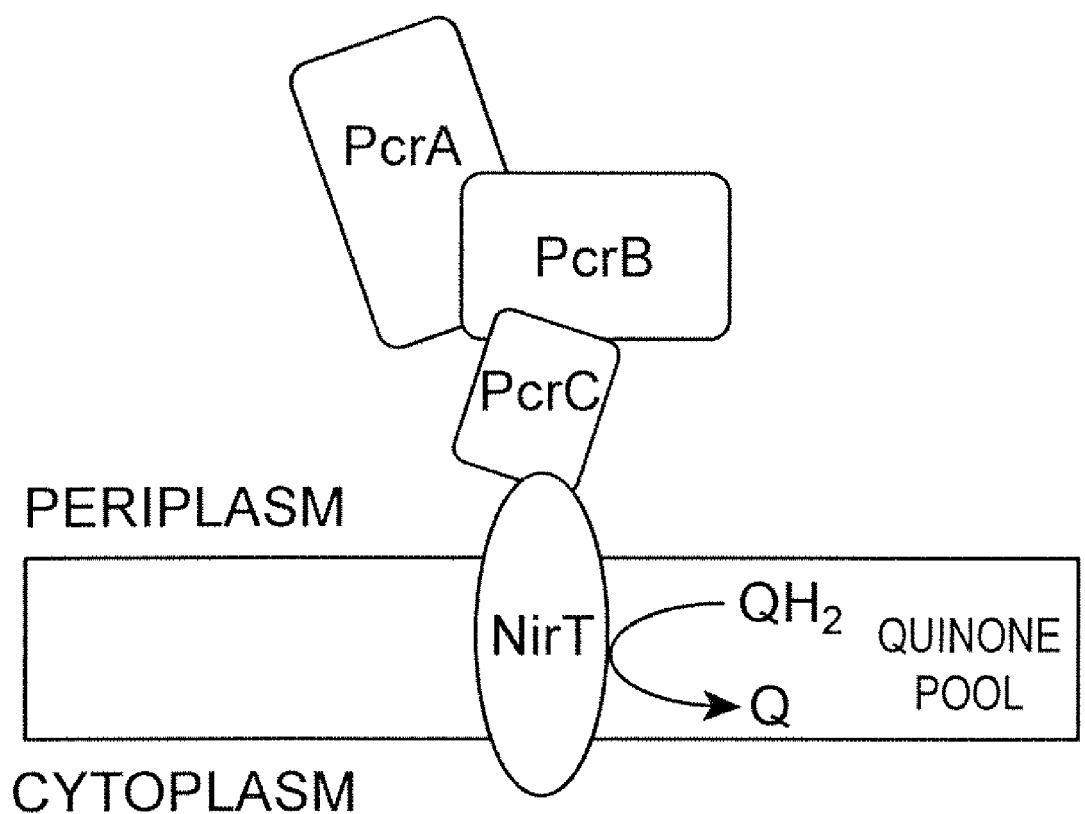
FIG. 4. Predicted model for electron transfer during (per) chlorate reduction. Electrons from a quinone pool are transferred from the membrane via a NirT-type cytochrome to the PcrABC reductase. While PcrD is absent from the functional enzyme, this protein is predicted to be involved in enzyme assembly.

The ProteinPredict server (http://cubic.bioc.columbia.edu/pp/) indicated that the pcrC translation product is not a membrane-bound protein and therefore cannot link the PcrAB complex to the membrane. However, further analysis of the *D. aromatica* genome revealed the presence of a NirT-type cytochrome gene downstream of the chlorite dismutase gene. The cytochrome may link the periplasmic PcrABC reductase to the membrane quinol pool (FIG. 4). Membrane-bound NirT-type cytochromes have been shown to shuttle electrons to the periplasmic nitric reductase of *P. stutzeri*, the $Fe^{3+}$ and fumarate reductases of *Shewanella putrefaciens*, and the periplasmic nitrate reductase (McEwan et al., Geomicrobiol., J., 19:3-21, 2002; Richardson, Microbiology 146:551-571, 2000; Roldan et al., J. Biol. Chem., 273:28785-28790, 1998). The model predicted for perchlorate reduction (FIG. 4) differs from the model projected for selenate reduction (McEwan et al., Geomicrobiol., J., 19:3-21, 2002) by replacement of the $bc_1$ complex with a NirT-type cytochrome.

pcrD. Based on sequence identity with SerD, DdhD, EbdD, and NarJ, the final 675-bp pcrD gene likely encodes a system specific molybdenum chaperone protein (ca. 25 kDa) (Table 1). This finding is supported by the absolute requirement for molybdenum for active perchlorate reduction (Chaudhuri et al., Appl. Environ. Microbiol., 68:4425-2230, 2002). The SerD, DdhD, and EbdD proteins are believed to be involved in assembly of the mature molybdenum-containing selenate reductase, dimethyl sulfide dehydrogenase, and ethylbenzene dehydrogenase, respectively, prior to periplasmic translocation via the Tat pathway. However, these proteins are not believed to be parts of the active enzymes (Krafft et al., DNA Seq., 10:365-377, 2000, McDevitt et al., Mol. Microbiol., 44:1575-1587, 2002, Rabus et al., Arch. Microbiol., 178:506-516, 2002).

Expression and mutagenesis of pcrA. Both expression analysis and mutagenesis of the pcrA gene verified the identity of the pcrABCD operon. Northern analysis of *D. agitata* RNA indicated that there was pcrA gene expression in anaerobic perchlorate- and chlorate-grown cultures (data not shown). However, the presence of perchlorate, chlorate, or nitrate was not enough to induce pcrA expression in aerobic cultures and, as such, indicates the ability of oxygen to completely inhibit pcrA expression, as suggested by the previously documented inhibitory effects of oxygen on perchlorate reduction (Chaudhuri et al., Appl. Environ. Microbiol., 68:4425-2230, 2002, 22).

Figure 5A:
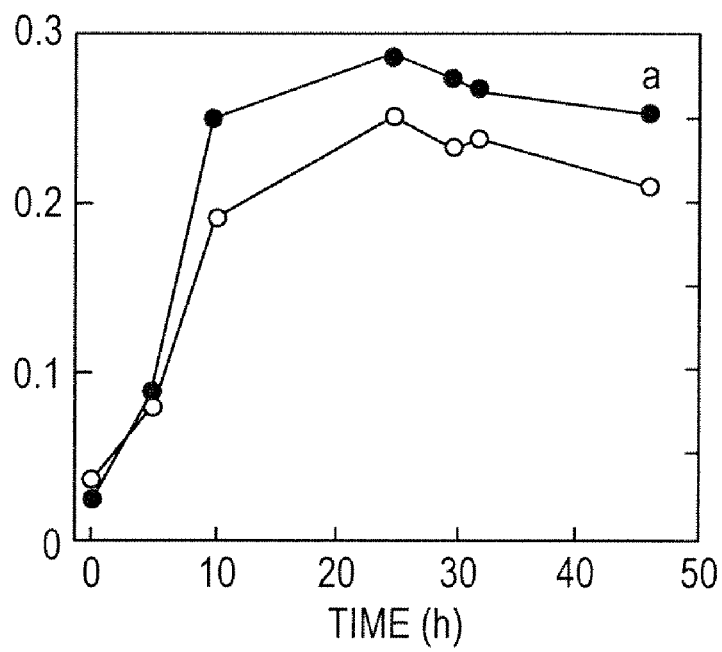
FIG. 5. Anaerobic growth of wild-type *D. aromatica* and pcrA mutant with nitrate (a), perchlorate (b), or chlorate (c) as the sole electron acceptor. F, wild-type growth; E, pcrA mutant growth. The data are averages for duplicate incubations.
Figure 5B:
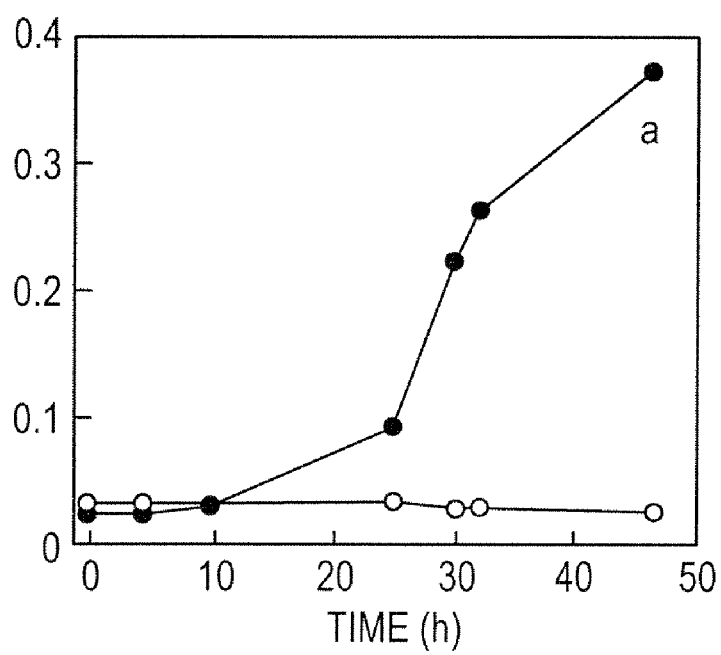
Figure 5C:
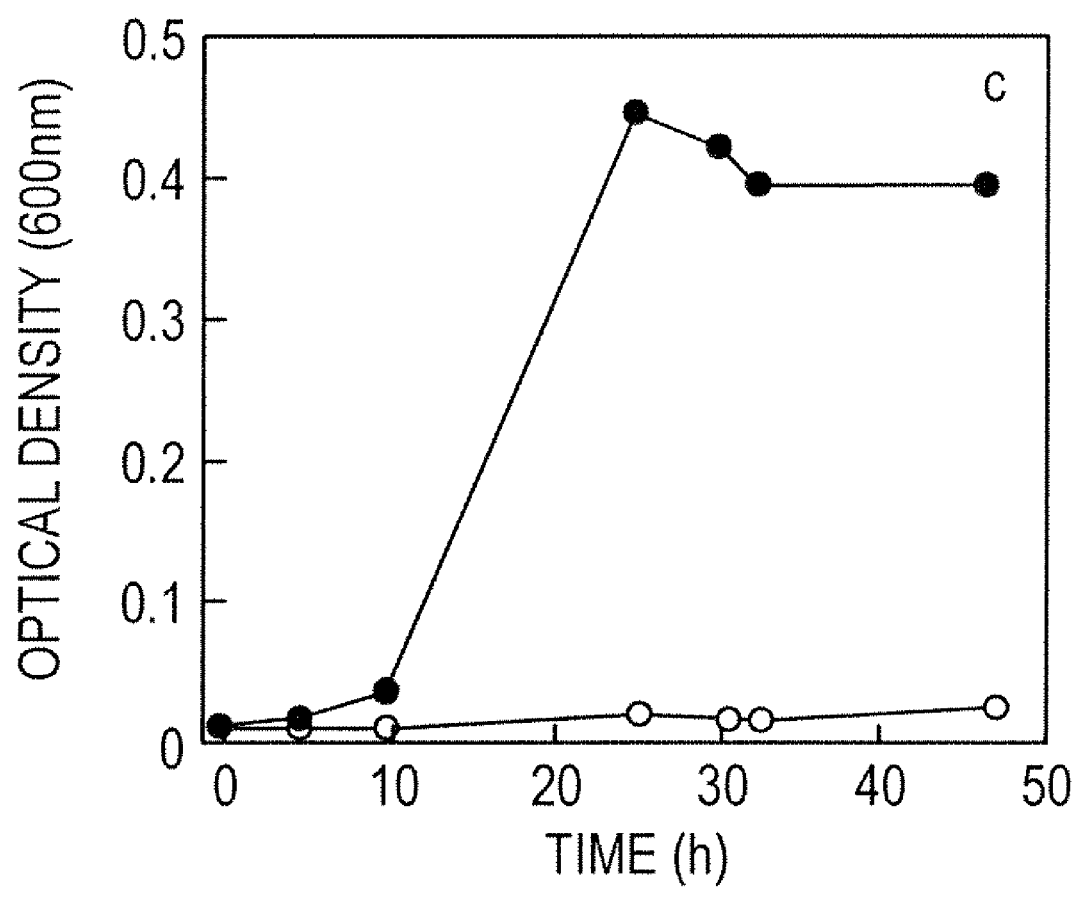

Functional proof that the pcrA gene is involved in perchlorate reduction was obtained by mutational knockout in *D. aromatica*, in which insertional inactivation of the pcrA gene with a tetracycline resistance cassette abolished both perchlorate and chlorate reduction (FIG. 5). However, as expected, the *D. aromatica* pcrA mutant was still able to grow aerobically (data not shown), as well as anaerobically via nitrate reduction, indicating that there are separate metabolic pathways for each electron acceptor (FIG. 5).

Figure 6:
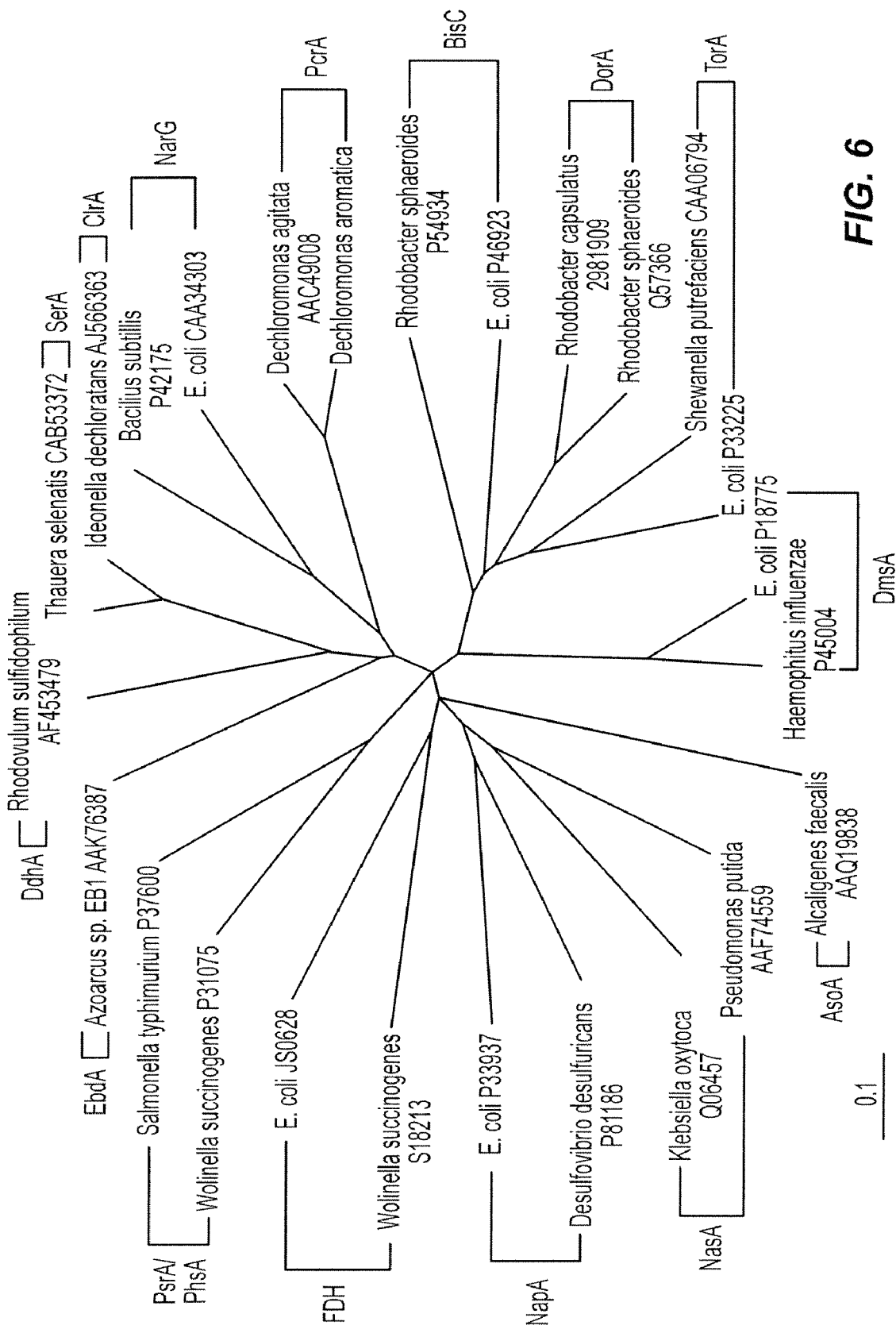
FIG. 6. Unrooted neighbor-joining tree indicating the evolutionary distances in the DMSO reductase family of molybdoenzymes. GenBank accession numbers are indicated after the names.

Phylogenetic analysis of PcrA. Based on the biochemical analysis of the purified enzyme from strain GR-1 (Kengen et al., J. Bacteriol 181:6706-6711, 1999), perchlorate reductase was identified as a member of the type II DMSO reductase family (McEwan et al., Geomicrobiol., J., 19:3-21, 2002). Our sequence analysis of the perchlorate reductase genes also supported this identification. Enzymes in the prokaryotic type II DMSO reductase family reside in the periplasm and have a common pterin molybdenum cofactor known as bis(molybdopterin guanine dinucleotide) Mo (Kisker et al., Annu Rev. Biochem., 66:233-267, 1997, McDevitt et al., Mol. Microbiol., 44:1575-1587, 2002, McEwan et al., Geomicrobiol., J., 19:3-21, 2002). DMSO reductase enzymes are involved in a myriad of reduction capabilities, including the dissimilatory reduction of toxic elements such as selenate and arsenate (McEwan et al., Geomicrobiol., J., 19:3-21, 2002). Using α-subunit protein sequences from known microbial DMSO enzymes (McDevitt et al., Mol. Microbiol., 44:1575-1587, 2002, McEwan et al., Geomicrobiol., J., 19:3-21, 2002) and from the PcrA sequences resulting from this study, a phylogenetic tree was constructed (FIG. 6), and this tree had a topology similar to that of a DMSO reductase family tree constructed by McEwan and coworkers (McEwan et al., Geomicrobiol., J., 19:3-21, 2002).

The type I, type II, and type III DMSO enzymes form separate clades in the tree. The type I enzymes include formate dehydrogenase (FDH), periplasmic nitrate reductase (NapA), bacterial assimilatory nitrate reductase (NasA), and arsenite oxidase (AsoA) (McDevitt et al., Mol. Microbiol., 44:1575-1587, 2002, McEwan et al., Geomicrobiol., J., 19:3-21, 2002). Type II enzymes, such as ethylbenzene dehydrogenase (EbdA), dimethyl sulfide dehydrogenase (DdhA), selenate reductase (SerA), chlorate reductase (ClrA), nitrate reductase (NarG), and perchlorate reductase (PcrA), share a heterotrimeric structure and have conserved cysteine residues for Fe—S binding in the β-subunit (McDevitt et al., Mol. Microbiol., 44:1575-1587, 2002, McEwan et al., Geomicrobiol., J., 19:3-21, 2002). The type III enzymes are represented by the monomeric proteins biotin sulfoxide reductase (BisC), dimethyl sulfoxide reductase (DorA), and trimethylamine-N-oxide reductase (TorA) (20, McEwan et al., Geomicrobiol., J., 19:3-21, 2002). The type II enzyme dimethyl sulfoxide reductase (DmsA) and the type II enzymes polysulfide and thiosulfate reductases (PsrA/PhsA) form unaffiliated lineages (McDevitt et al., Mol. Microbiol., 44:1575-1587, 2002, McEwan et al., Geomicrobiol., J., 19:3-21, 2002).

Our analysis indicated that PcrA forms its own monophyletic group in the type II DMSO enzymes and has a common ancestor with *E. coli* and *Bacillus subtilis* NarG, L dechloratans ClrA, *Thauera selenatis* SerA, *Rhodovulum sulfidophilum* DdhA, and *Azoarcus* sp. strain EBI EbdA. The alignment used for tree construction indicated that PcrA contains the type II DMSO signature motif $[HX_3CX_2CX_{(n)}C]$ for binding one 4Fe-4S center in domain I (data not shown) (Jormakka et al., Structure, 12:95-104, 2004). Based on the NarG analysis of Jormakka and coworkers, type II DMSO enzymes have also been shown to contain a conserved Asp residue for Mo ion binding (Jormakka et al., Structure, 12:95-104, 2004). This residue is present at position 212 in PcrA.

The tree topology also indicated that PcrA is more closely related to NarG from *B. subtilis* and *E. coli* than to ClrA from L dechloratans, further emphasizing the differences between the perchlorate and chlorate reductases. The distance between the perchlorate and chlorate reductases indicates that they are distinct enzymes, which was supported by our molecular probing of genomic DNAs from perchlorate and chlorate reducers, as well as from close relatives unable to reduce either electron acceptor (FIG. 7). The slot blot analysis resulted in hybridization signals for the pcrA gene from perchlorate reducers alone. No signal was observed for the close relatives or for *Pseudomonas* sp. strain PK, *D. chlorophilus*, or *I. dechloratans*, organisms that are capable of chlorate reduction but not perchlorate reduction (FIG. 7). This finding supports the hypothesis that two distinct metabolic pathways involved in the reduction of these analogous compounds evolved.

From the current study, it is clear that a more complete understanding of perchlorate reduction and other environmentally significant pathways is pivotal for obtaining knowledge applicable to the design of future bioremediation strategies. Perchlorate reductase and other members of the type II DMSO reductase family play a role in a broad range of substrate reductions and oxidations, and differences in various active sites are the major differences between family members. The different active sites indicate that there was a common reductase ancestor which acquired mutations advantageous for utilization of specific substrates. Thus, it is possible that directed mutagenesis of the active sites of DMSO enzymes could lead to creation of novel enzymes useful for biotechnological as well as bioremediation applications.

The discussion in the present example reveals the significance of using DPRB in environmental bioremediation techniques. The previous examples have provided detailed and exemplary methods for identifying the DPRB in accordance with the present invention. It should be understood that the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

| | | | | |
|---|---|---|---|---|
| \multicolumn{5}{l}{Sequences for sequence listing} |

| SEQ ID NO: | Genbank Accession No. | Sequence Type | Description | Sequence |
|---|---|---|---|---|
| 1 | N/A | DNA | DPR.F primer | GCNCCNCCNGTNGCNTTYATG |
| 2 | N/A | DNA | DPR.R primer | RTCRTTNACYTCNGCRTGDAT |
| 3 | N/A | DNA | DPR1.F primer | ACAGCGABBTGCTDDTGCG |
| 4 | N/A | DNA | DPR1.R primer | VGCCGAAGGVADAACCABV |
| 5 | N/A | DNA | UPR.F primer | GAYCCNGCNCTNGARGGNAAR |
| 6 | N/A | DNA | UPR.R primer | CCADATNGTNGTYTGRCA |
| 7 | N/A | DNA | UPR1.F primer | AGACCACBATCTGGACCTATGTC |
| 8 | N/A | DNA | UPR1.R primer | GGVADAACCABVTCVGAATAYA |
| 9 | N/A | DNA | primer | GCGCGGAATTC |
| 10 | N/A | DNA | primer | GCGCGCAAGCTT |
| 11 | N/A | DNA | primer | GC(I/N)CC(I/N)CC(I/N)GT(I/N)GC(I/N)TTYATG |
| 12 | N/A | DNA | primer | RTCRTT(I/N)ACYTC(I/N)GCRTGDAT |
| 13 | N/A | DNA | primer | GAYCC(I/N)GC(I/N)CT(I/N)GARGG(I/N)AAR |
| 14 | N/A | DNA | primer | CCADAT(I/N)GT(I/N)GTYTGRCA |
| 15 | N/A | DNA | primer | GARCGCAARRGNGCNGCNGMNGARGT |
| 16 | N/A | DNA | primer | TCRAARTANGTDATEAARTC |
| 17 | N/A | DNA | primer | TYGAVAARCAYAAGGAHAAVGT |
| 18 | N/A | DNA | primer | GAGTGGTAVARYTTVCGYTT |
| 19 | N/A | DNA | primer | GANCGNAANNGNGCNGCNGNNGANGT |
| 20 | N/A | DNA | primer | TCNAANTANGTNATNAANTC |
| 21 | N/A | DNA | primer | GARCGCAARRG(I/N)GCIGC(I/N)GM(I/N)GARGT |
| 22 | N/A | DNA | primer | TCRAARTA(I/N)GTVATRAARTC |
| 23 | N/A | DNA | primer | GA(I/N)CG(I/N)AA(I/N)(I/N)G(I/N)GC(I/N)GC(I/N)G(I/N)(I/N)GA(I/N)GT |
| 24 | N/A | DNA | primer | TC(I/N)AA(I/N)TA(I/N)GT(I/N)AT(I/N)AA(I/N)TC |
| 25 | N/A | DNA | primer | GTCGTTNACTTCNGCGTGAAT |
| 26 | N/A | DNA | primer | CGCGAAGGTAGTCAGCATCT |
| 27 | AY180108 | DNA | *D. agitata* (pcrA) | atggcacgactgagtcgcagagatttttg aaggcatccgccgccactctgctgggtaat tcacttaccttcaaaaacattagcggccacc atggatttatccggcgccttcgaatattcg ggctgggaaaattttcatcgcaaccagtgg tcgtgggacaagaaaactcgcggagcgcac ctgatcaactgtactggggcttgcccgcac ttcgtttatacgaaagatggtgtggtcatt cgcgaggagcagtccaaggacattccgccg atgccgaatatcccggaattgaatccccgg gggtgcaacaaggggagtgcgcacaccac tacatgtatggtccgcatcgcctgaaatat cctttgatccgggttggcgaacgcggggag ggcaagtggcggcgtgccacgtgggaggag gcactagacccttatctcagacaagataatc |

Sequences for sequence listing

| SEQ ID NO: | Genbank Accession No. | Sequence Type | Description | Sequence |
|---|---|---|---|---|
| | | | | gacacgatcaagaatcactctcccgattgc |
| | | | | atcagtgtctactcacctcttccgggcaca |
| | | | | gcaccagtatcgttctctgctggacacagg |
| | | | | tttgcgcactatatcggcgcccatacacat |
| | | | | accttctttgactggtacagtgaccatccc |
| | | | | actggtcagacacagacgtgcggtgtccag |
| | | | | ggcgactcagcggagtgctccgactggttc |
| | | | | aactcaaaatacataatcctctgggggca |
| | | | | aaccccactcagactcgtattccagatgcg |
| | | | | catttcctgtcagaggcgcagttgaacggc |
| | | | | gcgaaggtagtcagcatctccccggattc |
| | | | | aactcttctaccatcaaggcggaccgttgg |
| | | | | attcaccctctgcccggtactgatggcgcc |
| | | | | ctcgcactggccatggcgcatgtgatcatc |
| | | | | aaggaaaagctctacgacgcccacaacctc |
| | | | | aaggaacaaactgatctaccgtatttgatc |
| | | | | agaagggacaccaagcggttcttacgtgaa |
| | | | | gctgatgtggttgccggggatccaaagat |
| | | | | aagttctatatttgggacagcaagactggc |
| | | | | aagccggtaatcacgaaaggttcctgggc |
| | | | | gaccaaccagaacaaaaagctccgcctgtc |
| | | | | gcatttatgggaaggaacacccatacattc |
| | | | | ccaaagggctatatcgccctggagaatctg |
| | | | | gaccccgccctggaaggcaaatttcaggtc |
| | | | | aagttgcaggatggaaatacagttgaagtc |
| | | | | agaccagtattcgaaattctgaaatcgcgc |
| | | | | atcgaggccgacaacaatatcgccaaggca |
| | | | | gcgaaaatcaccggggtgccggcaaagacc |
| | | | | atcattgaagtggccagagagtatgcaaca |
| | | | | acgcagccggcgatgatcatttgcggtggc |
| | | | | ggcactatgcactggtattacagcgacgtg |
| | | | | ctgttacgtgcgatgcatctgctaaccgca |
| | | | | ctcgttggcagcgaaggcaagaatggcggc |
| | | | | gggatgaatcattacatcggacagtggaag |
| | | | | cctgtcttcctgccgggtgtggctgctctc |
| | | | | gccttccccgaaggccctgcgaacgaacgg |
| | | | | tcctgccagacgacgatctggacttacatc |
| | | | | catgccgaagttaacgacgagatggcaaat |
| | | | | gtcgggatcgataccgacaagtatctgatg |
| | | | | cacgcgatcgatacgcgccaaatgccgaat |
| | | | | taccctcgagacggcagagatcccaaagta |
| | | | | tttatcgtctatcgcggcaactggctaaac |
| | | | | caagccaagggacagaaatatgtcttgcgc |
| | | | | aatctctggcccaagctggatttgattgtt |
| | | | | gacatcaatatccgcatggactcaacggcg |
| | | | | ctgtattcggatgttgtgctgccttccgct |
| | | | | cactggtacgaaaagctcgacctcaacgtc |
| | | | | accgccgagcacacctatatcaacatgacg |
| | | | | gaaccggcaatcaagccgatgtgggaatcc |
| | | | | aagaccgattggcagattttcctcgcactc |
| | | | | gccaaacgcgttgaaatgtcagccaagcgc |
| | | | | aagagttttgagaggttttacgacgaacaa |
| | | | | ttcaagtgggcacgcgacctgacgaacctg |
| | | | | tggaaccagatgaccatggacggcaagttg |
| | | | | gccgaggatgaggctgctgcccaatacatt |
| | | | | ctggacactgcccccattcgaaaggcatt |
| | | | | acgctccagatgctgagggaaaaaggtgag |
| | | | | cgcttcaaggcgaattggacttcgccgatg |
| | | | | aaggaaggcgtgccctataccccgttccag |
| | | | | aattacattgtcgacaagaagccttggccg |
| | | | | acactcacggggcgccagcagttctatctg |
| | | | | gaccatgaagtgttcttcgaaatgggtgtc |
| | | | | gaattgccgacctacaaggctccggtcgat |
| | | | | gcggacaaattccccttccgcttcaactcg |
| | | | | ccacacagtcgtcattcgatccactcgacc |
| | | | | ttcaaggatagtgtgctgatgctacggctt |
| | | | | cagcgcggcggtccctgcgtagaaatctcg |
| | | | | ccgatcgatgccacggcaattggagtcaag |
| | | | | gacaacgactgggtagaaatctggaatagc |
| | | | | cacggcaaggtgatctgccgggccaagatc |
| | | | | cgtgccggtgagcaacgtggccgcgtctcc |
| | | | | atgtggcacaccccggaactgtacatggat |
| | | | | ctcctcgaaggcagcacgcaaagcgtatgc |

Sequences for sequence listing

| SEQ ID NO: | Genbank Accession No. | Sequence Type | Description | Sequence |
|---|---|---|---|---|
| | | | | cccgtccgcatcacgccaacgcacttggtg ggcaactacggacatttggtgtttcgcccg aactactacggaccggccggcagccagcga gacgttcgtgtcgatgtgaaacgctatatc ggcgcaactccgatcagtctctag |
| 28 | AY180108 | AA | *D. agitata* (pcrA) | MARLSRRDFLKASAATLLGNSLTFKTLAAT MDLSGAFEYSGWENFHRNQWSWDKKTRGAH LINCTGACPHFVYTKDGVVIREEQSKDIPP MPNIPELNPRGCNKGECAHHYMYGPHRLKY PLIRVGERGEGKWRRATWEEALDLISDKII DTIKNHSPDCISVYSPLPGTAPVSFSAGHR FAHYIGAHTHTFFDWYSDHPTGQTQTCSVQ GDSAECSDWFNSKYIILWGANPTQTRIPDA HFLSEAQLNGAKVVSISPDFNSSTIKADRW IHPLPGTDGALALAMAHVIIKEKLYDAHNL KEQTDLPYLIRRDTKRFLREADVVAGGSKD KFYIWDSKTGKPVITKGSWGDQPEQKAPPV AFMGRNTHTFPKGYIALENLDPALEGKFQV KLQDGNTVEVRPVFEILKSRIEADNNIAKA AKITGVPAKTIIEVAREYATTQPAMIICGG GTMHWYYSDVLLRAMHLLTALVGSEGKNGG GMNHYIGQWKPVFLPSVAALAFPEGPANER SCQTTIWTYIHAEVNDEMANVGIDTDKYLM HAIDTRQMPNYPRDGRDPKVFIVYRGNWLN QAKGQKYVLRNLWPKLDLIVDINIRMDSTA LYSDVVLPSAHWYEKLDLNVTAEHTYINMT EPAIKPMWESKTDWQIFLALAKRVEMSAKR KSFERFYDEQFKWARDLTNLWNQMTMDGKL AEDEAAAQYILDTAPHSKGITLQMLREKGE RFKANWTSPMKEGVPYTPFQNYIVDKKPWP TLTGRQQFYLDHEVFFEMGVELPTYKAPVD ADKFPFRFNSPHSRHSIHSTFKDSVLMLRL QRGGPCVEISPIDATAIGVKDNDWVEIWNS HGKVICRAKIRAGEQRGRVSMWHTPELYMD LLEGSTQSVCPVRITPTHLVGNYGHLVFRP NYYGPAGSQRDVRVDVKRYIGATPISL |
| 29 | AY953269 | DNA | *D. agitata* (pcrB) | atgtcaaatatgacgaagtcgcctaaacgc caattggcatatgttgccgacctgaataag tgcattggctgccagacatgcactgtcgca tgcaagactctttggactagtggacctgga caggactacatgtattggcggaatgtcgaa accgccccaggtttggggtatccaagaaac tggcagagcaagggcggtggatacaaggat ggagtcctgcagaaagggaagattccgccg atgatcgattatggcgttcccttcgaattc gactacgccggtcggcttttcgaagggaaa aaggaaagagcgcgaccgagtccgacgcct cggtatgctcccaattgggatgaggatcag ggagcgggcgaatatcccaacaactccttt ttctatgtgccgcggatgtgcaaccactgc gccaagccggcatgtcttgaagcctgcccg aatgaagcgatatacaagcgcgagcaagac ggcctggtggtgatccatcaggagaagtgc aaaggggctcaggcatgtatccagtcctgc ccatatgccaaaccatactttaatgctcag gtcaataaagccaacaagtgcatcggttgc ttcccgcggattgaaaaaggggttgcaccg gcatgcgttgctgagtgtgcgggaagagcc atgcatgtcggcttcatcgatgaccaagaa agctccgtgttcaagctggtcaagcggttc ggcgtggcactgccttgcaccccgagtac ggcaccgaacccaacgtgttctatgtccct cccgttctcggaccgcgcgtagaaatgccg aatggcgaacataccgccgacccgaaaatt tcgatgactcagcttgaacagttgtttggc aagcaggtccgcgaggttttgaagacgctg caggccgaacgcgagaaaaagatcaagaac cagccgtctgaactgatggacatcctgatc ggccgacgcagtgcggacatgatgatttcg cctatgacctga |

Sequences for sequence listing

| SEQ ID NO: | Genbank Accession No. | Sequence Type | Description | Sequence |
|---|---|---|---|---|
| 30 | AY953269 | AA | *D. agitata* (pcrB) | MSNMTKSPKRQLAYVADLNKCIGCQTCTVA CKTLWTSGPGQDYMYWRNVETAPGLGYPRN WQSKGGGYKDGVLQKGKIPPMIDYGVPFEF DYAGRLFEGKKERARPSPTPRYAPNWDEDQ GAGEYPNNSFFYVPRMCNHCAKPACLEACP NEAIYKREQDGLVVIHQEKCKGAQACIQSC PYAKPYFNAQVNKANKCIGCFPRIEKGVAP ACVAECAGRAMHVGFIDDQESSVFKLVKRF GVALPLHPEYGTEPNVFYVPPVLGPRVEMP NGEHTADPKISMTQLEQLFGKQVREVLKTL QAEREKKIKNQPSELMDILIGRRSADMMIS PMT |
| 31 | AY953270 | DNA | *D. agitata* (pcrC) | atgaaaagaatcgttgctctgttaagcacg ttgctcgttaccgcgatgccgagcatggc gtagcccaacagaccgaatatttaggcttt cgcgcatgcacaaagtgtcacgatgcccag ggtgataccctggcggacatcggcacatgcc aaagcctttgagt |
| 32 | AY953270 | AA | *D. agitata* (pcrC) | MKRIVALLSTLLVTAMPSMGVAQQTEYLGF RACTKCHDAQGDTWRTSAHAKAFE |
| 33 | AY953271 | DNA | *D. agitata* (pcrD) | atgaatagtattaccgacgatcgactcgtc ttggcggccgataaagcgttatgccgaagc cacatttattcattgttggccagtggattt ggatatcccgacgaatctggttatcaggga ttttcggacggcaagtttattgatgaaatc cgtcaggaactcggggtatgttgggtgaa ctcttggagcattttaatgaggtacttgct cctgggttgaaacttgcctgctcgcgcgaa gtattcgaatcacagttcttgagtgcattc gagaccaatatgccatcacctagcgcctcc ttgaatgaaggtgttcacatatttaaatcg gaccgaccaaatttattgctcgaactgaag ggttttttacagcaacttcggcttgcaggtc gatagcaaaggcaatgagcttgaagacact ctgacagcagaacttgatttcatgcagttt cttgcgttgaaacaggcacaggcccatctc gaaggcatgtcggctgatgcctacaagttg gcgcagaaggattttctggagcggcaccta tgtgcttggttgccattggtgcggagggaa atcgccgaaaaggtgactaccccattcttc gtcactcttgctgagtttgcagaaagcttt gcgcttgctaatttaagagaattgaaagaa gagctaggagaataa |
| 34 | AY953271 | AA | *D. agitata* (pcrD) | MNSITDDRLVLAADKALCRSHIYSLLASGF GYPDESGYQGFSDGKFIDEIRQELGVCWGE LLEHFNEVLAPGLKLACSREVFESQFLSAF ETNMPSPSASLNEGVHIFKSDRPNLLLELK GFYSNFGLQVDSKGNELEDTLTAELDFMQF LALKQAQAHLEGMSADAYKLAQKDFLERHL CAWLPLVRREIAEKVTTPFFVTLAEFAESF ALANLRELKEELGE |
| 35 | Q9S1G9 | AA | *T. selenatis* (SerB) | MSQRQLAYVFDLNKCIGCHTCTMACKQLWT NRDGREYMYWNNVESRPGKGYPKNWEQKGG GFDKDGKLKTNGIIPIRADYGGTWNYNLLE TLVEGKSNQVVPDEKPTWGPNWDEDEGKGE FPNNHYFYLPRICNHCSNPACLAACPTKAI YKREEDGLVVVDQSRCKGYRYCVKACPYGK MYFNLQKGTSEKCIGCYPRVEKGEAPACVK QCSGRIRFWGYRDDKDGPIYKLVDQWKVAL PLHAEYGTEPNVFYVPPMNTTPPPFEEDGR LGDKPRIPIEDLEALFGPGVKQALATLGGE MAKRRKAQASELTDILIGYTNKDRYGI |
| 36 | P60069 | AA | *I. dechloratans* (ClrB) | MSQRQVAYVFDLNKCIGCHTCTMACKQLWT NRDGREYMYWNNVETRPGKGYPKNWEGKGG GFDQEGKLKTNGIIPIMADYGGRIGDFNLN EVLLEGKADQVVPHEKATWGPNWDEDEGKG EFPNNHSFYLPRICNHCSNPACLAACPTKA |

Sequences for sequence listing

| SEQ ID NO: | Genbank Accession No. | Sequence Type | Description | Sequence |
|---|---|---|---|---|
| | | | | IYKRPEDGIVVVDQTRCRGYRYCVKACPYG KMYFNLQKGKSEKCIGCYPRVEKGEAPACV KQCSGRIRFWGYRDDKNGPIYKLVEQWKVA LPLHAEYGTEPNVFYVPPMNTTPPPFEEDG RLGDKPRIPIEDLEALFGPGVKQALATLGG EMAKRRKAQASELTDILIGFTNKDRYGV |
| 37 | CAD58340 | AA | Azoarcus sp. EbN1 (EbdB) | MTYVQDGNKSELRKAKRQLVTVIDLNKCLG CQTCTVACKNIWTKRPGTEHMRWNNVTTYP GKGYPRDYERKGGGFLRGEPQPGVLPTLID SGDDFQFNHKEVFYEGKGQTVHFHPTSKST GKDPAWGYNWDEDQSSSKWPNPFFFYLARM CNHCTNPACLAACPTGAIYKREDNGIVLVD QERCKGHRHCVEACPYKAIYFNPVSQTSEK CILCYPRIEKGIANACNRQCPGRVRAFGYL DDTTSHVHKLVKKWKVALPLHAEYGTGPNI YYVPPMGARGFGEDGEITDKTRIPLDVLES LFGPEVKRVLAVLHTERENMRAGRGSELMD LLISKKWSDRFGGFTNDPLTQS |
| 38 | AAN46633 | AA | R. sulfidophilum (DdhB) | MVKRQISMVLDLNKCIGCQTCTSACKLQWT NRNGREYMYWNNVETHPGPGYPRNYEHSGG GFDEEGALKIGITPSAEDYGIPWEYNYEEA LMTGTDPWLRPNVKPTWGANWNEDEGRGEY PNSYYFYLPRICNHCANPGCLAACARNAIY KRQEDGIVLVDQERCGRYRYCITACPYKKV YFNEQISKAEKCIFCYPRIEKGLPTACAKQ CVGRIRFIGYLDDEASPVHLLVERYKVAIP LHPEWGTKPSVFYVPPLAPPRIGDDGEPTE ETRVPLAYLKELFGEAVVPALETLKTERAK KQSGAESELMDTLIGYRHPEMFKLS |
| 39 | CAD22070 | AA | H. marismortui (NarH) | MSSDQQDDQGEEDTLVNVADGVDHQVAMVM DLNKCIGCQTCTIACKNLWTEDGGSEYMYW NNVETKPGEGYPRGWENSGGGWKSGEHKER QPGEIPDEEDYGRAWEFNHEEIMYEGSDEP LRPRDGAEWGPNWDEDQSASEYPNSYYFYL PRICNHCTHPSCVEACPRSALYKRQEDGIV LVDQDRCRGYRYCVEGCPYKKVYYNTVSKK SEKCIFCYPRIEGEGPDSETFAPACAEECP PQLRLVGFLDDEEGPIHKLVNEYEVALPLH PEFRTQPNVYYIPPFAPGQHTEDGETVDID RIPRQYLRDLFGDGVDQALDTIERERQRAR QGEDSELMELLQDKNPAKQYRLEVFDDE |
| 40 | NP_842334 | AA | N. europaea (cytochrome c554) | MKIMIACGLVAAALFTLTSGQSLAADAPFE GRKKCSSCHKAQAQSWKDTAHAKAMESLKP NVKKEAKQKAKLDPAKDYTQDKDCVGCHVD GFSQKGGYTIESPKPMLTGVGCESCHGPGR NFRGDHRKSGQAFEKSGKKTPRKDLAKKGQ DFHFEERCSACHLNYEGSPWKGAKAPYTPF TPEVDAKYTFKFDEMVKEVKAMHEHYKLEG VFEGEPKFKFHDEFQASAKPAKKGK |
| 41 | AF047462 | DNA | D. Aginata | tgaacgctggcggcatgccttacacatgca agtcgaacggcagcacggacttcggtctgg tggcgagtggcgaacgggtgagtaatgtat cggaacgtacctttcagtgggggataacgt agcgaaagttacgctaataccgcatattct gtgagcaggaaagcaggggatcgcaagacc ttgcgctgattgagcggccgatatcagatt agctagttggtggggtaaaggcctaccaag gctacgatctgtagcgggtctgagaggatg atccgccacactgaactgagacacggtcc agactcctacgggaggcagcagtggggaat tttggacaatgggggcaaccctgatccagc catgccgcgtgagtgaagaaggccttcggg ttgtaaagctctttcggccgggaagaaatc gcatcagctaataccggtgtggatgacgg tacccgaataagaagcaccggctaactacg tgccagcagccgcggtaatacgtagggtgc gagcgttaatcggaattactgggcgtaaag cgtgcgcaggcggttgtgtaagacaggcgt |

Sequences for sequence listing

| SEQ ID NO: | Genbank Accession No. | Sequence Type | Description | Sequence |
|---|---|---|---|---|
| | | | | gaaatccccgggctcaacctgggaactgcg cttgtgactgcacagctagagtacggcaga ggggggtggaattccacgtgtagcagtgaa atgcgtagagatgtggaggaacaccgatgg cgaaggcagcccctgggccgatactgacg ctcatgcacgaaagcgtgggtagcaaacag gattagataccctggtagtccacgccctaa acgatgtcaactaggtgttgggtgggtaaa accacctagtaccgtagctaacgcgtgaag ttgaccgcctggggagtacggccgcaaggt taaaactcaaaggaattgacggggacccgc acaagcggtggatgatgtggattaattcga tgcaacgcgaaaaaccttacctacccttga catgtccagaagcccggagagatttgggtg tgcccgaaagggaactggaacacaggtgct gcatggctgtcgtcagctcgtgtcgtgaga tgttgggttaagtcccgcaacgagcgcaac ccttgtcgttaattgccatcatttagttgg gcactttaacgagactgccggtgacaaacc ggaggaaggtggggatgacgtcaagtcctc atggcccttatgggtagggcttcacacgtc atacaatggtcggtacagagggttgccaag ccgcgaggtggagccaatcccagaaagccg atcgtagtccggattgcaggctgcaactcg cctgcatgaagtcggaatcgctagtaatcg cggatcagcatgtcgcggtgaatacgttcc cgggtcttgtacacaccgcccgtcacacca tgggagcgggttccgccagaagatggatgc ctaaccgcaaggagggcgcttaccacggcg gggttcgtgactggggtgaagtcgtaacaa ggtagccgtaggggaacctgcggctggatc acctcc |
| 42 | D16209 | DNA | R. tenuis | attgaacgctggcggcatgccttacacatg caagtcgaacggcagcacgggagcaatcct ggtggcgagtggcgaacgggtgagtaatgc atcggaacgtgcccctgaagtgggggataac gtagcgaaagttacgctaataccgcatatt ctgtgagcaggaaagcaggggatcgcaaga ccttgcgctttgggagcggccgatgtcgga ttagctagttggtggggtaaaggcctacca aggccacgatccgtagcgggtctgagagga tgatccgccacactgggactgagacacggc ccagactcctacgggaggcagcagtgggga attttggacaatgggcgaaagcctgatcca gccatgccgcgtgagtgaagaaggccttcg ggttgtaaagctctttcggcggggaagaaa ttgctcaggataatacctgagtagatgac ggtacccgaagaagaagcaccggctaacta cgtgccagcagccgcggtaatacgtagggt gcgagcgttaatcggaattactgggcgtaa agcgtgcgcaggcggttgtgtaagacagac gtgaaatccccgggctcaacctgggaactg cgtttgtgactgcacgactagagtgtggca gagggggtggaattccacgtgtagcagtg aaatgcgtagagatgtggaggaacaccgat ggcgaaggcagcccctgggccaatactga cgctcatgcacgaaagcgtggggagcaaac aggattagataccctggtagtccacgccct aaacgatgtcaactaggtgttggtgggtt aaacccattagtgccgtagctaacgcgtga agttgaccgcctggggagtacggccgcaag gttaaaactcaaaggaattgacggggaccc gcacaagcggtggatgatgtggattaattc gatgcaacgcgaaaaaccttacctacccctt gacatgtcaggaatcctgaagagattcggg agtgcccgaaagggagcctgaacacaggtg ctgcatggctgtcgtcagctcgtgncgtga gatgttgggttaagtcccgcaacgagcgca accccttgtcattaattgccatcatttagtt gggcactctaatgaaactgccggtgacaaa ccggaggaaggtggggatgacgtcaagtcc tcatggcccttatgggtagggcttcacacg |

Sequences for sequence listing

| SEQ ID NO: | Genbank Accession No. | Sequence Type | Description | Sequence |
|---|---|---|---|---|
| | | | | tcatacaatggtcggtacagagggttgcca |
| | | | | agccgcgaggtggagccaatcacagaaagc |
| | | | | cgatcgtagtccggattgcagtctgcaact |
| | | | | cgactgcatgaagtcggaatcgctngtaat |
| | | | | cgcggatcagcatgtcgcggtgaatacgtt |
| | | | | cccgggtcttgtacacaccgcccgtcacac |
| | | | | catgggagcgggttctgccagaagtagtta |
| | | | | gcctaaccgcaaggagggcgattaccacgg |
| | | | | cagcgttcgtgactggggtg |
| 43 | AY032610 | DNA | *D. aromatica* | gagtttgatcctggctcagattgaacgctg |
| | | | | gcggcatgccttacacatgcaagtcgaacg |
| | | | | gcagcacgggagcaatcctggtggcgagtg |
| | | | | gcgaacgggtgagtaatatatcggaacgta |
| | | | | cctttcagtgggggataacgtagcgaaagt |
| | | | | tacgctaataccgcatattctgtgagcagg |
| | | | | aaagcaggggatcgcaagaccttgcgctga |
| | | | | ttgagcggccgatatcagattagctagttg |
| | | | | gtgaggtaaaggctcaccaaggcgacgatc |
| | | | | tgtagcgggtctgagaggatgatccgccac |
| | | | | actggaactgagacacggtccagactccta |
| | | | | cgggaggcagcagtggggaattttggacaa |
| | | | | tgggggcaaccctgatccagccatgccgcg |
| | | | | tgagtgaagaaggccttcgggttgtaaagc |
| | | | | tctttcagccgggaagaaaacgcatgggtt |
| | | | | aataccctgtgtggatgacggtaccggaat |
| | | | | aagaagcaccggctaactacgtgccagcag |
| | | | | ccgcggtaatacgtagggtgcgagcgttaa |
| | | | | tcggaattactgggcgtaaagcgtgcgcag |
| | | | | gcggtttgttaagataggcgtgaaatcccc |
| | | | | gggctcaacctgggaactgcgtttatgact |
| | | | | ggcaggctagagtatggcagaggggggtgg |
| | | | | aattccacgtgtagcagtgaaatgcgtaga |
| | | | | gatgtggaggaacaccgatggcgaaggcag |
| | | | | cccccctgggccaatactgacgctcatgca |
| | | | | gaaagcgtgggtagcaaacaggattagata |
| | | | | ccctggtagtccacgccctaaacgatgtca |
| | | | | actaggtgttggggagggtaaaaccttttag |
| | | | | taccggagctaacgcgtgaagttgaccgcc |
| | | | | tggggagtacggccgcaaggttaaaactca |
| | | | | aaggaattgacggggacccgcacaagcggt |
| | | | | ggatgatgtggattaattcgatgcaacgcg |
| | | | | aaaaaccttacctaccccttgacatgtccgg |
| | | | | aagcccttagagatttgggtgtgctcgaaa |
| | | | | gagagccggaacacaggtgctgcatggctg |
| | | | | tcgtcagctcgtgtcgtgagatgttgggtt |
| | | | | aagtcccgcaacgagcgcaacccttgtcgt |
| | | | | taattgccatcatttagttgggcacttt aa |
| | | | | cgagactgccggtgacaaaccggaggaagg |
| | | | | tggggatgacgtcaagtcctcatggccctt |
| | | | | atgggtagggcttcacacgtcatacaatgg |
| | | | | tcggtacaaaggggttgccaacccgcgaggg |
| | | | | ggagctaatcccagaaagccgatcgtagtc |
| | | | | cggatcgtaggctgcaactcgcctgcgtga |
| | | | | agtcggaatcgctagtaatcgtggatcagc |
| | | | | atgtcacggtgaatacgttcccgggtcttg |
| | | | | tacacaccgcccgtcacacaatgggagcgg |
| | | | | gttccgccagaagtaggtagcctaaccgca |
| | | | | aggggggcgcttaccacggcggggttcgtg |
| | | | | actggggtgaagtcgtaacaaggtagccgt |
| | | | | aggggaacctgcggctggatcacctcct |
| 44 | AY032611 | DNA | Dechloromonas sp. Strain JJ | tttgatcctggctcagattgaacgctggcg |
| | | | | gcatgccttacacatgcaagtcgaacggca |
| | | | | gcacgggagcaatcctggtggcgagtggcg |
| | | | | aacgggtgagtaatgtatcggaacgtacct |
| | | | | tcagtgggggataacgtagcgaaagttac |
| | | | | gctaataccgcatattctgtgagcaggaaa |
| | | | | gcaggggatcgcaagaccttgcgctgattg |
| | | | | agcggccgatatcagattagctagttggtg |
| | | | | aggtaaaggctcaccaaggcgacgatctgt |
| | | | | agcgggtctgagaggatgatccgccacact |
| | | | | ggaactgagacacggtccagactcctacgg |

-continued

Sequences for sequence listing

| SEQ ID NO: | Genbank Accession No. | Sequence Type | Description | Sequence |
|---|---|---|---|---|
| | | | | gaggcagcagtggggaattttggacaatgg |
| | | | | gggcaaccctgatccagccatgccgcgtga |
| | | | | gtgaagaaggccttcgggttgtaaagctct |
| | | | | ttcggccgggaagaaatcgcatgggttaat |
| | | | | accctgtgtggatgacggtaccggaataag |
| | | | | aagcaccggctaactacgtgccagcagccg |
| | | | | cggtaatacgtagggtgcgagcgttaatcg |
| | | | | gaattactgggcgtaaagcgtgcgcaggcg |
| | | | | gtttagtaagacaggcgtgaaatcccggg |
| | | | | ctcaacctgggaactgcgcttgtgactgct |
| | | | | aagctagagtacggcagagggggtggaat |
| | | | | tccacgtgtagcagtgaaatgcgtagagat |
| | | | | gtggaggaacaccgatggcgaaggcagccc |
| | | | | cctgggccgatactgacgctcatgcacgaa |
| | | | | agcgtgggtagcaaacaggattagataccc |
| | | | | tggtagtccacgccctaaacgatgtcaact |
| | | | | aggtgttgggtgggtaaaaccatttagtac |
| | | | | cggagctaacgcgtgaagttgaccgcctgg |
| | | | | ggagtacggccgcaaggttaaaactcaaag |
| | | | | gaattgacggggacccgcacaagcggtgga |
| | | | | tgatgtggattaattcgatgcaacgcgaaa |
| | | | | aaccttacctacccttgacatgtccagaag |
| | | | | cccgaagagatttgggtgtgcccgaaaggg |
| | | | | agctggaacacaggtgctgcatggctgtcg |
| | | | | tcagctcgtgtcgtgagatgttgggttaag |
| | | | | tcccgcaacgagcgcaaccttgtcgttaa |
| | | | | ttgccatcatttagttgggcactttaacga |
| | | | | gactgccggtgacaaaccggaggaaggtgg |
| | | | | ggatgacgtcaagtcctcatggcccttatg |
| | | | | ggtagggcttcacacgtcatacaatggtcg |
| | | | | gtacagagggttgccaagccgcgaggtgga |
| | | | | gccaatcccagatagccgatcgtagtccgg |
| | | | | atcgtaggctgcaactcgcctgcgtgaagt |
| | | | | cggaatcgctagtaatcgcggatcagcatg |
| | | | | tcgcggtgaatacgttcccgggtcttgtac |
| | | | | acaccgcccgtcacaccatgggagcgggtt |
| | | | | ccgccagaagtaggtagcctaaccgcaagg |
| | | | | ggggcgcttaccacggcggggttcgtgact |
| | | | | ggggtgaagtcgtaacaaggtagccgtagg |
| | | | | ggaacctgcggctggatcacctccc |
| 45 | AF170352 | DNA | D. anomolous strain WD | tttgagcctggctcagaacgaacgctggcg |
| | | | | gcaggcctaacacatgcaagtcgaacgaag |
| | | | | tcttcggacttagtggcgcacgggtgagta |
| | | | | acacgtgggaatataccttacgctgggga |
| | | | | taacatcgggaaactgatgctaataccgca |
| | | | | tacgcccttcgggggaaagatttatcggcg |
| | | | | aaagattagcccgcgtccgattagctagtt |
| | | | | ggtgaggtaatggctcaccaaggctccgat |
| | | | | cggtagctggtctgagaggatgaccagcca |
| | | | | cactgggactgagacacggcccagactcct |
| | | | | acgggaggcagcagtggggaatattggaca |
| | | | | atgggcgcaagcctgatccagccatgccgc |
| | | | | gtgagtgatgaaggccttagggttgtaaag |
| | | | | ctctttcacccacgacgatgatgacggtag |
| | | | | tgggagaagaagcccggctaacttcgtgc |
| | | | | cagcagccgcggtaatacgaaggggctag |
| | | | | cgttgttcggaattactgggcgtaaagcgc |
| | | | | acgcaggcggttcggtcagtcagaagtgaa |
| | | | | agcccgggcttaacctgggaactgctttt |
| | | | | gatactgccgagcttgaatcacggagaggg |
| | | | | tagtggaattccgagtgtagaggtgaaatt |
| | | | | cgtagatattcggaagaacaccagtggcga |
| | | | | aggcgactacctggccgtcgattgacgctc |
| | | | | atgtgcgaaagcgtggggagcaaacaggat |
| | | | | tagataccctggtagtccacgccgtaaacg |
| | | | | atgagtgctagttgttgggtgcatgcacc |
| | | | | tcagtgacgcagctaacgcgttaagcactc |
| | | | | cgcctggggagtacggccgcaaggttaaaa |
| | | | | ctcaaaggaattgacggggcccgcacaag |
| | | | | cggtggagcatgtggtttaattcgaagcaa |
| | | | | cgcgcagaaccttaccagcccttgacatgg |
| | | | | gaactatgggtccgagagattggatccttc |

Sequences for sequence listing

| SEQ ID NO: | Genbank Accession No. | Sequence Type | Description | Sequence |
|---|---|---|---|---|
| | | | | acttcgggtgggttccacacaggtgctgca tggctgtcgtcagctcgtgtcgtgagatgt tgggttaagtcccgcaacgagcgcaaccct catcgtcagttgccatcattcagttgggca ctctgacgaaactgccggtgacaagccgga ggaaggtggggatgacgtcaagtcctcatg gcccttacgggctgggctacacacgtgcta caatggtggtgacaatgggtcgcgagctcg cgagagttagctaatccccaaaagccatct cagttcggattgtactctgcaactcgagtg catgaagtcggaatcgctagtaatcgtgga tcagcatgccacggtgaatacgttcccggg ccttgtacacaccgcccgtcacaccatggg agttggctttacccgaagccggtgcgctaa ccgcaaggaggcagccgaccacggtaaggt cagcgactggggtgaagtcgtaacaaggta gccgtaggggaacctgcggccggatcacct cc |
| 46 | Y10110 | DNA | *M. magnetotacticum* | aacgaacgctggcggcaggcttaacacatg caagtcgaacgaagtcttcggacttagtgg cgcacgggtgagtaacacgtgggaatatac ctcttggtggggaataacgtcgggaaactg acgctaataccgcatacgcccttcggggga aagatttatcgccgagagattagcccgcgt ccgattagctagttggtgaggtaatggctc accaaggcgacgatcggtagctggtctgag aggatgatcagccacactgggactgagaca cggcccagactcctacgggaggcagcagtg gggaatattggacaatgggcgaaagcctga tccagccatgccgcgtgagtgatgaaggcc ttaggggttgtaaagctctttcacccacgac gatgatgacggtagtgggagaagaagcccc ggctaacttcgtgccagcagccgcggtaat acgaaggggggctagcgttgttcggaattac tgggcgtaaagcgcacgcaggcggtggtca tagtcagaagtgaaagccctgggctcaacc cgggaattgcttttgatactggaccgctag aatcacggagagggtagtggaattccgagt gtagaggtgaaattcgtagatattcggaag aacaccagtggcgaaggcgactacctggcc gtcgattgacgctcatgtgcgaaagcgtgg ggagcaaacaggattagataccctggtagt ccacgccgtaaacgatgagtgctagttgtt ggggtgcatgcacctcagtgacgcagctaa cgcgttaagcactccgcctggggagtacgg ccgcaaggttaaaactcaaaggaattgacg ggggcccgcacaagcggtggagcatgtggt ttaattcgaagcaacgcgcagaaccttacc agcccttgacatgggacgtatgtttgccag agatggtgacttgtcttcggacgcgtccac acaggtgctgcatggctgtcgtcagctcgt gtcgtgagatgttgggttaagtcccgcaac gagcgcaaccctcatcttcagttgccatca tttagttgggcactctgaagaaactgccgg tgacaagccggaggaaggtggggatgacgt caagtcctcatggcccttacgggctgggct acacacgtgctacaatggtggtgacagtgg gtcgctaactcgcgagagtatgctaatccc taaaagccatctcagttcggattgcactct gcaactcgagtgcatgaagtcggaatcgct agtaatcgtggatcagcatgccacggtgaa tacgttcccgggccttgtacacaccgcccg tcacaccatgggagttggctttacccgaag ccggtgcgctaaccgcaaggaggcagccga ccacggtaaggtcagcgactggggtgaagt cgtaacaaggtagccgtaggggaacctgcg gct |
| 47 | AF170358 | DNA | *Pseudomonas sp.* strain PK | atgaagagggcttgctctctgattcagcgg cggacgggtgagtaatgcctaggaatctgc ctgatagtgggggacaacgtttcgaaagga acgctaataccgcatacgtcctacgggaga |

Sequences for sequence listing

| SEQ ID NO: | Genbank Accession No. | Sequence Type | Description | Sequence |
|---|---|---|---|---|
| | | | | aagcaggggaccttcgggccttgcgctatc agatgagcctaggtcggattagctagttgg tgaggtaacggctcaccaaggcgacgatcc gtaactggtctgagaggatgatcagtcaca ctggaactgagacacggtccagactcctac ggggaggcagcagtggggaatattggacaat gggcgaaagcctgatccagccatgccgcgt gtgtgaagaaggtcttcggattgtaaagca ctttaagttgggaggaagggcattaaccta atacgttagtgttttgacgttaccgacaga ataagcaccggctaacttcgtgccagcagc cgcggtaatacgaagggtgcaagcgttaat cggaattactgggcgtaaagcgcgcgtagg tggtttgttaagttgaatgtgaaagccccg ggctcaacctgggaactgcatccaaaactg gcaagctagagtatggcagagggtggtgga atttcctgtgtagcggtgaaatgcgtagat ataggaaggaacaccagtggcgaaggcgac cacctgggctaatactgacactgaggtgcg aaagcgtggggagcaaacaggattagatac cctggtagtccacgccgtaaacgatgtcga ctagccgttgggatccttgagatcttagtg gcgcagctaacgcattaagtcgaccgcctg gggagtacggccgctaggttaaaactctaa tgaattgacggggggcccgcacaagcggtgg agcatgtggtttaattcgaagcaacgcgaa gaaccttaccaggccttgacatgcagagaa ctttccagagatggattggtgccttcggga actctgacacaggtgctgcatggctgtcgt cagctcgtgtcgtgagatgttgggttaagt cccgtaacgagcgcaacccttgtccttagt taccagcacgttaaggtgggcactctaagg agactgccggtgacaaaccggaggaaggtg gggatgacgtcaagtcatcatggcccttac ggcctgggctacacacgtgctacaatggtc ggtacaaagggttgccaagccgcgaggtgg agctaatcccataaaaccgatcgtagtccg gatcgcagtctgcaactcgactgcgtgaag tcggaatcgctagtaatcgtgaatcagaat gtcacggtgaatacgttcccgggccttgta cacaccgcccgtcacaccatgggagtgggt tgctccagaagtagctagtctaaccttcgg ggggacggttaccacggaggtattcatgac tggggtgaagtcgtaacaaggtagccgtag gggaacctgcggctggatcacctcctt |
| 48 | | DNA | P. stutzeri | gaacgctggcggcaggcctaacacatgcaa gtcgagcggatgaagagagcttgctctctg attcagcggcggacgggtgagtaatgccta ggaatctgcctgatagtgggggacaacgtt tcgaaaggaacgctaataccgcatacgtcc tacgggagaaagcaggggaccttcgggcct tgcgctatcagatgagcctaggtcggatta gctagttggtgaggtaacggctcaccaagg cgacgatccgtaactggtctgagaggatga tcagtcacactggaactgagacacggtcca gactcctacggggaggcagcagtggggaata ttggacaatgggcgaaagcctgatccagcc atgccgcgtgtgtgaagaaggtcttcggat tgtaaagcactttaagttgggaggaagggc attaacctaatacgttagtgttttgacgtt accgacagaataagcaccggctaacttcgt gccagcagccgcggtaatacgaagggtgca agcgttaatcggaattactgggcgtaaagc gcgcgtaggtggtttgttaagttgaatgtg aaagccccgggctcaacctgggaactgcat ccaaaactggcaagctagagtatggcagag ggtggtggaatttcctgtgtagcggtgaaa tgcgtagatataggaaggaacaccagtggc gaaggcgaccacctgggctaatactgacac tgaggtgcgaaagcgtggggagcaaacagg attagatacccctggtagtccacgccgtaaa cgatgtcgactagccgttgggatccttgag |

Sequences for sequence listing

| SEQ ID NO: | Genbank Accession No. | Sequence Type | Description | Sequence |
|---|---|---|---|---|
| | | | | atcttagtggcgcagctaacgcattaagtc |
| | | | | gaccgcctggggagtacggccgcaaggtta |
| | | | | aaactcaaatgaattgacggggggcccgcac |
| | | | | aagcggtggagcatgtggtttaattcgaag |
| | | | | caacgcgaagaaccttaccaggccttgaca |
| | | | | tgcagagaactttccagagatggattggtg |
| | | | | ccttcgggaactctgacacaggtgctgcat |
| | | | | ggctgtcgtcagctcgtgtcgtgagatgtt |
| | | | | gggttaagtcccgtaacgagcgcaacccctt |
| | | | | gtccttagttaccagcacgttaaggtgggc |
| | | | | actctaaggagactgccggtgacaaaccgg |
| | | | | aggaaggtggggatgacgtcaagtcatcat |
| | | | | ggcccttacggcctgggctacacacgtgct |
| | | | | acaatggtcggtacaaagggttgccaagcc |
| | | | | gcgaggtggagctaatcccataaaaccgat |
| | | | | cgtagtccggatcgcagtctgcaactcgac |
| | | | | tgcgtgaagtcggaatcgctagtaatcgtg |
| | | | | aatcagaatgtcacggtgaatacgttcccg |
| | | | | ggccttgtacacaccgcccgtcacaccatg |
| | | | | ggagtgggttgctccagaagtagctagtct |
| | | | | aaccttcgggggggacggttaccacggagtg |
| | | | | attcatgactggggtg |
| 49 | AF170359 | DNA | *Dechloromarinus chlorophilus* strain NSS | gagtttgatcctggctcagattgaacgctg gcggtatgcttaacacatgcaagtcgaacg gcagcacgagagagcttgctctcttggtgg cgagtggcggacgggtgagtaacgcgtaag aatctgcctggtagtgggggataactcggg gaaactcgagctaataccgcatacgcccta cgggggaaagtgggggaccttcgggcctca cgctattagatgagcttgcgttggattagc tagttggtagggtaatggcctaccaaggcg acgatccatagctggtctgagaggacgatc agccacactgggactgagacacggcccaga ctcctacgggaggcagcagtggggaatatt ggacaatgggcgcaagcctgatccagcaat accgcgtgtgtgaagaaggcctgcgggttg taaagcactttcaattgtgaagaaaagctt ggggctaatatcctcgagtcttgacgttaa cttagaagaagcaccggctaactctgtgc cagcagccgcggtaatacagagggtgcgag cgttaatcggaattactgggcgtaaagcgt gcgtaggcggtttagtaagtcagatgtgaa agccctgggcttaacctgggaactgcattt gaaactgctgaactagagtgtggtagaggg aagtggaattccgggtgtagcggtgaaatg cgtagatatccggaggaacaccagtggcga aggcgacttcctggaccaacactgacgctg aggtacgaaagcgtgggtagcaaacaggat tagataccctggtagtccacgccgtaaacg atgtcaactagttgttgggagcattttggc ttttagtaacgtagctaacgcgataagttg accgcctggggagtacggccgcaaggttaa aactcaaaggaattgacggggcccgcaca agcggtggagcatgtggtttaattcgatgc aacgcgaagaaccttaccagcccttgacat cctgcgaacttctagagatagattggtgc tttcgggaacgcagtgacaggtgctgcatg gctgtcgtcagctcgtgtcgtgagatgttg ggttaagtcccgtaacgagcgcaacccttg tccttagttgccagcatttcgggatgggaa ctctagggagactgccggtgataaaccgga ggaaggtggggatgacgtcaagtcatcatg gcccttatgggctgggctacacacgtgcta caatggccggtacagagggccgcaaacccg cgaggggagcaaatctcacaaaaccggtc gtagtccggatcgcagtctgcaactcgact gcgtgaagttggaatcgctagtaatcgcga atcagaatgtcgcggtgaatacgttcccgg gccttgtacacaccgcccgtcacaccatgg gagtgggttgcaaaagaagtaggtagtcta accttcggggagacgcttaccactttgtga ttcatgactggggtgaagtcgtaacaaggt |

-continued

Sequences for sequence listing

| SEQ ID NO: | Genbank Accession No. | Sequence Type | Description | Sequence |
|---|---|---|---|---|
| | | | | a |
| 50 | AF170348 | DNA | A. suillum | agagtttgatcctggctcagattgaacgct<br>ggcggcatgccttacacatgcaagtcgaac<br>ggcagcacgggagcttgctcctggtggcga<br>gtggcgaacgggtgagtaatacatcggaac<br>gtacccaggagtgggggataacgtagcgaa<br>agttacgctaataccgcatattctgtgagc<br>aggaaagcgggggatcgcaagacctcgcgc<br>tcttggagcggccgatgtcggattagctag<br>ttggtgaggtaaaagctcaccaaggcgacg<br>atccgtagcaggtctgagaggatgatctgc<br>cacactgggactgagacacggcccagactc<br>ctacgggaggcagcagtggggaattttgga<br>caatgggggcaaccctgatccagccatgcc<br>gcgtgagtgaagaaggccttcggggttgtaa<br>agctctttcggcggggaagaaatggcaacg<br>gctaatatccgttgttgatgacggtacccg<br>cataagaagcaccggctaactacgtgccag<br>cagccgcggtaatacgtagggtgcgagcgt<br>taatcggaattactgggcgtaaagcgtgcg<br>caggcggtttcgtaagacagacgtgaaatc<br>cccgggctcaacctgggaactgcgtttgtg<br>actgcgaggctagagtacggcagaggggg<br>tagaattccacgtgtagcagtgaaatgcgt<br>agagatgtggaggaataccgatggcgaagg<br>cagccccctgggttagtactgacgctcatg<br>cacgaaagcgtggggagcaaacaggattag<br>ataccctcgtagtccacgccctaaacgatg<br>tcaactaggtgttggaagggttaaacctt<br>tagtaccgcagctaacgcgtgaagttgacc<br>gcctggggagtacggccgcaaggttaaaac<br>tcaaaggaattgacggggacccgcacaagc<br>ggtggatgatgtggattaattcgatgcaac<br>gcgaaaaaccttacctaccccttgacatgcc<br>aggaactttccagagatggattggtgcccg<br>aaagggagcctggacacaggtgctgcatgg<br>ctgtcgtcagctcgtgtcgtgagatgttgg<br>gttaagtcccgcaacgagcgcaaccctgt<br>cattaattgccatcattcagttgggcactt<br>taatgagactgccggtgacaaaccggagga<br>aggtggggatgacgtcaagtcctcatggcc<br>cttatgggtagggcttcacacgtcatacaa<br>tggtcggtacagagggttgccaagccgcga<br>ggtggagccaatcccagaaagccgatcgta<br>gtccggatcgcagtctgcaactcgactgcg<br>tgaagtcggaatcgctagtaatcgcggatc<br>agcatgtcgcggtgaatacgttcccgggtc<br>ttgtacacaccgcccgtcacaccatgggag<br>tgggttctaccagaagtagttagcctaacc<br>gtaaggagggcgattaccacggtaggattc<br>atgactggggtgaagtcgtaacaaggtagc<br>cgtatcggaaggtgcggctggatcacctcc<br>tt |
| 51 | AY124797 | DNA | Dechloromonas sp. strain LT-1 | gtttgatcctcgctcagattgaacgctggc<br>ggcatgccttacacatgcaagtcgaacggc<br>agcacggacttcggtctggtggcgagtggc<br>gaacgggtgagtaatgcatcggaacgtacc<br>cggaagtgggggataactatccgaaaggat<br>ggctaataccgcatattctgtacgcaggaa<br>agaggggggatcttcggacctcttgctttcg<br>gagcggccgatgtcagattagctagttggt<br>ggggtaaaggcctaccaaggcgacgatctg<br>tagcgggtctgagaggatgatccgccacac<br>tggaactgagacacggtccagactcctacg<br>ggaggcagcagtggggaattttgacaatg<br>ggcgcaagcctgatccagccatgccgcgtg<br>agtgaagaaggccttcgggttgtaaagctc<br>tttcggccgggaaaaaatcggtgaggctaa<br>tatcctcatcggatgatggtaccggactaa<br>gaagcaccggctaactacgtgccagcagcc<br>gcggtaatacgtagggtgcgagcgttaatc |

Sequences for sequence listing

| SEQ ID NO: | Genbank Accession No. | Sequence Type | Description | Sequence |
|---|---|---|---|---|
| | | | | ggaattactgggcgtaaagcgtgcgcaggc<br>ggttttttaagacaggcgtgaaatccccgg<br>gcttaacctgggaactgcgtttgtgactgg<br>aaggctagagtacggcagagggggtggaa<br>ttccacgtgtagcagtgaaatgcgtagaga<br>tgtggaggaacaccaatggcgaaggcagcc<br>ccctgggtcgatactgacgctcatgcacga<br>aagcgtggggagcaaacaggattagatacc<br>ctggtagtccacgccctaaacgatgtcaac<br>taggtgttgggtgggtaaaaccatttagta<br>ccggagctaacgcgtgaagttgaccgcctg<br>gggagtacggccgcaaggttaaaactcaaa<br>ggaattgacggggacccgcacaagcggtgg<br>atgatgtggattaattcgatgcaacgcgaa<br>aaaccttacctacccttgacatgccaggaa<br>cttgccagagatggcttggtgcccgaaagg<br>gagcctggacacaggtgctgcatggctgtc<br>gtcagctcgtgtcgtgagatgttgggttaa<br>gtcccgcaacgagcgcaacccttgtcgtta<br>attgccatcattaagttgggcactttaacg<br>agactgccggtgacaaaccggaggaaggtg<br>gggatgacgtcaagtcctcatggcccttat<br>gggtagggcttcacacgtcatacaatggtc<br>ggtacagagggttgccaagccgcgaggtgg<br>agccaatcccagaaagccgatcgtagtccg<br>gatcgtaggctgcaactcgcctgcgtgaag<br>tcggaatcgctagtaatcgcggatcagcat<br>gtcgcggtgaatacgttcccgggtcttgta<br>cacaccgcccgtcacaccatgggagcgggt<br>tccgccagaagtaggtagcctaaccgcaag<br>ggggcgcttaccacggcggggttcgtgac<br>tggggtgaagtcgtaacaaggtagccgtag<br>gggaacctgcggctggatcacct |
| 52 | X72724 | DNA | I. dechloratans | attgaacgctggcggcatgccttacacatg<br>caagtcgaacggtaagcgggcaacctggcg<br>acgagtggcgaacgggtgagtaatgcatcg<br>gaacgtgcccagtagtgggggatagcccgg<br>cgaaagccggattaataccgcatacgacct<br>gagggtgaaaggggggatcgcaagacctc<br>tcgctattggagcggccgatgtcagattag<br>gtagttggtggggtaaaggcctaccaagcc<br>gacgatctgtagctggtctgagaggacgac<br>cagccacactgggactgagacacgcccag<br>actcctacgggaggcagcagtggggaattt<br>tggacaatgggcgaagcytgatccagcca<br>tgccgcgtgcggaagaaggccttcgggttg<br>taaaccgcttttgtcagggaagaaatcttc<br>tgggctaatacctcgggaggatgacggtac<br>ctgaagaataagcaccggctaactacgtgc<br>cagcagccgcggtaatacgtagggtgcaag<br>cgttaatcggaattactgggcgtaaagcgt<br>gcgcaggcggttttgtaagacagaggtgaa<br>atccccgggctcaacctgggaactgccttt<br>gtgactgcaaggcttgagtgcgcagagggg<br>gatggaattccgcgtgtagcagtgaaatgc<br>gtagatatgcggaggaacaccgatggcgaa<br>ggcaatcccctgggcctgcactgacgctca<br>tgcacgaaagcgtggggagcaaacaggatt<br>agatacctggtagtccacgccctaaacga<br>tgtcaactggttgttgggaaggttccttct<br>cagtaacgtagctaacgcgtgaagttgacc<br>gcctggggagtacggccgcaaggttgaaac<br>tcaaaggaattgacggggacccgcacaagc<br>ggtggatgatgtggtttaattcgatgcaac<br>gcgaaaaccttacctacccttgacatggc<br>aggaatcctgaagagatttggagtgctcg<br>aaagagaacctgcacacaggtgctgcatgg<br>ccgtcgtcagctcgtgtcgtgagatgttgg<br>gttaagtcccgcaacgagcgcaacccttgt<br>cattagttgctacgaaagggcactctaatg<br>agactgccggtgacaaaccggaggaaggtg<br>gggatgacgtcaggtcctcatggcccttat |

-continued

Sequences for sequence listing

| SEQ ID NO: | Genbank Accession No. | Sequence Type | Description | Sequence |
|---|---|---|---|---|
| | | | | gggtagggctacacacgtcatacaatggcc |
| | | | | ggtacagagggctgccaayccgcgaggggg |
| | | | | agccaatcccagaaaaccggtcgtagtccg |
| | | | | gatcgcagtctgcaactcgactgcgtgaag |
| | | | | tcggaatcgctagtaatcgcggatcagctt |
| | | | | gccgcggtgaatacgttcccgggtcttgta |
| | | | | cacaccgcccgtcacaccatgggagcgggt |
| | | | | tctgccagaagtagttagcctaaccgcaag |
| | | | | gagggcgattaccacggcagggttcgtgac |
| | | | | tggggtgaagtcgtaacaaggtagccgtat |
| | | | | cggaaggtgcggctggatcacctcctttct |

The present invention is directed to metabolic primers for the detection of perchlorate-reducing bacteria and methods and compositions for use of the same. Certain specific aspects can be described according to the following paragraphs:

Paragraph 1: A composition comprising a first primer and a second primer, wherein the first primer has a nucleic acid sequence that comprises a sequence of SEQ ID NO:1 or SEQ ID NO:11 and the second primer has a nucleic acid sequence that comprises a sequence of SEQ ID NO:2 or SEQ ID NO:12, wherein said first and second primers are capable of hybridizing to a perchlorate reductase gene.

Paragraph 2: The composition of paragraph 1, further comprising a third primer and a fourth primer, wherein the third primer has a nucleic acid sequence that comprises a sequence of SEQ ID NO:3 and the fourth primer has a nucleic acid sequence that comprises a sequence of SEQ ID NO:4, wherein said third and fourth primers are capable of hybridizing to a perchlorate reductase gene.

Paragraph 3: The composition of paragraph 1, further comprising a third primer and a fourth primer, wherein the third primer has a nucleic acid sequence that comprises a sequence of SEQ ID NO:5 or SEQ ID NO:13 and the fourth primer has a nucleic acid sequence that comprises a sequence of SEQ ID NO:6 or SEQ ID NO:14, wherein said third and fourth primers are capable of hybridizing to a perchlorate reductase gene.

Paragraph 4: The composition of paragraph 1, further comprising a third primer and a fourth primer wherein the third primer has a nucleic acid sequence that comprises a sequence of SEQ ID NO:7 and the fourth primer has a nucleic acid sequence that comprises a sequence of SEQ ID NO:8 wherein said third and fourth primers are capable of hybridizing to a perchlorate reductase gene.

Paragraph 5: A composition comprising a first primer and a second primer, wherein the first primer has a nucleic acid sequence that comprises a sequence of SEQ ID NO:3 and the second primer has a nucleic acid sequence that comprises a sequence of SEQ ID NO:4, wherein said first and second primers are capable of hybridizing to a perchlorate reductase gene.

Paragraph 6: The composition of paragraph 5, further comprising a third primer and a fourth primer, wherein the third primer has a nucleic acid sequence that comprises a sequence of SEQ ID NO:5 or SEQ ID NO:13 and the fourth primer has a nucleic acid sequence that comprises a sequence of SEQ ID NO:6 or SEQ ID NO:14, wherein said third and fourth primers are capable of hybridizing to a perchlorate reductase gene.

Paragraph 7: The composition of paragraph of paragraph 5, further comprising a third primer and a fourth primer, wherein the third primer has a nucleic acid sequence that comprises a sequence of SEQ ID NO:7 and the fourth primer has a nucleic acid sequence that comprises a sequence of SEQ ID NO:8 wherein said third and fourth primers are capable of hybridizing to a perchlorate reductase gene.

Paragraph 8: A composition comprising a first primer and a second primer, wherein the first primer has a nucleic acid sequence that comprises a sequence of SEQ ID NO:5 or SEQ ID NO:13 and the second primer has a nucleic acid sequence that comprises a sequence of SEQ ID NO:6 or SEQ ID NO:14, wherein said first and second primers are capable of hybridizing to a perchlorate reductase gene.

Paragraph 9: The composition of paragraph of paragraph 8, further comprising a third primer and a fourth primer, wherein the third primer has a nucleic acid sequence that comprises a sequence of SEQ ID NO:7 and the fourth primer has a nucleic acid sequence that comprises a sequence of SEQ ID NO:8 wherein said third and fourth primers are capable of hybridizing to a perchlorate reductase gene.

Paragraph 10: The composition of paragraph 2, further comprising a fifth primer and a sixth primer, wherein the fifth primer has a nucleic acid sequence that comprises a sequence of SEQ ID NO:5 or SEQ ID NO:13 and the sixth primer has a nucleic acid sequence that comprises a sequence of SEQ ID NO:6 or SEQ ID NO:14, wherein said fifth and sixth primers are capable of hybridizing to a perchlorate reductase gene.

Paragraph 11: The composition of paragraph 10, further comprising a seventh primer and an eighth primer, wherein the seventh primer has a nucleic acid sequence that comprises a sequence of SEQ ID NO:7 and the eighth primer has a nucleic acid sequence that comprises a sequence of SEQ ID NO:8, wherein said seventh and eighth primers are capable of hybridizing to a perchlorate reductase gene.

Paragraph 12: The composition of paragraph 9 further comprising a fifth primer and a sixth primer, wherein the fifth primer has a nucleic acid sequence that comprises a sequence of SEQ ID NO:7 and the sixth primer has a nucleic acid sequence that comprises a sequence of SEQ ID NO:8, wherein said fifth and sixth primers are capable of hybridizing to a perchlorate reductase gene.

Paragraph 13: The composition of any of paragraphs 1 through 12, wherein each of said primers each independently comprise between 20 and 30 nucleotide bases in length.

Paragraph 14: The composition of any of paragraphs 1 through 12, wherein each of said primers each independently comprise between 20 and 40 nucleotide bases in length.

Paragraph 15: The composition of any of paragraphs 1 through 12, wherein each of said primers each independently comprise between 20 and 50 nucleotide bases in length.

Paragraph 16: The composition of paragraph 1 wherein the perchlorate reductase gene is from dissimilatory perchlorate-reducing bacteria (DPRB) species.

Paragraph 17: The composition of paragraph 16, wherein said DPRB is a bacterium from the *Dechloromonas* spp., *Azoarcus* spp., *Dechlorospirillum* spp., *Dechloromarinus* spp., *Ideonella* spp., *Magnetospirillum* spp., *Pseudomonas* spp., *Rhodocyclus* spp., *Rhodospirillum* spp., *Azospirillum* spp., *Wolinella* spp., *Xanthomonas* spp.

Paragraph 18: The composition of paragraph 17, wherein said DPRB is selected from the group consisting of *Dechloromonas agitate, Dechloromonas aromatica, Azospira suillum, Dechlorospirillum anomalous, Dechloromarinus chlorophilus, Ideonella dechloratans*, and *Magnetospirillum magnetotacticum*.

Paragraph 19: The composition of any of paragraphs 1 through 18, wherein the primer is detectably labeled.

Paragraph 20: An oligonucleotide primer pair wherein the first primer of the primer pair comprises a sequence of SEQ ID NO:1 or SEQ ID NO:11 and the second primer of the primer pair comprises a sequence of SEQ ID NO:2 or SEQ ID NO:12.

Paragraph 21: An oligonucleotide primer pair wherein the first primer of the primer pair comprises a sequence of SEQ ID NO:3 and the second primer of the primer pair comprises a sequence of SEQ ID NO:4.

Paragraph 22: An oligonucleotide primer pair wherein the first primer of the primer pair comprises a sequence of SEQ ID NO:5 or SEQ ID NO:13 and the second primer of the primer pair comprises a sequence of SEQ ID NO:6 or SEQ ID NO:14.

Paragraph 23: An oligonucleotide primer pair wherein the first primer of the primer pair comprises a sequence of SEQ ID NO:7 and the second primer of the primer pair comprises a sequence of SEQ ID NO:8.

Paragraph 24: The oligonucleotide primer pair of any of paragraphs 20 through 23 wherein at least one of the primers in the primer pair is detectably labeled.

Paragraph 25: An oligonucleotide primer which has the nucleotide sequence defined in any one of SEQ ID NOs: 1, 2, 3, 4, 5, 6, 7, 8, 11, 12, 13, or 14.

Paragraph 26: The oligonucleotide primer of paragraph 25, wherein said oligonucleotide comprises between 20 and 50 nucleotide bases.

Paragraph 27: The oligonucleotide primer of any of paragraphs 25 through 26 wherein the primer is detectably labeled.

Paragraph 28: The oligonucleotide of paragraph 27, wherein the primer is labeled with an epitope, fluorophore, metal particle, enzyme, carbohydrate, polypeptide, radioactive isotope, dye, biotin, or digitonin.

Paragraph 29: The oligonucleotide primer pair of paragraph 24, wherein the primer is labeled with an epitope, fluorophore, metal particle, enzyme, carbohydrate, polypeptide, radioactive isotope, dye, biotin, or digitonin Paragraph 30: The composition of paragraph 19, wherein the primer is labeled with an epitope, fluorophore, metal particle, enzyme, carbohydrate, polypeptide, radioactive isotope, dye, biotin, or digitonin.

Paragraph 31: A method of detecting the presence of perchlorate reducing bacteria in a sample comprising: (a) subjecting DNA of bacterial cells in said sample to a first polymerase chain reaction amplification using a pair of primers of paragraph 20, paragraph 21, paragraph 22 or paragraph 23; and (b) detecting the product or products of said first polymerase chain reaction amplification, thereby identifying the presence of said perchlorate-reducing bacteria in said sample.

Paragraph 32: The method of paragraph 31, further comprising subjecting said DNA to a second polymerase chain reaction amplification using a pair of primers of paragraph 20, paragraph 21, paragraph 22 or paragraph 23, that is a different primer set than the primer set that is used in first polymerase chain reaction amplification; and detecting the product or products of said second polymerase chain reaction amplification thereby identifying the presence of said perchlorate-reducing bacteria in said sample.

Paragraph 33: A method of detecting the presence of perchlorate reducing bacteria in a sample comprising: (a) subjecting DNA from said sample to a first polymerase chain reaction amplification using a pair of primers of paragraph 20, paragraph 21, paragraph 22 or paragraph 23; and (b) detecting the product or products of said first polymerase chain reaction amplification, thereby identifying the presence of said perchlorate-reducing bacteria in said sample.

Paragraph 34: A method of detecting the presence of perchlorate-reducing bacteria in a sample comprising: (a) subjecting DNA from said sample to a first polymerase chain reaction amplification using a pair of primers of paragraph 20, paragraph 21, paragraph 22 or paragraph 23; (b) isolating the amplification products from step (a); (c) using the amplification products isolated in step (b) as a template for a second polymerase chain reaction amplification using a second primer pair from paragraph 20, paragraph 21, paragraph 22 or paragraph 23 that is different from the primer pair used in the first polymerase chain reaction; and (d) detecting the product or products of said second polymerase chain reaction amplification, thereby identifying the presence of said perchlorate-reducing bacteria in said sample.

35. A method of detecting the presence of perchlorate-reducing bacteria in a sample comprising: (a) subjecting DNA from said sample to a first polymerase chain reaction amplification using a pair of primers of paragraph 20, paragraph 21, paragraph 22 or paragraph 23; (b) isolating the amplification products from step (a); (c) using the amplification products isolated in step (b) as a template for a second polymerase chain reaction amplification using a second primer pair from paragraph 20, paragraph 21, paragraph 22 or paragraph 23 that is different from the primer pair used in the first polymerase chain reaction; (d) isolating the amplification products from step (c); (e) using the amplification products isolated in step (d) as a template for a third polymerase chain reaction amplification using a third primer pair from paragraph 20, paragraph 21, paragraph 22 or paragraph 23 that is different from the primer pair used in the first or the second polymerase chain reaction; and (f) detecting the product or products of said third polymerase chain reaction amplification, thereby identifying the presence of said perchlorate-reducing bacteria in said sample.

Paragraph 36: A method of detecting the presence of perchlorate-reducing bacteria in a sample comprising: (a) subjecting DNA from said sample to a first polymerase chain reaction amplification using a pair of primers of paragraph 20, paragraph 21, paragraph 22 or paragraph 23; (b) isolating the amplification products from step (a); (c) using the amplification products isolated in step (b) as a template for a second polymerase chain reaction amplification using a second primer pair from paragraph 20, paragraph 21, paragraph 22 or paragraph 23 that is different from the primer pair used in the first polymerase chain reaction; (d) isolating the amplification products from step (c); (e) using the amplification products isolated in step (d) as a template for a third polymerase chain reaction amplification using a third primer pair from paragraph 20, paragraph 21, paragraph 22 or paragraph 23 that is different from the first primer pair used in the first or the second polymerase chain reaction; (f) isolating the amplification products from step (e); (g) using the amplification products isolated in step (d) as a template for a fourth polymerase chain reaction amplification using a fourth primer pair from paragraph 20, paragraph 21, paragraph 22 or paragraph 23 that is different from the primer pair used in the first second or the third polymerase chain reaction; and (h) detecting the product or products of said third polymerase chain reaction amplification, thereby identifying the presence of said perchlorate-reducing bacteria in said sample.

Paragraph 37: The method of any one of paragraphs 31 through 36 wherein DNA is isolated from bacterial lysates from said sample prior to step (a).

Paragraph 38: The method of any of paragraphs 31 through 37, wherein said sample is water sample.

Paragraph 39: The method of any of paragraphs 31 through 38, wherein said sample is a soil sample.

Paragraph 40: The method of paragraph 38, wherein said water sample is collected from a water supply that has been contaminated with perchlorate.

Paragraph 41: The method of paragraph 39, wherein said soil sample is collected from land that has been contaminated with perchlorate.

Paragraph 42: The method of paragraph 40 or 41, wherein said perchlorate contamination is a result of waste disposal from paper mill waste, airbag production, firework manufacture and use, fertilizer manufacture and use.

Paragraph 43: A method of determining whether a bioremediation formulation that comprises bacteria will be effective at decreasing perchlorate contamination comprising: (a) subjecting DNA from said bioremediation formulation to a first polymerase chain reaction amplification using a pair of primers of paragraph 20, paragraph 21, paragraph 22 or paragraph 23; and (b) detecting the product or products of said first polymerase chain reaction amplification, wherein the presence of said amplification products indicates the presence of perchlorate reducing bacteria in bioremediation formulation thereby indicating that said formulation is effective at reducing perchlorate contamination.

Paragraph 44: The method of paragraph 43, further comprising subjecting said DNA to a second polymerase chain reaction amplification using a second pair of primers of paragraph 20, paragraph 21, paragraph 22 or paragraph 23 that is different from the first pair of primers; and detecting the presence of perchlorate-reducing bacteria in said bioremediation formulation by visualizing the product or products of said second polymerase chain reaction amplification, wherein the presence of said amplification products indicates that said formulation is effective at reducing perchlorate contamination.

Paragraph 45: The method of paragraph 44, further comprising subjecting said DNA to a third polymerase chain reaction amplification using a third pair of primers of paragraph 20, paragraph 21, paragraph 22 or paragraph 23 that is different from the first and the second pair of primers; and detecting the presence of perchlorate-reducing bacteria in said bioremediation formulation by visualizing the product or products of said third polymerase chain reaction amplification, wherein the presence of said amplification products indicates that said formulation is effective at reducing perchlorate contamination.

Paragraph 46: The method of paragraph 45, further comprising subjecting said DNA to a fourth polymerase chain reaction amplification using a fourth pair of primers of paragraph 20, paragraph 21, paragraph 22 or paragraph 23 that is different from the first, second and the third pair of primers; and detecting the presence of perchlorate-reducing bacteria in said bioremediation formulation by visualizing the product or products of said fourth polymerase chain reaction amplification, wherein the presence of said amplification products indicates that said formulation is effective at reducing perchlorate contamination.

Paragraph 47: A method of determining whether a bioremediation formulation that comprises bacteria will be effective at decreasing perchlorate contamination comprising (a) subjecting said DNA from said bioremediation formulation to a first polymerase chain reaction amplification using a pair of primers of paragraph 20, paragraph 21, paragraph 22 or paragraph 23; (b) isolating the amplification products from step (a); (c) using the amplification products isolated in step (b) as a template for a second polymerase chain reaction amplification using a primer pair from paragraph 20, paragraph 21, paragraph 22 or paragraph 23 that is different from the pair of primers used in the first polymerase chain reaction amplification; and (d) detecting said perchlorate-reducing bacteria by visualizing the product or products of said second polymerase chain reaction amplification.

Paragraph 48: A method of determining whether a bioremediation formulation that comprises bacteria will be effective at decreasing perchlorate contamination comprising: (a) subjecting said DNA from said bioremediation formulation to a first polymerase chain reaction amplification using a pair of primers of paragraph 20, paragraph 21, paragraph 22 or paragraph 23; (b) isolating the amplification products from step (a); (c) using the amplification products isolated in step (b) as a template for a second polymerase chain reaction amplification using a primer pair from paragraph 20, paragraph 21, paragraph 22 or paragraph 23 that is different from the pair of primers used in the first polymerase chain reaction amplification; (d) isolating the amplification products from step (c); (e) using the amplification products isolated in step (d) as a template for a third polymerase chain reaction amplification using a primer pair from paragraph 20, paragraph 21, paragraph 22 or paragraph 23 that is different from the pair of primers used in the first and second polymerase chain reaction amplification; and (f) detecting said perchlorate-reducing bacteria by visualizing the product or products of said second polymerase chain reaction amplification.

Paragraph 49. A method of determining whether a bioremediation formulation that comprises bacteria will be effective at decreasing perchlorate contamination comprising (a) subjecting said DNA from said bioremediation formulation to a first polymerase chain reaction amplification using a pair of primers of paragraph 20, paragraph 21, paragraph 22 or paragraph 23; (b) isolating the amplification products from step (a); (c) using the amplification products isolated in step (b) as a template for a second polymerase chain reaction amplification using a primer pair from paragraph 20, paragraph 21, paragraph 22 or paragraph 23 that is different from the pair of primers used in the first polymerase chain reaction amplification; (d) isolating the amplification products from step (c); (e) using the amplification products isolated in step (d) as a template for a third polymerase chain reaction amplification using a primer pair from paragraph 20, paragraph 21, paragraph 22 or paragraph 23 that is different from the pair of primers used in the first and second polymerase chain reaction amplification; (f) isolating the amplification products from step (e); (g) using the amplification products isolated in step (f) as a template for a fourth polymerase chain reaction amplification using a primer pair from paragraph 20, paragraph 21, paragraph 22 or paragraph 23 that is different from the pair of primers used in the first second and third polymerase chain reaction amplification; and (h) detecting said perchlorate-reducing bacteria by visualizing the product or products of said second polymerase chain reaction amplification.

Paragraph 50: The method of any of paragraphs 43 through 49, wherein said method further comprises determining the presence of chlorite dismutase in said sample prior to determining the presence of perchlorate reductase in said sample.

Paragraph 51: The method of paragraph 50, wherein said determining the presence of chlorite dismutase in said sample comprises performing polymerase chain reactions using primers selected from the group consisting of SEQ ID NO:15 through SEQ ID NO:24.

Paragraph 52: The method of any of paragraphs 43 through 51 wherein DNA is isolated from a bacterial lysates from said bioremediation formulation prior to step (a).

Paragraph 53: The method of any of paragraphs 43 through 51 wherein said bioremediation formulation is a cocktail of microorganisms that are used to remove contaminants from a sample of soil or water in need of decontamination, wherein said cocktail of microorganisms comprises a mixture of DPRBs.

Paragraph 54: The method of paragraph 53, wherein said cocktail of microorganisms further microorganisms that are denitrifiers.

Paragraph 55: The method of paragraph 53, wherein said cocktail of microorganisms further comprises microorganisms that can degrade toluene, xylene, benzene, petroleum, and creosote.

Paragraph 56: A method of determining whether a sample contains bacteria that is reducing perchlorate in said sample comprising: (a) isolating nucleic acid from said sample; (b) incubating said nucleic acid with a DNase to isolate RNA; (c) performing a reverse transcription reaction on said RNA using one or more of the primers selected from the group consisting of SEQ ID NO:1, 2, 3, 4, 5, 6, 7, 8, 11, 12, 13 and 14; and (d) detecting the product or products of said reverse transcription reaction that are expressing perchlorate reductase, thereby identifying the presence of bacteria in said sample that are expressing perchlorate reductase for reducing the perchlorate content of said sample.

Paragraph 57: A method of determining whether a sample contains bacteria that is reducing perchlorate in said sample comprising: (a) isolating nucleic acid from said sample; (b) incubating said nucleic acid with a DNase to isolate RNA; (c) performing a reverse transcriptase reaction on said RNA using one or more of the primers selected from the group consisting of SEQ ID NO:1, 2, 3, 4, 5, 6, 7, 8, 11, 12, 13 and 14; (d) isolating the reaction products from step (c); (e) using the reaction products isolated in step (d) as a template for a polymerase chain reaction amplification using a primer pair from paragraph 20, paragraph 21, paragraph 22 or paragraph 23; and (f) detecting the product or products of said polymerase chain reaction amplification of step (e), thereby identifying the presence of bacteria in said sample that are expressing perchlorate reductase for reducing the perchlorate content of said sample.

Paragraph 58: The method of any of paragraphs 56 or 57, wherein said method further comprises determining the presence of chlorite dismutase in said sample prior to determining the presence of perchlorate reductase in said sample.

Paragraph 59: The method of paragraph 58, wherein said determining the presence of chlorite dismutase in said sample comprises performing polymerase chain reactions using primers selected from the group consisting of SEQ ID NO:15 through SEQ ID NO:24.

Paragraph 60: The method of paragraph 59, further comprising isolating the amplification products of step (e) prior to performing step (f) and using said isolated amplification products as a template for a second polymerase chain reaction amplification using a primer pair of paragraph 20, paragraph 21, paragraph 22 or paragraph 23 that is different from the primer pair used in step (e).

Paragraph 61: The method of paragraph 60 further comprising performing a third or fourth polymerase chain reaction amplification using a primer pair of paragraph 20, paragraph 21, paragraph 22 or paragraph 23 that is different from the primer pairs used in the first and second polymerase chain reaction amplifications.

Paragraph 62: A kit for amplifying perchlorate reductase polynucleotide, said kit comprising: composition of any of paragraphs 1 through 19, or an oligonucleotide pair of any of any of paragraphs 20 through 24, or an oligonucleotide of any of paragraphs 25 through 28; and instructions for carrying out the method according to any of paragraphs 31 through 61.

Paragraph 63: The kit of paragraph 62, which further comprises enzymes and nucleotide components of a PCR reaction.

Paragraph 64: The kit of paragraph 62, wherein said kit further comprises a solid support.

Paragraph 65: The kit of paragraph 62, wherein each of said primers is arrayed on said solid support.

Paragraph 66: The kit of paragraph 62, wherein each of the primers are in separate containers.

Paragraph 67: The kit of any one of paragraphs 62 through 66 wherein said kit further comprises an oligonucleotide primer or primer pair for amplifying chlorite dismutase.

Paragraph 68: The kit of paragraph 67 wherein said oligonucleotide primer is selected from the group consisting of SEQ ID NO:15 through SEQ ID NO:24.

Paragraph 69: A library of primers for the detection of a perchlorate reductase gene from DPRB, said library comprising at least 6 primers derived from the sequences set forth in SEQ ID NO:1, 2, 3, 4, 5, 6, 7, 8, 11, 12 13, or 14.

Paragraph 70: A library of primers for the detection of DPRB, said library comprising at least 6 primers derived from the sequences set forth in SEQ ID NO:1, 2, 3, 4, 5, 6, 7, 8, 11, 12, 13, or 14 for detecting perchlorate reductase and the sequences set forth in SEQ ID NO:15, 16, 17, 18, 19, 20, 21, 22, 23, or 24 for detecting chlorite dismutase.

---

What is claimed is:

1. A composition comprising a first primer and a second primer, wherein the first primer has a nucleic acid sequence that comprise the sequence of SEQ ID NO:1 or SEQ ID NO:11 and the second primer has a nucleic acid sequence that comprise the sequence of SEQ ID NO:2 or SEQ ID NO:12, wherein said first and second primers are capable of hybridizing to a perchlorate reductase gene.

2. The composition of claim 1, further comprising a third primer and a fourth primer, wherein the third primer has a nucleic acid sequence that comprise the sequence of SEQ ID NO:3 and the fourth primer has a nucleic acid sequence that comprise the sequence of SEQ ID NO:4, wherein said third and fourth primers are capable of hybridizing to a perchlorate reductase gene.

3. The composition of claim 2, further comprising a fifth primer and a sixth primer, wherein the fifth primer has a nucleic acid sequence that comprise the sequence of SEQ ID NO:5 or SEQ ID NO:13 and the sixth primer has a nucleic acid sequence that comprise the sequence of SEQ ID NO:6 or SEQ ID NO:14, wherein said fifth and sixth primers are capable of hybridizing to a perchlorate reductase gene.

4. The composition of claim 3, further comprising a seventh primer and an eighth primer, wherein the seventh primer has a nucleic acid sequence that comprise the sequence of SEQ ID NO:7 and the eighth primer has a nucleic acid sequence that comprise the sequence of SEQ ID NO:8, wherein said seventh and eighth primers are capable of hybridizing to a perchlorate reductase gene.

5. The composition of claim 1, further comprising a third primer and a fourth primer, wherein the third primer has a nucleic acid sequence that comprise the sequence of SEQ ID NO:5 or SEQ ID NO:13 and the fourth primer has a nucleic acid sequence that comprise the sequence of SEQ ID NO:6 or SEQ ID NO:14, wherein said third and fourth primers are capable of hybridizing to a perchlorate reductase gene.

6. The composition of claim 1, further comprising a third primer and a fourth primer wherein the third primer has a nucleic acid sequence that comprise the sequence of SEQ ID NO:7 and the fourth primer has a nucleic acid sequence that comprise the sequence of SEQ ID NO:8 wherein said third and fourth primers are capable of hybridizing to a perchlorate reductase gene.

7. The composition of claim 1, wherein each of said primers each independently comprise between 20 and 50 nucleotide bases in length.

8. The composition of claim 1 wherein the perchlorate reductase gene is from dissimilatory perchlorate-reducing bacteria (DPRB) species.

9. The composition of claim 8, wherein said DPRB is a bacterium from the *Dechloromonas* spp., *Azoarcus* spp., *Dechlorospirillum* spp., *Dechlorornarinus* spp., *Ideonella* spp., *Magnetospirillum* spp., *Pseudomonas* spp., *Rhodacyclus* spp., *Rhodospirdlum* spp., *Azospirillum* spp., *Wolinella* spp., and *Xanthomonas* spp.

10. The composition of claim 9, wherein said DPRB is selected from the group consisting of *Dechloromonas agitate, Dechloromonas aromatica, Azospira suillum, Dechlorospirillum anomalous, Dechloromarinus chlorophulus, Ideonella dechloratans*, and *Magnetospirillum magnetotacticum*.

11. The composition of claim 1, wherein the primer is detectably labeled.

12. A composition comprising a first primer and a second primer, wherein the first primer has a nucleic acid sequence that comprise the sequence of SEQ ID NO:3 and the second primer has a nucleic acid sequence that comprise the sequence of SEQ ID NO:4, wherein said first and second primers are capable of hybridizing to a perchlorate reductase gene.

13. The composition of claim 12, further comprising a third primer and a fourth primer, wherein the third primer has a nucleic acid sequence that comprise the sequence of SEQ ID NO:5 or SEQ ID NO:13 and the fourth primer has a nucleic acid sequence that comprise the sequence of SEQ ID NO:6 or SEQ ID NO:14, wherein said third and fourth primers are capable of hybridizing to a perchlorate reductase gene.

14. The composition of claim of claim 12, further comprising a third primer and a fourth primer, wherein the third primer has a nucleic acid sequence that comprise the sequence of SEQ ID NO:7 and the fourth primer has a nucleic acid sequence that comprise the sequence of SEQ ID NO:8 wherein said third and fourth primers are capable of hybridizing to a perchlorate reductase gene.

15. A composition comprising a first primer and a second primer, wherein the first primer has a nucleic acid sequence that comprise the sequence of SEQ ID NO:5 or SEQ ID NO:13 and the second primer has a nucleic acid sequence that comprise the sequence of SEQ ID NO:6 or SEQ ID NO: 14, wherein said first and second primers are capable of hybridizing to a perchlorate reductase gene.

16. The composition of claim of claim 15, further comprising a third primer and a fourth primer, wherein the third primer has a nucleic acid sequence that comprise the sequence of SEQ ID NO:7 and the fourth primer has a nucleic acid sequence that comprise the sequence of SEQ ID NO:8 wherein said third and fourth primers are capable of hybridizing to a perchlorate reductase gene.

17. The composition of claim 16 further comprising a fifth primer and a sixth primer, wherein the fifth primer has a nucleic acid sequence that comprise the sequence of SEQ ID NO:7 and the sixth primer has a nucleic acid sequence that comprise the sequence of SEQ ID NO:8, wherein said fifth and sixth primers are capable of hybridizing to a perchlorate reductase gene.

18. An oligonucleotide primer pair wherein:
the first primer of the primer pair comprise the sequence of SEQ ID NO:1 or SEQ ID NO:11 and the second primer of the primer pair comprise the sequence of SEQ ID NO:2 or SEQ ID NO:12.

19. The oligonucleotide primer pair of claim 18 wherein at least one of the primers in the primer pair is detectably labeled.

* * * * *

SEQUENCE LISTING

```
<160> NUMBER OF SEQ ID NOS: 57

<210> SEQ ID NO 1
<211> LENGTH: 21
<212> TYPE: DNA
<213> ORGANISM: Artificial sequence
<220> FEATURE:
<223> OTHER INFORMATION: Synthetic primer
```

```
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 1
gcnccnccng tngcnttyat g                                            21

<210> SEQ ID NO 2
<211> LENGTH: 21
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 2
rtcrttnacy tcngcutgda t                                            21

<210> SEQ ID NO 3
<211> LENGTH: 19
<212> TYPE: DNA
<213> ORGANISM: Artificial sequence
<220> FEATURE:
<223> OTHER INFORMATION: Synthetic primer

<400> SEQUENCE: 3
acagcgabbt gctddtgcg                                               19

<210> SEQ ID NO 4
<211> LENGTH: 19
<212> TYPE: DNA
<213> ORGANISM: Artificial sequence
<220> FEATURE:
<223> OTHER INFORMATION: Synthetic primer

<400> SEQUENCE: 4
vgccgaaggv adaaccabv                                               19

<210> SEQ ID NO 5
<211> LENGTH: 21
<212> TYPE: DNA
<213> ORGANISM: Artificial sequence
<220> FEATURE:
<223> OTHER INFORMATION: Synthetic primer
```

```
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 5
gayccngcnc tngarggnaa r                                         21

<210> SEQ ID NO 6
<211> LENGTH: 18
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 6
ccadatngtn gtytgrca                                             18

<210> SEQ ID NO 7
<211> LENGTH: 23
<212> TYPE: DNA
<213> ORGANISM: Artificial sequence
<220> FEATURE:
<223> OTHER INFORMATION: Synthetic primer

<400> SEQUENCE: 7
agaccacbat ctggacctat gtc                                       23

<210> SEQ ID NO 8
<211> LENGTH: 22
<212> TYPE: DNA
<213> ORGANISM: Artificial sequence
<220> FEATURE:
<223> OTHER INFORMATION: Synthetic primer

<400> SEQUENCE: 8
ggvadaacca bvtcvgaata ya                                        22

<210> SEQ ID NO 9
<211> LENGTH: 11
<212> TYPE: DNA
<213> ORGANISM: Artificial sequence
<220> FEATURE:
<223> OTHER INFORMATION: Synthetic primer

<400> SEQUENCE: 9
gcgcggaatt c                                                    11
```

```
<210> SEQ ID NO 10
<211> LENGTH: 12
<212> TYPE: DNA
<213> ORGANISM: Artificial sequence
<220> FEATURE:
<223> OTHER INFORMATION: Synthetic primer

<400> SEQUENCE: 10
gcgcgcaagc tt                                                              12

<210> SEQ ID NO 11
<211> LENGTH: 21
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, t, or inosine
<220> FEATURE:
<221> NAME/KEY: misc_feature
<222> LOCATION: (6)..(6)
<223> OTHER INFORMATION: n is a, c, g, t, or inosine
<220> FEATURE:
<221> NAME/KEY: misc_feature
<222> LOCATION: (9)..(9)
<223> OTHER INFORMATION: n is a, c, g, t, or inosine
<220> FEATURE:
<221> NAME/KEY: misc_feature
<222> LOCATION: (12)..(12)
<223> OTHER INFORMATION: n is a, c, g, t, or inosine
<220> FEATURE:
<221> NAME/KEY: misc_feature
<222> LOCATION: (15)..(15)
<223> OTHER INFORMATION: n is a, c, g, t, or inosine

<400> SEQUENCE: 11
gcnccnccng tngcnttyat g                                                    21

<210> SEQ ID NO 12
<211> LENGTH: 21
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, t, or inosine
<220> FEATURE:
<221> NAME/KEY: misc_feature
<222> LOCATION: (13)..(13)
<223> OTHER INFORMATION: n is a, c, g, t, or inosine

<400> SEQUENCE: 12
rtcrttnacy tcngcrtgda t                                                    21

<210> SEQ ID NO 13
<211> LENGTH: 21
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, t, or inosine
<220> FEATURE:
<221> NAME/KEY: misc_feature
<222> LOCATION: (9)..(9)
<223> OTHER INFORMATION: n is a, c, g, t, or inosine
```

```
<220> FEATURE:
<221> NAME/KEY: misc_feature
<222> LOCATION: (12)..(12)
<223> OTHER INFORMATION: n is a, c, g, t, or inosine
<220> FEATURE:
<221> NAME/KEY: misc_feature
<222> LOCATION: (18)..(18)
<223> OTHER INFORMATION: n is a, c, g, t, or inosine

<400> SEQUENCE: 13
gayccngcnc tngarggnaa r                                             21

<210> SEQ ID NO 14
<211> LENGTH: 18
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, t, or inosine
<220> FEATURE:
<221> NAME/KEY: misc_feature
<222> LOCATION: (10)..(10)
<223> OTHER INFORMATION: n is a, c, g, t, or inosine

<400> SEQUENCE: 14
ccadatngtn gtytgrca                                                 18

<210> SEQ ID NO 15
<211> LENGTH: 26
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 15
garcgcaarr gngcngcngm ngargt                                        26

<210> SEQ ID NO 16
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or t

<400> SEQUENCE: 16
tcraartang tdatraartc                                               20
```

```
<210> SEQ ID NO 17
<211> LENGTH: 22
<212> TYPE: DNA
<213> ORGANISM: Artificial sequence
<220> FEATURE:
<223> OTHER INFORMATION: Synthetic primer

<400> SEQUENCE: 17
tygavaarca yaaggahaav gt                                              22

<210> SEQ ID NO 18
<211> LENGTH: 20
<212> TYPE: DNA
<213> ORGANISM: Artificial sequence
<220> FEATURE:
<223> OTHER INFORMATION: Synthetic primer

<400> SEQUENCE: 18
gagtggtava ryttvcgytt                                                 20

<210> SEQ ID NO 19
<211> LENGTH: 26
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 19
gancgnaann gngcngcngn ngangt                                          26

<210> SEQ ID NO 20
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
```

```
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 20
tcnaantang tnatnaantc                                              20

<210> SEQ ID NO 21
<211> LENGTH: 26
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, t, or inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is a, c, g, t, or inosine
<220> FEATURE:
<221> NAME/KEY: misc_feature
<222> LOCATION: (21)..(21)
<223> OTHER INFORMATION: n is a, c, g, t, or inosine

<400> SEQUENCE: 21
garcgcaarr gngcngcngm ngargt                                       26

<210> SEQ ID NO 22
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, t, or inosine

<400> SEQUENCE: 22
tcraartang tvatraartc                                              20

<210> SEQ ID NO 23
<211> LENGTH: 26
<212> TYPE: DNA
<213> ORGANISM: Artificial sequence
<220> FEATURE:
<223> OTHER INFORMATION: Synthetic primer
```

```
<220> FEATURE:
<221> NAME/KEY: misc_feature
<222> LOCATION: (3)..(3)
<223> OTHER INFORMATION: n is a, c, g, t, or inosine
<220> FEATURE:
<221> NAME/KEY: misc_feature
<222> LOCATION: (6)..(6)
<223> OTHER INFORMATION: n is a, c, g, t, or inosine
<220> FEATURE:
<221> NAME/KEY: misc_feature
<222> LOCATION: (9)..(10)
<223> OTHER INFORMATION: n is a, c, g, t, or inosine
<220> FEATURE:
<221> NAME/KEY: misc_feature
<222> LOCATION: (12)..(12)
<223> OTHER INFORMATION: n is a, c, g, t, or inosine
<220> FEATURE:
<221> NAME/KEY: misc_feature
<222> LOCATION: (15)..(15)
<223> OTHER INFORMATION: n is a, c, g, t, or inosine
<220> FEATURE:
<221> NAME/KEY: misc_feature
<222> LOCATION: (18)..(18)
<223> OTHER INFORMATION: n is a, c, g, t, or inosine
<220> FEATURE:
<221> NAME/KEY: misc_feature
<222> LOCATION: (20)..(21)
<223> OTHER INFORMATION: n is a, c, g, t, or inosine
<220> FEATURE:
<221> NAME/KEY: misc_feature
<222> LOCATION: (24)..(24)
<223> OTHER INFORMATION: n is a, c, g, t, or inosine

<400> SEQUENCE: 23
gancgnaann gngcngcngn ngangt                                    26

<210> SEQ ID NO 24
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, t, or inosine
<220> FEATURE:
<221> NAME/KEY: misc_feature
<222> LOCATION: (6)..(6)
<223> OTHER INFORMATION: n is a, c, g, t, or inosine
<220> FEATURE:
<221> NAME/KEY: misc_feature
<222> LOCATION: (9)..(9)
<223> OTHER INFORMATION: n is a, c, g, t, or inosine
<220> FEATURE:
<221> NAME/KEY: misc_feature
<222> LOCATION: (12)..(12)
<223> OTHER INFORMATION: n is a, c, g, t, or inosine
<220> FEATURE:
<221> NAME/KEY: misc_feature
<222> LOCATION: (15)..(15)
<223> OTHER INFORMATION: n is a, c, g, t, or inosine
<220> FEATURE:
<221> NAME/KEY: misc_feature
<222> LOCATION: (18)..(18)
<223> OTHER INFORMATION: n is a, c, g, t, or inosine

<400> SEQUENCE: 24
tcnaantang tnatnaantc                                           20

<210> SEQ ID NO 25
<211> LENGTH: 21
<212> TYPE: DNA
<213> ORGANISM: Artificial sequence
```

```
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 25
gtcgttnact tcngcgtgaa t                                              21

<210> SEQ ID NO 26
<211> LENGTH: 20
<212> TYPE: DNA
<213> ORGANISM: Artificial sequence
<220> FEATURE:
<223> OTHER INFORMATION: Synthetic primer

<400> SEQUENCE: 26
cgcgaaggta gtcagcatct                                                20

<210> SEQ ID NO 27
<211> LENGTH: 2784
<212> TYPE: DNA
<213> ORGANISM: Dechloromonas agitata

<400> SEQUENCE: 27
atggcacgac tgagtcgcag agattttttg aaggcatccg ccgccactct gctgggtaat    60
tcacttacct tcaaaacatt agcggccacc atggatttat ccggcgcctt cgaatattcg   120
ggctgggaaa attttcatcg caaccagtgg tcgtgggaca gaaaactcg cggagcgcac    180 ctgatcaact gtactggggc ttgcccgcac ttcgtttata cgaaagatgg tgtggtcatt   240
cgcgaggagc agtccaagga cattccgccg atgccgaata tcccggaatt gaatccccgg   300
gggtgcaaca aggggagtg cgcacaccac tacatgtatg gtccgcatcg cctgaaatat    360
cctttgatcc gggttggcga acgcgggag ggcaagtggc ggcgtgccac gtgggaggag    420
gcactagacc ttatctcaga caagataatc gacacgatca agaatcactc tcccgattgc   480
atcagtgtct actcacctct tccgggcaca gcaccagtat cgttctctgc tggacacagg   540
tttgcgcact atatcggcgc ccatacacat accttctttg actggtacag tgaccatccc   600
actggtcaga cacagacgtg cggtgtccag ggcgactcag cggagtgctc cgactggttc   660
aactcaaaat acataatcct ctgggggca aaccccactc agactcgtat tccagatgcg   720
catttcctgt cagaggcgca gttgaacggc gcgaaggtag tcagcatctc cccggatttc   780
aactcttcta ccatcaaggc ggaccgttgg attcaccctc tgcccggtac tgatggcgcc   840
ctcgcactgg ccatggcgca tgtgatcatc aaggaaaagc tctacgacgc ccacaacctc   900
aaggaacaaa ctgatctacc gtatttgatc agaagggaca ccaagcggtt cttacgtgaa   960
gctgatgtgg ttgccggggg atccaaagat aagttctata tttgggacag caagactggc  1020
aagccggtaa tcacgaaagg ttcctggggc gaccaaccag aacaaaaagc tccgcctgtc  1080
gcatttatgg gaaggaacac ccatacattc ccaagggct atatcgccct ggagaatctg   1140
gaccccgccc tggaaggcaa atttcaggtc aagttgcagg atggaaatac agttgaagtc  1200
agaccagtat tcgaaattct gaatcgcgc atcgaggccg acaacaatat cgccaaggca   1260
gcgaaaatca ccggggtgcc ggcaaagacc atcattgaag tggccagaga gtatgcaaca  1320
```

```
acgcagccgg cgatgatcat ttgcggtggc ggcactatgc actggtatta cagcgacgtg    1380
ctgttacgtg cgatgcatct gctaaccgca ctcgttggca gcgaaggcaa gaatggcggc    1440
gggatgaatc attacatcgg acagtggaag cctgtcttcc tgccgggtgt ggctgctctc    1500
gccttccccg aaggccctgc gaacgaacgg tcctgccaga cgacgatctg gacttacatc    1560
catgccgaag ttaacgacga gatggcaaat gtcgggatcg ataccgacaa gtatctgatg    1620
cacgcgatcg atacgcgcca aatgccgaat taccctcgag acggcagaga tcccaaagta    1680
tttatcgtct atcgcggcaa ctggctaaac caagccaagg gacagaaata tgtcttgcgc    1740
aatctctggc ccaagctgga tttgattgtt gacatcaata tccgcatgga ctcaacggcg    1800
ctgtattcgg atgttgtgct gccttccgct cactggtacg aaaagctcga cctcaacgtc    1860
accgccgagc acacctatat caacatgacg gaaccggcaa tcaagccgat gtgggaatcc    1920
aagaccgatt ggcagatttt cctcgcactc gccaaacgcg ttgaaatgtc agccaagcgc    1980
aagagttttg agaggtttta cgacgaacaa ttcaagtggg cacgcgacct gacgaacctg    2040
tggaaccaga tgaccatgga cggcaagttg gccgaggatg aggctgctgc ccaatacatt    2100
ctggacactg cccccattc gaaaggcatt acgctccaga tgctgaggga aaaaggtgag    2160
cgcttcaagg cgaattggac ttcgccgatg aaggaaggcg tgccctatac cccgttccag    2220
aattacattg tcgacaagaa gccttggccg acactcacgg ggcgccagca gttctatctg    2280
gaccatgaag tgttcttcga atgggtgtc gaattgccga cctacaaggc tccggtcgat    2340
gcggacaaat tccccttccg cttcaactcg ccacacagtc gtcattcgat ccactcgacc    2400
ttcaaggata gtgtgctgat gctacggctt cagcgcggcg gtccctgcgt agaaatctcg    2460
ccgatcgatg ccacggcaat tggagtcaag acaacgact gggtagaaat ctggaatagc    2520
cacggcaagg tgatctgccg ggccaagatc cgtgccggtg agcaacgtgg ccgcgtctcc    2580
atgtggcaca ccccggaact gtacatggat ctcctcgaag gcagcacgca aagcgtatgc    2640
cccgtccgca tcacgccaac gcacttggtg ggcaactacg acatttggt gtttcgcccg    2700
aactactacg accggccgg cagccagcga gacgttcgtg tcgatgtgaa acgctatatc    2760
ggcgcaactc cgatcagtct ctag                                          2784
```

<210> SEQ ID NO 28
<211> LENGTH: 927
<212> TYPE: PRT
<213> ORGANISM: Dechloromonas agitata

<400> SEQUENCE: 28

```
Met Ala Arg Leu Ser Arg Arg Asp Phe Leu Lys Ala Ser Ala Ala Thr
1               5                   10                  15

Leu Leu Gly Asn Ser Leu Thr Phe Lys Thr Leu Ala Ala Thr Met Asp
            20                  25                  30

Leu Ser Gly Ala Phe Glu Tyr Ser Gly Trp Glu Asn Phe His Arg Asn
        35                  40                  45

Gln Trp Ser Trp Asp Lys Lys Thr Arg Gly Ala His Leu Ile Asn Cys
    50                  55                  60

Thr Gly Ala Cys Pro His Phe Val Tyr Thr Lys Asp Gly Val Val Ile
65                  70                  75                  80

Arg Glu Glu Gln Ser Lys Asp Ile Pro Pro Met Pro Asn Ile Pro Glu
                85                  90                  95

Leu Asn Pro Arg Gly Cys Asn Lys Gly Glu Cys Ala His His Tyr Met
            100                 105                 110
```

```
Tyr Gly Pro His Arg Leu Lys Tyr Pro Leu Ile Arg Val Gly Glu Arg
        115                 120                 125

Gly Glu Gly Lys Trp Arg Arg Ala Thr Trp Glu Glu Ala Leu Asp Leu
    130                 135                 140

Ile Ser Asp Lys Ile Ile Asp Thr Ile Lys Asn His Ser Pro Asp Cys
145                 150                 155                 160

Ile Ser Val Tyr Ser Pro Leu Pro Gly Thr Ala Pro Val Ser Phe Ser
                165                 170                 175

Ala Gly His Arg Phe Ala His Tyr Ile Gly Ala His Thr His Thr Phe
            180                 185                 190

Phe Asp Trp Tyr Ser Asp His Pro Thr Gly Gln Thr Gln Thr Cys Gly
        195                 200                 205

Val Gln Gly Asp Ser Ala Glu Cys Ser Asp Trp Phe Asn Ser Lys Tyr
    210                 215                 220

Ile Ile Leu Trp Gly Ala Asn Pro Thr Gln Thr Arg Ile Pro Asp Ala
225                 230                 235                 240

His Phe Leu Ser Glu Ala Gln Leu Asn Gly Ala Lys Val Val Ser Ile
                245                 250                 255

Ser Pro Asp Phe Asn Ser Ser Thr Ile Lys Ala Asp Arg Trp Ile His
            260                 265                 270

Pro Leu Pro Gly Thr Asp Gly Ala Leu Ala Leu Ala Met Ala His Val
        275                 280                 285

Ile Ile Lys Glu Lys Leu Tyr Asp Ala His Asn Leu Lys Glu Gln Thr
    290                 295                 300

Asp Leu Pro Tyr Leu Ile Arg Arg Asp Thr Lys Arg Phe Leu Arg Glu
305                 310                 315                 320

Ala Asp Val Val Ala Gly Gly Ser Lys Asp Lys Phe Tyr Ile Trp Asp
                325                 330                 335

Ser Lys Thr Gly Lys Pro Val Ile Thr Lys Gly Ser Trp Gly Asp Gln
            340                 345                 350

Pro Glu Gln Lys Ala Pro Pro Val Ala Phe Met Gly Arg Asn Thr His
        355                 360                 365

Thr Phe Pro Lys Gly Tyr Ile Ala Leu Glu Asn Leu Asp Pro Ala Leu
    370                 375                 380

Glu Gly Lys Phe Gln Val Lys Leu Gln Asp Gly Asn Thr Val Glu Val
385                 390                 395                 400

Arg Pro Val Phe Glu Ile Leu Lys Ser Arg Ile Glu Ala Asp Asn Asn
                405                 410                 415

Ile Ala Lys Ala Ala Lys Ile Thr Gly Val Pro Ala Lys Thr Ile Ile
            420                 425                 430

Glu Val Ala Arg Glu Tyr Ala Thr Gln Pro Ala Met Ile Ile Cys
        435                 440                 445

Gly Gly Gly Thr Met His Trp Tyr Tyr Ser Asp Val Leu Leu Arg Ala
    450                 455                 460

Met His Leu Leu Thr Ala Leu Val Gly Ser Glu Gly Lys Asn Gly Gly
465                 470                 475                 480

Gly Met Asn His Tyr Ile Gly Gln Trp Lys Pro Val Phe Leu Pro Gly
                485                 490                 495

Val Ala Ala Leu Ala Phe Pro Glu Gly Pro Ala Asn Glu Arg Ser Cys
            500                 505                 510

Gln Thr Thr Ile Trp Thr Tyr Ile His Ala Glu Val Asn Asp Glu Met
        515                 520                 525
```

-continued

```
Ala Asn Val Gly Ile Asp Thr Asp Lys Tyr Leu Met His Ala Ile Asp
        530                 535                 540

Thr Arg Gln Met Pro Asn Tyr Pro Arg Asp Gly Arg Asp Pro Lys Val
545                 550                 555                 560

Phe Ile Val Tyr Arg Gly Asn Trp Leu Asn Gln Ala Lys Gly Gln Lys
                565                 570                 575

Tyr Val Leu Arg Asn Leu Trp Pro Lys Leu Asp Leu Ile Val Asp Ile
            580                 585                 590

Asn Ile Arg Met Asp Ser Thr Ala Leu Tyr Ser Asp Val Val Leu Pro
        595                 600                 605

Ser Ala His Trp Tyr Glu Lys Leu Asp Leu Asn Val Thr Ala Glu His
        610                 615                 620

Thr Tyr Ile Asn Met Thr Glu Pro Ala Ile Lys Pro Met Trp Glu Ser
625                 630                 635                 640

Lys Thr Asp Trp Gln Ile Phe Leu Ala Leu Ala Lys Arg Val Glu Met
                645                 650                 655

Ser Ala Lys Arg Lys Ser Phe Glu Arg Phe Tyr Asp Glu Gln Phe Lys
            660                 665                 670

Trp Ala Arg Asp Leu Thr Asn Leu Trp Asn Gln Met Thr Met Asp Gly
        675                 680                 685

Lys Leu Ala Glu Asp Glu Ala Ala Gln Tyr Ile Leu Asp Thr Ala
        690                 695                 700

Pro His Ser Lys Gly Ile Thr Leu Gln Met Leu Arg Glu Lys Gly Glu
705                 710                 715                 720

Arg Phe Lys Ala Asn Trp Thr Ser Pro Met Lys Glu Gly Val Pro Tyr
                725                 730                 735

Thr Pro Phe Gln Asn Tyr Ile Val Asp Lys Lys Pro Trp Pro Thr Leu
            740                 745                 750

Thr Gly Arg Gln Gln Phe Tyr Leu Asp His Glu Val Phe Phe Glu Met
        755                 760                 765

Gly Val Glu Leu Pro Thr Tyr Lys Ala Pro Val Asp Ala Asp Lys Phe
        770                 775                 780

Pro Phe Arg Phe Asn Ser Pro His Ser Arg His Ser Ile His Ser Thr
785                 790                 795                 800

Phe Lys Asp Ser Val Leu Met Leu Arg Leu Gln Arg Gly Gly Pro Cys
                805                 810                 815

Val Glu Ile Ser Pro Ile Asp Ala Thr Ala Ile Gly Val Lys Asp Asn
            820                 825                 830

Asp Trp Val Glu Ile Trp Asn Ser His Gly Lys Val Ile Cys Arg Ala
        835                 840                 845

Lys Ile Arg Ala Gly Glu Gln Arg Gly Arg Val Ser Met Trp His Thr
        850                 855                 860

Pro Glu Leu Tyr Met Asp Leu Leu Glu Gly Ser Thr Gln Ser Val Cys
865                 870                 875                 880

Pro Val Arg Ile Thr Pro Thr His Leu Val Gly Asn Tyr Gly His Leu
                885                 890                 895

Val Phe Arg Pro Asn Tyr Tyr Gly Pro Ala Gly Ser Gln Arg Asp Val
            900                 905                 910

Arg Val Asp Val Lys Arg Tyr Ile Gly Ala Thr Pro Ile Ser Leu
        915                 920                 925
```

<210> SEQ ID NO 29
<211> LENGTH: 1002
<212> TYPE: DNA
<213> ORGANISM: Dechloromonas agitata

<400> SEQUENCE: 29

```
atgtcaaata tgacgaagtc gcctaaacgc caattggcat atgttgccga cctgaataag      60
tgcattggct gccagacatg cactgtcgca tgcaagactc tttggactag tggacctgga     120
caggactaca tgtattggcg gaatgtcgaa accgccccag gtttggggta ccaagaaac      180
tggcagagca agggcggtgg atacaaggat ggagtcctgc agaaagggaa gattccgccg     240
atgatcgatt atgcgttcc cttcgaattc gactacgccg gtcggctttt cgaagggaaa      300
aaggaaagag cgcgaccgag tccgacgcct cggtatgctc ccaattggga tgaggatcag     360
ggagcgggcg aatatcccaa caactccttt ttctatgtgc cgcggatgtg caaccactgc     420
gccaagccgg catgtcttga agcctgcccg aatgaagcga tatacaagcg cgagcaagac     480
ggcctggtgg tgatccatca ggagaagtgc aaagggctc aggcatgtat ccagtcctgc     540
ccatatgcca aaccatactt taatgctcag gtcaataaag ccaacaagtg catcggttgc     600
ttcccgcgga ttgaaaaagg ggttgcaccg gcatgcgttg ctgagtgtgc gggaagagcc     660
atgcatgtcg gcttcatcga tgaccaagaa agctccgtgt tcaagctggt caagcggttc     720
ggcgtggcac tgcctttgca ccccgagtac ggcaccgaac ccaacgtgtt ctatgtccct     780
cccgttctcg accgcgcgt agaaatgccg aatggcgaac ataccgccga cccgaaaatt     840
tcgatgactc agcttgaaca gttgtttggc aagcaggtcc gcgaggtttt gaagacgctg     900
caggccgaac gcgagaaaaa gatcaagaac cagccgtctg aactgatgga catcctgatc     960
ggccgacgca gtgcggacat gatgatttcg cctatgacct ga                       1002
```

<210> SEQ ID NO 30
<211> LENGTH: 333
<212> TYPE: PRT
<213> ORGANISM: Dechloromonas agitata

<400> SEQUENCE: 30

Met Ser Asn Met Thr Lys Ser Pro Lys Arg Gln Leu Ala Tyr Val Ala
1               5                   10                  15

Asp Leu Asn Lys Cys Ile Gly Cys Gln Thr Cys Thr Val Ala Cys Lys
            20                  25                  30

Thr Leu Trp Thr Ser Gly Pro Gly Gln Asp Tyr Met Tyr Trp Arg Asn
        35                  40                  45

Val Glu Thr Ala Pro Gly Leu Gly Tyr Pro Arg Asn Trp Gln Ser Lys
    50                  55                  60

Gly Gly Gly Tyr Lys Asp Gly Val Leu Gln Lys Gly Lys Ile Pro Pro
65                  70                  75                  80

Met Ile Asp Tyr Gly Val Pro Phe Glu Phe Asp Tyr Ala Gly Arg Leu
                85                  90                  95

Phe Glu Gly Lys Lys Glu Arg Ala Arg Pro Ser Pro Thr Pro Arg Tyr
            100                 105                 110

Ala Pro Asn Trp Asp Glu Asp Gln Gly Ala Gly Glu Tyr Pro Asn Asn
        115                 120                 125

Ser Phe Phe Tyr Val Pro Arg Met Cys Asn His Cys Ala Lys Pro Ala
    130                 135                 140

Cys Leu Glu Ala Cys Pro Asn Glu Ala Ile Tyr Lys Arg Glu Gln Asp
145                 150                 155                 160

```
Gly Leu Val Val Ile His Gln Glu Lys Cys Lys Gly Ala Gln Ala Cys
                165                 170                 175

Ile Gln Ser Cys Pro Tyr Ala Lys Pro Tyr Phe Asn Ala Gln Val Asn
            180                 185                 190

Lys Ala Asn Lys Cys Ile Gly Cys Phe Pro Arg Ile Glu Lys Gly Val
        195                 200                 205

Ala Pro Ala Cys Val Ala Glu Cys Ala Gly Arg Ala Met His Val Gly
    210                 215                 220

Phe Ile Asp Asp Gln Glu Ser Ser Val Phe Lys Leu Val Lys Arg Phe
225                 230                 235                 240

Gly Val Ala Leu Pro Leu His Pro Glu Tyr Gly Thr Glu Pro Asn Val
                245                 250                 255

Phe Tyr Val Pro Pro Val Leu Gly Pro Arg Val Glu Met Pro Asn Gly
            260                 265                 270

Glu His Thr Ala Asp Pro Lys Ile Ser Met Thr Gln Leu Glu Gln Leu
        275                 280                 285

Phe Gly Lys Gln Val Arg Glu Val Leu Lys Thr Leu Gln Ala Glu Arg
    290                 295                 300

Glu Lys Lys Ile Lys Asn Gln Pro Ser Glu Leu Met Asp Ile Leu Ile
305                 310                 315                 320

Gly Arg Arg Ser Ala Asp Met Met Ile Ser Pro Met Thr
                325                 330
```

<210> SEQ ID NO 31
<211> LENGTH: 163
<212> TYPE: DNA
<213> ORGANISM: Dechloromonas agitata

<400> SEQUENCE: 31

```
atgaaaagaa tcgttgctct gttaagcacg ttgctcgtta ccgcgatgcc gagcatgggc      60
gtagcccaac agaccgaata tttaggcttt cgcgcatgca caaagtgtca cgatgcccag     120
ggtgatacct ggcggacatc ggcacatgcc aaagcctttg agt                       163
```

<210> SEQ ID NO 32
<211> LENGTH: 54
<212> TYPE: PRT
<213> ORGANISM: Dechloromonas agitata

<400> SEQUENCE: 32

```
Met Lys Arg Ile Val Ala Leu Leu Ser Thr Leu Leu Val Thr Ala Met
1               5                   10                  15

Pro Ser Met Gly Val Ala Gln Gln Thr Glu Tyr Leu Gly Phe Arg Ala
            20                  25                  30

Cys Thr Lys Cys His Asp Ala Gln Gly Asp Thr Trp Arg Thr Ser Ala
        35                  40                  45

His Ala Lys Ala Phe Glu
    50
```

<210> SEQ ID NO 33
<211> LENGTH: 675
<212> TYPE: DNA
<213> ORGANISM: Dechloromonas agitata

<400> SEQUENCE: 33

```
atgaatagta ttaccgacga tcgactcgtc ttggcggccg ataaagcgtt atgccgaagc      60
cacatttatt cattgttggc cagtggattt ggatatcccg acgaatctgg ttatcaggga     120
```

-continued

```
ttttcggacg gcaagtttat tgatgaaatc cgtcaggaac tcggggtatg ttggggtgaa      180
ctcttggagc atttaatga ggtacttgct cctgggttga aacttgcctg ctcgcgcgaa       240
gtattcgaat cacagttctt gagtgcattc gagaccaata tgccatcacc tagcgcctcc     300
ttgaatgaag gtgttcacat atttaaatcg gaccgaccaa atttattgct cgaactgaag     360
ggtttttaca gcaacttcgg cttgcaggtc gatagcaaag gcaatgagct gaagacact      420 ctgacagcag aacttgattt catgcagttt cttgcgttga acaggcaca ggcccatctc      480 gaaggcatgt cggctgatgc ctacaagttg gcgcagaagg attttctgga gcggcaccta    540
tgtgcttggt tgccattggt gcggagggaa atcgccgaaa aggtgactac cccattcttc    600
gtcactcttg ctgagtttgc agaaagcttt gcgcttgcta atttaagaga attgaaagaa    660
gagctaggag aataa                                                      675
```

<210> SEQ ID NO 34
<211> LENGTH: 224
<212> TYPE: PRT
<213> ORGANISM: Dechloromonas agitata

<400> SEQUENCE: 34

Met Asn Ser Ile Thr Asp Asp Arg Leu Val Leu Ala Ala Asp Lys Ala
1               5                   10                  15

Leu Cys Arg Ser His Ile Tyr Ser Leu Leu Ala Ser Gly Phe Gly Tyr
                20                  25                  30

Pro Asp Glu Ser Gly Tyr Gln Gly Phe Ser Asp Gly Lys Phe Ile Asp
            35                  40                  45

Glu Ile Arg Gln Glu Leu Gly Val Cys Trp Gly Leu Leu Glu His
        50                  55                  60

Phe Asn Glu Val Leu Ala Pro Gly Leu Lys Leu Ala Cys Ser Arg Glu
65                  70                  75                  80

Val Phe Glu Ser Gln Phe Leu Ser Ala Phe Glu Thr Asn Met Pro Ser
                85                  90                  95

Pro Ser Ala Ser Leu Asn Glu Gly Val His Ile Phe Lys Ser Asp Arg
            100                 105                 110

Pro Asn Leu Leu Leu Glu Leu Lys Gly Phe Tyr Ser Asn Phe Gly Leu
        115                 120                 125

Gln Val Asp Ser Lys Gly Asn Glu Leu Glu Asp Thr Leu Thr Ala Glu
    130                 135                 140

Leu Asp Phe Met Gln Phe Leu Ala Leu Lys Gln Ala Gln Ala His Leu
145                 150                 155                 160

Glu Gly Met Ser Ala Asp Ala Tyr Lys Leu Ala Gln Lys Asp Phe Leu
                165                 170                 175

Glu Arg His Leu Cys Ala Trp Leu Pro Leu Val Arg Arg Glu Ile Ala
            180                 185                 190

Glu Lys Val Thr Thr Pro Phe Phe Val Thr Leu Ala Glu Phe Ala Glu
        195                 200                 205

Ser Phe Ala Leu Ala Asn Leu Arg Glu Leu Lys Glu Glu Leu Gly Glu
    210                 215                 220

<210> SEQ ID NO 35
<211> LENGTH: 327
<212> TYPE: PRT
<213> ORGANISM: Thauera selenatis

<400> SEQUENCE: 35

```
Met Ser Gln Arg Gln Leu Ala Tyr Val Phe Asp Leu Asn Lys Cys Ile
1               5                   10                  15

Gly Cys His Thr Cys Thr Met Ala Cys Lys Gln Leu Trp Thr Asn Arg
            20                  25                  30

Asp Gly Arg Glu Tyr Met Tyr Trp Asn Asn Val Glu Ser Arg Pro Gly
        35                  40                  45

Lys Gly Tyr Pro Lys Asn Trp Glu Gln Lys Gly Gly Phe Asp Lys
    50                  55                  60

Asp Gly Lys Leu Lys Thr Asn Gly Ile Ile Pro Ile Arg Ala Asp Tyr
65                  70                  75                  80

Gly Gly Thr Trp Asn Tyr Asn Leu Leu Glu Thr Leu Val Glu Gly Lys
                85                  90                  95

Ser Asn Gln Val Val Pro Asp Glu Lys Pro Thr Trp Gly Pro Asn Trp
            100                 105                 110

Asp Glu Asp Glu Gly Lys Gly Glu Phe Pro Asn Asn His Tyr Phe Tyr
        115                 120                 125

Leu Pro Arg Ile Cys Asn His Cys Ser Asn Pro Ala Cys Leu Ala Ala
130                 135                 140

Cys Pro Thr Lys Ala Ile Tyr Lys Arg Glu Glu Asp Gly Leu Val Val
145                 150                 155                 160

Val Asp Gln Ser Arg Cys Lys Gly Tyr Arg Tyr Cys Val Lys Ala Cys
                165                 170                 175

Pro Tyr Gly Lys Met Tyr Phe Asn Leu Gln Lys Gly Thr Ser Glu Lys
            180                 185                 190

Cys Ile Gly Cys Tyr Pro Arg Val Glu Lys Gly Glu Ala Pro Ala Cys
        195                 200                 205

Val Lys Gln Cys Ser Gly Arg Ile Arg Phe Trp Gly Tyr Arg Asp Asp
    210                 215                 220

Lys Asp Gly Pro Ile Tyr Lys Leu Val Asp Gln Trp Lys Val Ala Leu
225                 230                 235                 240

Pro Leu His Ala Glu Tyr Gly Thr Glu Pro Asn Val Phe Tyr Val Pro
                245                 250                 255

Pro Met Asn Thr Thr Pro Pro Phe Glu Glu Asp Gly Arg Leu Gly
            260                 265                 270

Asp Lys Pro Arg Ile Pro Ile Glu Asp Leu Glu Ala Leu Phe Gly Pro
        275                 280                 285

Gly Val Lys Gln Ala Leu Ala Thr Leu Gly Gly Glu Met Ala Lys Arg
    290                 295                 300

Arg Lys Ala Gln Ala Ser Glu Leu Thr Asp Ile Leu Ile Gly Tyr Thr
305                 310                 315                 320

Asn Lys Asp Arg Tyr Gly Ile
                325
```

<210> SEQ ID NO 36
<211> LENGTH: 328
<212> TYPE: PRT
<213> ORGANISM: Ideonella dechloratans

<400> SEQUENCE: 36

```
Met Ser Gln Arg Gln Val Ala Tyr Val Phe Asp Leu Asn Lys Cys Ile
1               5                   10                  15

Gly Cys His Thr Cys Thr Met Ala Cys Lys Gln Leu Trp Thr Asn Arg
            20                  25                  30
```

```
Asp Gly Arg Glu Tyr Met Tyr Trp Asn Asn Val Glu Thr Arg Pro Gly
            35                  40                  45

Lys Gly Tyr Pro Lys Asn Trp Glu Gly Lys Gly Gly Phe Asp Gln
 50                  55                  60

Glu Gly Lys Leu Lys Thr Asn Gly Ile Ile Pro Ile Met Ala Asp Tyr
 65                  70                  75                  80

Gly Gly Arg Ile Gly Asp Phe Asn Leu Asn Glu Val Leu Leu Glu Gly
                 85                  90                  95

Lys Ala Asp Gln Val Val Pro His Glu Lys Ala Thr Trp Gly Pro Asn
            100                 105                 110

Trp Asp Glu Asp Glu Gly Lys Gly Glu Phe Pro Asn Asn His Ser Phe
            115                 120                 125

Tyr Leu Pro Arg Ile Cys Asn His Cys Ser Asn Pro Ala Cys Leu Ala
130                 135                 140

Ala Cys Pro Thr Lys Ala Ile Tyr Lys Arg Pro Glu Asp Gly Ile Val
145                 150                 155                 160

Val Val Asp Gln Thr Arg Cys Arg Gly Tyr Arg Tyr Cys Val Lys Ala
                165                 170                 175

Cys Pro Tyr Gly Lys Met Tyr Phe Asn Leu Gln Lys Gly Lys Ser Glu
            180                 185                 190

Lys Cys Ile Gly Cys Tyr Pro Arg Val Glu Lys Gly Glu Ala Pro Ala
            195                 200                 205

Cys Val Lys Gln Cys Ser Gly Arg Ile Arg Phe Trp Gly Tyr Arg Asp
210                 215                 220

Asp Lys Asn Gly Pro Ile Tyr Lys Leu Val Glu Gln Trp Lys Val Ala
225                 230                 235                 240

Leu Pro Leu His Ala Glu Tyr Gly Thr Glu Pro Asn Val Phe Tyr Val
                245                 250                 255

Pro Pro Met Asn Thr Thr Pro Pro Phe Glu Glu Asp Gly Arg Leu
            260                 265                 270

Gly Asp Lys Pro Arg Ile Pro Ile Glu Asp Leu Glu Ala Leu Phe Gly
            275                 280                 285

Pro Gly Val Lys Gln Ala Leu Ala Thr Leu Gly Gly Glu Met Ala Lys
            290                 295                 300

Arg Arg Lys Ala Gln Ala Ser Glu Leu Thr Asp Ile Leu Ile Gly Phe
305                 310                 315                 320

Thr Asn Lys Asp Arg Tyr Gly Val
                325

<210> SEQ ID NO 37
<211> LENGTH: 352
<212> TYPE: PRT
<213> ORGANISM: Azoarcus sp.

<400> SEQUENCE: 37

Met Thr Tyr Val Gln Asp Gly Asn Lys Ser Glu Leu Arg Lys Ala Lys
1               5                   10                  15

Arg Gln Leu Val Thr Val Ile Asp Leu Asn Lys Cys Leu Gly Cys Gln
                20                  25                  30

Thr Cys Thr Val Ala Cys Lys Asn Ile Trp Thr Lys Arg Pro Gly Thr
            35                  40                  45

Glu His Met Arg Trp Asn Asn Val Thr Thr Tyr Pro Gly Lys Gly Tyr
 50                  55                  60

Pro Arg Asp Tyr Glu Arg Lys Gly Gly Phe Leu Arg Gly Glu Pro
 65                  70                  75                  80
```

```
Gln Pro Gly Val Leu Pro Thr Leu Ile Asp Ser Gly Asp Phe Gln
                85                  90                  95

Phe Asn His Lys Glu Val Phe Tyr Glu Gly Lys Gly Gln Thr Val His
            100                 105                 110

Phe His Pro Thr Ser Lys Ser Thr Gly Lys Asp Pro Ala Trp Gly Tyr
        115                 120                 125

Asn Trp Asp Glu Asp Gln Gly Gly Lys Trp Pro Asn Pro Phe Phe
130                 135                 140

Phe Tyr Leu Ala Arg Met Cys Asn His Cys Thr Asn Pro Ala Cys Leu
145                 150                 155                 160

Ala Ala Cys Pro Thr Gly Ala Ile Tyr Lys Arg Glu Asp Asn Gly Ile
                165                 170                 175

Val Leu Val Asp Gln Glu Arg Cys Lys Gly His Arg His Cys Val Glu
            180                 185                 190

Ala Cys Pro Tyr Lys Ala Ile Tyr Phe Asn Pro Val Ser Gln Thr Ser
        195                 200                 205

Glu Lys Cys Ile Leu Cys Tyr Pro Arg Ile Glu Lys Gly Ile Ala Asn
    210                 215                 220

Ala Cys Asn Arg Gln Cys Pro Gly Arg Val Arg Ala Phe Gly Tyr Leu
225                 230                 235                 240

Asp Asp Thr Thr Ser His Val His Lys Leu Val Lys Lys Trp Lys Val
                245                 250                 255

Ala Leu Pro Leu His Ala Glu Tyr Gly Thr Gly Pro Asn Ile Tyr Tyr
            260                 265                 270

Val Pro Pro Met Gly Ala Arg Gly Phe Gly Glu Asp Gly Glu Ile Thr
        275                 280                 285

Asp Lys Thr Arg Ile Pro Leu Asp Val Leu Glu Gly Leu Phe Gly Pro
    290                 295                 300

Glu Val Lys Arg Val Leu Ala Val Leu His Thr Glu Arg Glu Asn Met
305                 310                 315                 320

Arg Ala Gly Arg Gly Ser Glu Leu Met Asp Leu Leu Ile Ser Lys Lys
                325                 330                 335

Trp Ser Asp Arg Phe Gly Gly Phe Thr Asn Asp Pro Leu Thr Gln Ser
            340                 345                 350

<210> SEQ ID NO 38
<211> LENGTH: 325
<212> TYPE: PRT
<213> ORGANISM: Rhodopseudomonas sulfidophilum

<400> SEQUENCE: 38

Met Val Lys Arg Gln Ile Ser Met Val Leu Asp Leu Asn Lys Cys Ile
1               5                   10                  15

Gly Cys Gln Thr Cys Thr Ser Ala Cys Lys Leu Gln Trp Thr Asn Arg
                20                  25                  30

Asn Gly Arg Glu Tyr Met Tyr Trp Asn Asn Val Glu Thr His Pro Gly
            35                  40                  45

Pro Gly Tyr Pro Arg Asn Tyr Glu His Ser Gly Gly Phe Asp Glu
        50                  55                  60

Glu Gly Ala Leu Lys Ile Gly Ile Thr Pro Ser Ala Glu Asp Tyr Gly
65                  70                  75                  80

Ile Pro Trp Glu Tyr Asn Tyr Glu Glu Ala Leu Met Thr Gly Thr Asp
                85                  90                  95

Pro Trp Leu Arg Pro Asn Val Lys Pro Thr Trp Gly Ala Asn Trp Asn
            100                 105                 110
```

Glu Asp Glu Gly Arg Gly Glu Tyr Pro Asn Ser Tyr Tyr Phe Tyr Leu
            115                 120                 125

Pro Arg Ile Cys Asn His Cys Ala Asn Pro Gly Cys Leu Ala Ala Cys
        130                 135                 140

Ala Arg Asn Ala Ile Tyr Lys Arg Gln Glu Asp Gly Ile Val Leu Val
145                 150                 155                 160

Asp Gln Glu Arg Cys Arg Gly Tyr Arg Tyr Cys Ile Thr Ala Cys Pro
                165                 170                 175

Tyr Lys Lys Val Tyr Phe Asn Glu Gln Ile Ser Lys Ala Glu Lys Cys
            180                 185                 190

Ile Phe Cys Tyr Pro Arg Ile Glu Lys Gly Leu Pro Thr Ala Cys Ala
        195                 200                 205

Lys Gln Cys Val Gly Arg Ile Arg Phe Ile Gly Tyr Leu Asp Asp Glu
210                 215                 220

Ala Gly Pro Val His Leu Leu Val Glu Arg Tyr Lys Val Ala Ile Pro
225                 230                 235                 240

Leu His Pro Glu Trp Gly Thr Lys Pro Ser Val Phe Tyr Val Pro Pro
                245                 250                 255

Leu Ala Pro Pro Arg Ile Gly Asp Asp Gly Glu Pro Thr Glu Glu Thr
            260                 265                 270

Arg Val Pro Leu Ala Tyr Leu Lys Glu Leu Phe Gly Glu Ala Val Val
        275                 280                 285

Pro Ala Leu Glu Thr Leu Lys Thr Glu Arg Ala Lys Lys Gln Ser Gly
290                 295                 300

Ala Glu Ser Glu Leu Met Asp Thr Leu Ile Gly Tyr Arg His Pro Glu
305                 310                 315                 320

Met Phe Lys Leu Ser
                325

<210> SEQ ID NO 39
<211> LENGTH: 358
<212> TYPE: PRT
<213> ORGANISM: Haloarcula marismortui

<400> SEQUENCE: 39

Met Ser Ser Asp Gln Gln Asp Gln Gly Glu Glu Asp Thr Leu Val
1               5                   10                  15

Asn Val Ala Asp Gly Val Asp His Gln Val Ala Met Val Met Asp Leu
            20                  25                  30

Asn Lys Cys Ile Gly Cys Gln Thr Cys Thr Ile Ala Cys Lys Asn Leu
        35                  40                  45

Trp Thr Glu Asp Gly Gly Ser Glu Tyr Met Tyr Trp Asn Asn Val Glu
    50                  55                  60

Thr Lys Pro Gly Glu Gly Tyr Pro Arg Gly Trp Glu Asn Ser Gly Gly
65                  70                  75                  80

Gly Trp Lys Ser Gly Glu His Lys Glu Arg Gln Pro Gly Glu Ile Pro
                85                  90                  95

Asp Glu Glu Asp Tyr Gly Arg Ala Trp Glu Phe Asn His Glu Glu Ile
            100                 105                 110

Met Tyr Glu Gly Ser Asp Glu Pro Leu Arg Pro Arg Asp Gly Ala Glu
        115                 120                 125

Trp Gly Pro Asn Trp Asp Glu Asp Gln Gly Ala Gly Glu Tyr Pro Asn
130                 135                 140

Ser Tyr Tyr Phe Tyr Leu Pro Arg Ile Cys Asn His Cys Thr His Pro
145                 150                 155                 160

-continued

```
Ser Cys Val Glu Ala Cys Pro Arg Ser Ala Leu Tyr Lys Arg Gln Glu
            165                 170                 175

Asp Gly Ile Val Leu Val Asp Gln Asp Arg Cys Arg Gly Tyr Arg Tyr
        180                 185                 190

Cys Val Glu Gly Cys Pro Tyr Lys Lys Val Tyr Tyr Asn Thr Val Ser
    195                 200                 205

Lys Lys Ser Glu Lys Cys Ile Phe Cys Tyr Pro Arg Ile Glu Gly Glu
    210                 215                 220

Gly Pro Asp Gly Glu Thr Phe Ala Pro Ala Cys Ala Glu Cys Pro
225                 230                 235                 240

Pro Gln Leu Arg Leu Val Gly Phe Leu Asp Asp Glu Gly Pro Ile
            245                 250                 255

His Lys Leu Val Asn Glu Tyr Glu Val Ala Leu Pro Leu His Pro Glu
        260                 265                 270

Phe Arg Thr Gln Pro Asn Val Tyr Tyr Ile Pro Pro Phe Ala Pro Gly
    275                 280                 285

Gln His Thr Glu Asp Gly Glu Thr Val Asp Ile Asp Arg Ile Pro Arg
    290                 295                 300

Gln Tyr Leu Arg Asp Leu Phe Gly Asp Gly Val Asp Gln Ala Leu Asp
305                 310                 315                 320

Thr Ile Glu Arg Glu Arg Gln Arg Ala Arg Gln Gly Glu Asp Ser Glu
            325                 330                 335

Leu Met Glu Leu Leu Gln Asp Lys Asn Pro Ala Lys Gln Tyr Arg Leu
        340                 345                 350

Glu Val Phe Asp Asp Glu
    355

<210> SEQ ID NO 40
<211> LENGTH: 235
<212> TYPE: PRT
<213> ORGANISM: Nitrosomonas europaea

<400> SEQUENCE: 40

Met Lys Ile Met Ile Ala Cys Gly Leu Val Ala Ala Ala Leu Phe Thr
1               5                   10                  15

Leu Thr Ser Gly Gln Ser Leu Ala Ala Asp Ala Pro Phe Glu Gly Arg
            20                  25                  30

Lys Lys Cys Ser Ser Cys His Lys Ala Gln Ala Gln Ser Trp Lys Asp
        35                  40                  45

Thr Ala His Ala Lys Ala Met Glu Ser Leu Lys Pro Asn Val Lys Lys
    50                  55                  60

Glu Ala Lys Gln Lys Ala Lys Leu Asp Pro Ala Lys Asp Tyr Thr Gln
65                  70                  75                  80

Asp Lys Asp Cys Val Gly Cys His Val Asp Gly Phe Gly Gln Lys Gly
                85                  90                  95

Gly Tyr Thr Ile Glu Ser Pro Lys Pro Met Leu Thr Gly Val Gly Cys
            100                 105                 110

Glu Ser Cys His Gly Pro Gly Arg Asn Phe Arg Gly Asp His Arg Lys
        115                 120                 125

Ser Gly Gln Ala Phe Glu Lys Ser Gly Lys Lys Thr Pro Arg Lys Asp
    130                 135                 140

Leu Ala Lys Lys Gly Gln Asp Phe His Phe Glu Glu Arg Cys Ser Ala
145                 150                 155                 160

Cys His Leu Asn Tyr Glu Gly Ser Pro Trp Lys Gly Ala Lys Ala Pro
                165                 170                 175
```

```
Tyr Thr Pro Phe Thr Pro Glu Val Asp Ala Lys Tyr Thr Phe Lys Phe
                180                 185                 190

Asp Glu Met Val Lys Glu Val Lys Ala Met His Glu His Tyr Lys Leu
            195                 200                 205

Glu Gly Val Phe Glu Gly Glu Pro Lys Phe Lys Phe His Asp Glu Phe
        210                 215                 220

Gln Ala Ser Ala Lys Pro Ala Lys Lys Gly Lys
225                 230                 235

<210> SEQ ID NO 41
<211> LENGTH: 1506
<212> TYPE: DNA
<213> ORGANISM: Dechloromonas agitata

<400> SEQUENCE: 41
tgaacgctgg cggcatgcct acacatgca agtcgaacgg cagcacggac ttcggtctgg      60
tggcgagtgg cgaacgggtg agtaatgtat cggaacgtac ctttcagtgg gggataacgt     120
agcgaaagtt acgctaatac cgcatattct gtgagcagga aagcagggga tcgcaagacc     180
ttgcgctgat tgagcggccg atatcagatt agctagttgg tggggtaaag gcctaccaag     240
gctacgatct gtagcgggtc tgagaggatg atccgccaca ctggaactga gacacggtcc     300
agactcctac gggaggcagc agtggggaat tttggacaat gggggcaacc ctgatccagc     360
catgccgcgt gagtgaagaa ggccttcggg ttgtaaagct ctttcggccg ggaagaaatc     420
gcatcagcta atacctggtg tggatgacgg tacccgaata agaagcaccg gctaactacg     480
tgccagcagc cgcggtaata cgtagggtgc gagcgttaat cggaattact gggcgtaaag     540
cgtgcgcagg cggttgtgta agacaggcgt gaaatccccg gctcaacct gggaactgcg     600 cttgtgactg cacagctaga gtacggcaga gggggtgga attccacgtg tagcagtgaa      660
atgcgtagag atgtggagga acaccgatgg cgaaggcagc ccctgggcc gatactgacg      720 ctcatgcacg aaagcgtggg tagcaaacag gattagatac cctggtagtc cacgccctaa     780
acgatgtcaa ctaggtgttg ggtgggtaaa accacctagt accgtagcta acgcgtgaag     840
ttgaccgcct ggggagtacg gccgcaaggt taaaactcaa aggaattgac ggggacccgc     900
acaagcggtg gatgatgtgg attaattcga tgcaacgcga aaaaccttac ctaccttga     960 catgtccaga agcccggaga gatttgggtg tgcccgaaag ggaactggaa cacaggtgct    1020
gcatggctgt cgtcagctcg tgtcgtgaga tgttgggtta agtcccgcaa cgagcgcaac    1080
ccttgtcgtt aattgccatc atttagttgg gcactttaac gagactgccg gtgacaaacc    1140
ggaggaaggt ggggatgacg tcaagtcctc atggccctta tgggtagggc ttcacacgtc    1200
atacaatggt cggtacagag ggttgccaag ccgcgaggtg gagccaatcc cagaaagccg    1260
atcgtagtcc ggattgcagg ctgcaactcg cctgcatgaa gtcggaatcg ctagtaatcg    1320
cggatcagca tgtcgcggtg aatacgttcc cgggtcttgt acacaccgcc cgtcacacca    1380
tgggagcggg ttccgccaga agatggatgc ctaaccgcaa ggagggcgct taccacggcg    1440
gggttcgtga ctggggtgaa gtcgtaacaa ggtagccgta ggggaacctg cggctggatc    1500
acctcc                                                              1506

<210> SEQ ID NO 42
<211> LENGTH: 1460
<212> TYPE: DNA
<213> ORGANISM: Rhynchospora tenuis
```

```
<220> FEATURE:
<221> NAME/KEY: misc_feature
<222> LOCATION: (1045)..(1045)
<223> OTHER INFORMATION: n is a, c, g, or t
<220> FEATURE:
<221> NAME/KEY: misc_feature
<222> LOCATION: (1315)..(1315)
<223> OTHER INFORMATION: n is a, c, g, or t

<400> SEQUENCE: 42
attgaacgct ggcggcatgc cttacacatg caagtcgaac ggcagcacgg gagcaatcct      60
ggtggcgagt ggcgaacggg tgagtaatgc atcggaacgt gccctgaagt gggggataac     120
gtagcgaaag ttacgctaat accgcatatt ctgtgagcag gaaagcaggg gatcgcaaga     180
ccttgcgctt tgggagcggc cgatgtcgga ttagctagtt ggtggggtaa aggcctacca     240
aggccacgat ccgtagcggg tctgagagga tgatccgcca cactgggact gagacacggc     300
ccagactcct acgggaggca gcagtgggga attttggaca atgggcgaaa gcctgatcca     360
gccatgccgc gtgagtgaag aaggccttcg ggttgtaaag ctctttcggc ggggaagaaa     420
ttgctcagga taatacccty agtagatgac ggtacccgaa gaagaagcac cggctaacta     480
cgtgccagca gccgcggtaa tacgtagggt gcgagcgtta atcggaatta ctgggcgtaa     540
agcgtgcgca ggcggttgtg taagacagac gtgaaatccc cgggctcaac ctgggaactg     600
cgtttgtgac tgcacgacta gagtgtgca gaggggggtg gaattccacg tgtagcagtg     660
aaatgcgtag agatgtggag gaacaccgat ggcgaaggca gccccctggg ccaatactga     720
cgctcatgca cgaaagcgtg gggagcaaac aggattagat accctggtag tccacgccct     780
aaacgatgtc aactaggtgt tggtggggtt aaacccatta gtgccgtagc taacgcgtga     840
agttgaccgc ctggggagta cggccgcaag gttaaaactc aaaggaattg acggggaccc     900
gcacaagcgg tggatgatgt ggattaattc gatgcaacgc gaaaaacctt acctacccct     960
gacatgtcag gaatcctgaa gagattcggg agtgcccgaa agggagcctg aacacaggtg    1020
ctgcatggct gtcgtcagct cgtgncgtga gatgttgggt taagtcccgc aacgagcgca    1080
acccttgtca ttaattgcca tcatttagtt gggcactcta atgaaactgc cggtgacaaa    1140
ccggaggaag gtggggatga cgtcaagtcc tcatggccct tatgggtagg cttcacacg     1200 tcatacaatg gtcggtacag agggttgcca agccgcgagg tggagccaat cacagaaagc    1260
cgatcgtagt ccggattgca gtctgcaact cgactgcatg aagtcggaat cgctngtaat    1320
cgcggatcag catgtcgcgg tgaatacgtt cccgggtctt gtacacaccg cccgtcacac    1380
catgggagcg ggttctgcca gaagtagtta gcctaaccgc aaggagggcg attaccacgg    1440
cagcgttcgt gactggggtg                                                1460

<210> SEQ ID NO 43
<211> LENGTH: 1528
<212> TYPE: DNA
<213> ORGANISM: Dechloromonas aromatica

<400> SEQUENCE: 43
gagtttgatc ctggctcaga ttgaacgctg gcggcatgcc ttacacatgc aagtcgaacg      60
gcagcacggg agcaatcctg gtggcgagtg gcgaacgggt gagtaatata tcggaacgta     120
cctttcagtg ggggataacg tagcgaaagt tacgctaata ccgcatattc tgtgagcagg     180
aaagcagggg atcgcaagac cttgcgctga ttgagcggcc gatatcagat tagctagttg     240
gtgaggtaaa ggctcaccaa ggcgacgatc tgtagcgggt ctgagaggat gatccgccac     300
```

```
actggaactg agacacggtc cagactccta cgggaggcag cagtggggaa ttttggacaa      360 tggggggcaac cctgatccag ccatgccgcg tgagtgaaga aggccttcgg gttgtaaagc      420
tctttcagcc gggaagaaaa cgcatgggtt aatacccctgt gtggatgacg gtaccggaat      480
aagaagcacc ggctaactac gtgccagcag ccgcggtaat acgtagggtg cgagcgttaa      540
tcggaattac tgggcgtaaa gcgtgcgcag gcggtttgtt aagataggcg tgaaatcccc      600
gggctcaacc tgggaactgc gtttatgact ggcaggctag agtatggcag agggggggtgg      660 aattccacgt gtagcagtga atgcgtaga gatgtggagg aacaccgatg gcgaaggcag      720 cccctgggc caatactgac gctcatgcac gaaagcgtgg gtagcaaaca ggattagata      780
ccctggtagt ccacgcccta acgatgtca actaggtgtt gggagggtaa aacctttttag      840 taccggagct aacgcgtgaa gttgaccgcc tggggagtac ggccgcaagg ttaaaactca      900
aaggaattga cggggacccg cacaagcggt ggatgatgtg gattaattcg atgcaacgcg      960
aaaaacctta cctaccccttg acatgtccgg aagcccttag agatttgggt gtgctcgaaa     1020
gagagccgga acacaggtgc tgcatggctg tcgtcagctc gtgtcgtgag atgttgggtt     1080
aagtcccgca acgagcgcaa cccttgtcgt taattgccat catttagttg ggcactttaa     1140
cgagactgcc ggtgacaaac cggaggaagg tggggatgac gtcaagtcct catggccctt     1200
atgggtaggg cttcacacgt catacaatgg tcggtacaaa gggttgccaa cccgcgaggg     1260
ggagctaatc ccagaaagcc gatcgtagtc cggatcgtag gctgcaactc gcctgcgtga     1320
agtcggaatc gctagtaatc gtggatcagc atgtcacggt gaatacgttc ccgggtcttg     1380
tacacaccgc ccgtcacaca atgggagcgg ttccgccag aagtaggtag cctaaccgca     1440
aggggggcgc ttaccacggc ggggttcgtg actggggtga agtcgtaaca aggtagccgt     1500
aggggaacct gcggctggat caccctcct                                       1528
```

<210> SEQ ID NO 44
<211> LENGTH: 1525
<212> TYPE: DNA
<213> ORGANISM: Dechloromonas sp.

<400> SEQUENCE: 44

```
tttgatcctg gctcagattg aacgctggcg gcatgcctta cacatgcaag tcgaacggca       60
gcacgggagc aatcctggtg gcgagtggcg aacgggtgag taatgtatcg gaacgtacct      120
ttcagtgggg gataacgtag cgaaagttac gctaataccg catattctgt gagcaggaaa      180 gcagggggatc gcaagacctt gcgctgattg agcggccgat atcagattag ctagttggtg      240
aggtaaaggc tcaccaaggc gacgatctgt agcgggtctg agaggatgat ccgccacact      300
ggaactgaga cacggtccag actcctacgg gaggcagcag tggggaattt tggacaatgg      360
gggcaaccct gatccagcca tgccgcgtga gtgaagaagg ccttcgggtt gtaaagctct      420
ttcggccggg aagaaatcgc atgggttaat accctgtgtg gatgacggta ccggaataag      480
aagcaccggc taactacgtg ccagcagccg cggtaatacg tagggtgcga gcgttaatcg      540
gaattactgg gcgtaaagcg tgcgcaggcg gtttagtaag acaggcgtga aatcccccggg      600 ctcaacctgg gaactgcgct tgtgactgct aagctagagt acggcagagg gggtggaat      660 tccacgtgta gcagtgaaat gcgtagagat gtggaggaac accgatgcg aaggcagccc      720 cctgggccga tactgacgct catgcacgaa agcgtgggta gcaaacagga ttagataccc      780
tggtagtcca cgccctaaac gatgtcaact aggtgttggg tggtaaaac catttagtac      840 cggagctaac gcgtgaagtt gaccgcctgg ggagtacggc cgcaaggtta aaactcaaag      900
```

-continued

| | |
|---|---:|
| gaattgacgg ggacccgcac aagcggtgga tgatgtggat taattcgatg caacgcgaaa | 960 |
| aaccttacct acccttgaca tgtccagaag cccgaagaga tttgggtgtg cccgaaaggg | 1020 |
| agctggaaca caggtgctgc atggctgtcg tcagctcgtg tcgtgagatg ttgggttaag | 1080 |
| tcccgcaacg agcgcaaccc ttgtcgttaa ttgccatcat ttagttgggc actttaacga | 1140 |
| gactgccggt gacaaaccgg aggaaggtgg ggatgacgtc aagtcctcat ggcccttatg | 1200 |
| ggtagggctt cacacgtcat acaatggtcg gtacagaggg ttgccaagcc gcgaggtgga | 1260 |
| gccaatccca gatagccgat cgtagtccgg atcgtaggct gcaactcgcc tgcgtgaagt | 1320 |
| cggaatcgct agtaatcgcg gatcagcatg tcgcggtgaa tacgttcccg ggtcttgtac | 1380 |
| acaccgcccg tcacaccatg ggagcgggtt ccgccagaag taggtagcct aaccgcaagg | 1440 |
| ggggcgctta ccacggcggg gttcgtgact ggggtgaagt cgtaacaagg tagccgtagg | 1500 |
| ggaacctgcg gctggatcac ctccc | 1525 |

<210> SEQ ID NO 45
<211> LENGTH: 1472
<212> TYPE: DNA
<213> ORGANISM: Dechloromonas anomolous

<400> SEQUENCE: 45

| | |
|---|---:|
| tttgagcctg gctcagaacg aacgctggcg gcaggcctaa cacatgcaag tcgaacgaag | 60 |
| tcttcggact tagtggcgca cgggtgagta acacgtggga atataccttg cgctggggga | 120 |
| taacatcggg aaactgatgc taataccgca tacgcccttc gggggaaaga tttatcggcg | 180 |
| aaagattagc ccgcgtccga ttagctagtt ggtgaggtaa tggctcacca aggctccgat | 240 |
| cggtagctgg tctgagagga tgaccagcca cactgggact gagacacggc ccagactcct | 300 |
| acgggaggca gcagtgggga atattggaca atgggcgcaa gcctgatcca gccatgccgc | 360 |
| gtgagtgatg aaggccttag ggttgtaaag ctctttcacc cacgacgatg atgacggtag | 420 |
| tgggagaaga agccccggct aacttcgtgc cagcagccgc ggtaatacga aggggctag | 480 |
| cgttgttcgg aattactggg cgtaaagcgc acgcaggcgg ttcggtcagt cagaagtgaa | 540 |
| agccccgggc ttaacctggg aactgctttt gatactgccg agcttgaatc acggagaggg | 600 |
| tagtggaatt ccgagtgtag aggtgaaatt cgtagatatt cggaagaaca ccagtggcga | 660 |
| aggcgactac ctggccgtcg attgacgctc atgtgcgaaa gcgtggggag caaacaggat | 720 |
| tagataccct ggtagtccac gccgtaaacg atgagtgcta gttgttgggg tgcatgcacc | 780 |
| tcagtgacgc agctaacgcg ttaagcactc cgcctgggga gtacggccgc aaggttaaaa | 840 |
| ctcaaaggaa ttgacggggg cccgcacaag cggtggagca tgtggtttaa ttcgaagcaa | 900 |
| cgcgcagaac cttaccagcc cttgacatgg gaactatggg tccagagat tggatccttc | 960 |
| acttcgggtg gttccacac aggtgctgca tggctgtcgt cagctcgtgt cgtgagatgt | 1020 |
| tgggttaagt cccgcaacga gcgcaaccct catcgtcagt tgccatcatt cagttgggca | 1080 |
| ctctgacgaa actgccggtg acaagccgga ggaaggtggg gatgacgtca agtcctcatg | 1140 |
| gcccttacgg gctgggctac acacgtgcta caatggtggt gacaatgggt cgcgagctcg | 1200 |
| cgagagttag ctaatcccca aaagccatct cagttcggat tgtactctgc aactcgagtg | 1260 |
| catgaagtcg gaatcgctag taatcgtgga tcagcatgcc acggtgaata cgttcccggg | 1320 |
| ccttgtacac accgcccgtc acaccatggg agttggcttt acccgaagcc ggtgcgctaa | 1380 |
| ccgcaaggag gcagccgacc acggtaaggt cagcgactgg ggtgaagtcg taacaaggta | 1440 |
| gccgtagggg aacctgcggc cggatcacct cc | 1472 |

<210> SEQ ID NO 46
<211> LENGTH: 1443
<212> TYPE: DNA
<213> ORGANISM: Magnetospirillum magnetotacticum

<400> SEQUENCE: 46

| | | | | | |
|---|---|---|---|---|---|
| aacgaacgct | ggcggcaggc | ttaacacatg | caagtcgaac | gaagtcttcg | gacttagtgg | 60 |
| cgcacgggtg | agtaacacgt | gggaatatac | ctcttggtgg | ggaataacgt | cgggaaactg | 120 |
| acgctaatac | cgcatacgcc | cttcggggga | aagatttatc | gccgagagat | tagcccgcgt | 180 |
| ccgattagct | agttggtgag | gtaatggctc | accaaggcga | cgatcggtag | ctggtctgag | 240 |
| aggatgatca | gccacactgg | gactgagaca | cggcccagac | tcctacggga | ggcagcagtg | 300 |
| gggaatattg | gacaatgggc | gaaagcctga | tccagccatg | ccgcgtgagt | gatgaaggcc | 360 |
| ttagggttgt | aaagctcttt | cacccacgac | gatgatgacg | gtagtgggag | aagaagcccc | 420 |
| ggctaacttc | gtgccagcag | ccgcggtaat | acgaagggg | ctagcgttgt | tcggaattac | 480 |
| tgggcgtaaa | gcgcacgcag | gcggtggtca | tagtcagaag | tgaaagccct | gggctcaacc | 540 |
| cgggaattgc | ttttgatact | ggaccgctag | aatcacggag | agggtagtgg | aattccgagt | 600 |
| gtagaggtga | aattcgtaga | tattcggaag | aacaccagtg | gcgaaggcga | ctacctggcc | 660 |
| gtcgattgac | gctcatgtgc | gaaagcgtgg | ggagcaaaca | ggattagata | ccctggtagt | 720 |
| ccacgccgta | aacgatgagt | gctagttgtt | ggggtgcatg | cacctcagtg | acgcagctaa | 780 |
| cgcgttaagc | actccgcctg | gggagtacgg | ccgcaaggtt | aaaactcaaa | ggaattgacg | 840 |
| ggggcccgca | caagcggtgg | agcatgtggt | ttaattcgaa | gcaacgcgca | gaaccttacc | 900 |
| agcccttgac | atgggacgta | tgtttgccag | agatggtgac | ttgtcttcgg | acgcgtccac | 960 |
| acaggtgctg | catggctgtc | gtcagctcgt | gtcgtgagat | gttgggttaa | gtcccgcaac | 1020 |
| gagcgcaacc | ctcatcttca | gttgccatca | tttagttggg | cactctgaag | aaactgccgg | 1080 |
| tgacaagccg | gaggaaggtg | gggatgacgt | caagtcctca | tggcccttac | gggctgggct | 1140 |
| acacacgtgc | tacaatggtg | gtgacagtgg | gtcgctaact | cgcgagagta | tgctaatccc | 1200 |
| taaaagccat | ctcagttcgg | attgcactct | gcaactcgag | tgcatgaagt | cggaatcgct | 1260 |
| agtaatcgtg | gatcagcatg | ccacggtgaa | tacgttcccg | ggccttgtac | acaccgcccg | 1320 |
| tcacaccatg | ggagttggct | ttacccgaag | ccggtgcgct | aaccgcaagg | aggcagccga | 1380 |
| ccacggtaag | gtcagcgact | ggggtgaagt | cgtaacaagg | tagccgtagg | ggaacctgcg | 1440 |
| gct | | | | | | 1443 |

<210> SEQ ID NO 47
<211> LENGTH: 1467
<212> TYPE: DNA
<213> ORGANISM: Pseudomonas sp.

<400> SEQUENCE: 47

| | | | | | |
|---|---|---|---|---|---|
| atgaagaggg | cttgctctct | gattcagcgg | cggacgggtg | agtaatgcct | aggaatctgc | 60 |
| ctgatagtgg | gggacaacgt | ttcgaaagga | acgctaatac | cgcatacgtc | ctacgggaga | 120 |
| aagcagggga | ccttcgggcc | ttgcgctatc | agatgagcct | aggtcggatt | agctagttgg | 180 |
| tgaggtaacg | gctcaccaag | gcgacgatcc | gtaactggtc | tgagaggatg | atcagtcaca | 240 |
| ctggaactga | gacacggtcc | agactcctac | gggaggcagc | agtggggaat | attggacaat | 300 |
| gggcgaaagc | ctgatccagc | catgccgcgt | gtgtgaagaa | ggtcttcgga | ttgtaaagca | 360 |
| ctttaagttg | ggaggaaggg | cattaaccta | atacgttagt | gttttgacgt | taccgacaga | 420 |

```
ataagcaccg gctaacttcg tgccagcagc cgcggtaata cgaagggtgc aagcgttaat    480
cggaattact gggcgtaaag cgcgcgtagg tggtttgtta agttgaatgt gaaagccccg    540
ggctcaacct gggaactgca tccaaaactg gcaagctaga gtatggcaga gggtggtgga    600
atttcctgtg tagcggtgaa atgcgtagat ataggaagga acaccagtgg cgaaggcgac    660
cacctgggct aatactgaca ctgaggtgcg aaagcgtggg gagcaaacag gattagatac    720
cctggtagtc cacgccgtaa acgatgtcga ctagccgttg gatccttga gatcttagtg     780 gcgcagctaa cgcattaagt cgaccgcctg gggagtacgg ccgctaggtt aaaactctaa    840
tgaattgacg gggcccgca caagcggtgg agcatgtggt ttaattcgaa gcaacgcgaa     900
gaaccttacc aggccttgac atgcagagaa ctttccagag atggattggt gccttcggga    960
actctgacac aggtgctgca tggctgtcgt cagctcgtgt cgtgagatgt tgggttaagt   1020
cccgtaacga gcgcaaccct tgtccttagt taccagcacg ttaaggtggg cactctaagg   1080
agactgccgg tgacaaaccg gaggaaggtg gggatgacgt caagtcatca tggcccttac   1140
ggcctgggct acacacgtgc tacaatggtc ggtacaaagg gttgccaagc cgcgaggtgg   1200
agctaatccc ataaaaccga tcgtagtccg gatcgcagtc tgcaactcga ctgcgtgaag   1260
tcggaatcgc tagtaatcgt gaatcagaat gtcacggtga atacgttccc gggccttgta   1320
cacaccgccc gtcacaccat gggagtgggt tgctccagaa gtagctagtc taaccttcgg   1380
ggggacggtt accacggagg tattcatgac tggggtgaag tcgtaacaag gtagccgtag   1440
gggaacctgc ggctggatca cctcctt                                       1467

<210> SEQ ID NO 48
<211> LENGTH: 1456
<212> TYPE: DNA
<213> ORGANISM: Pseudomonas stutzeri

<400> SEQUENCE: 48
gaacgctggc ggcaggccta acacatgcaa gtcgagcgga tgaagagagc ttgctctctg     60
attcagcggc ggacgggtga gtaatgccta ggaatctgcc tgatagtggg ggacaacgtt    120
tcgaaaggaa cgctaatacc gcatacgtcc tacgggagaa agcagggac cttcgggcct     180 tgcgctatca gatgagccta ggtcggatta gctagttggt gaggtaacgg ctcaccaagg    240
cgacgatccg taactggtct gagaggatga tcagtcacac tggaactgag acacggtcca    300
gactcctacg ggaggcagca gtggggaata ttggacaatg ggcgaaagcc tgatccagcc    360
atgccgcgtg tgtgaagaag gtcttcggat tgtaaagcac tttaagttgg gaggaagggc    420
attaacctaa tacgttagtg ttttgacgtt accgacagaa taagcaccgg ctaacttcgt    480
gccagcagcc gcggtaatac gaagggtgca agcgttaatc ggaattactg ggcgtaaagc    540
gcgcgtaggt ggtttgttaa gttgaatgtg aaagccccgg ctcaacctg gaactgcat     600 ccaaaactgg caagctagag tatggcagag ggtggtggaa tttcctgtgt agcggtgaaa    660
tgcgtagata taggaaggaa caccagtggc gaaggcgacc acctgggcta atactgacac    720
tgaggtgcga aagcgtgggg agcaaacagg attagatacc ctggtagtcc acgccgtaaa    780
cgatgtcgac tagccgttgg atccttgag atcttagtgg cgcagctaac gcattaagtc     840
gaccgcctgg ggagtacggc cgcaaggtta aaactcaaat gaattgacgg ggcccgcac    900 aagcggtgga gcatgtggtt taattcgaag caacgcgaag aaccttacca ggccttgaca    960
tgcagagaac tttccagaga tggattgtg ccttcgggaa ctctgacaca ggtgctgcat    1020
ggctgtcgtc agctcgtgtc gtgagatgtt gggttaagtc ccgtaacgag cgcaacccctt   1080
```

```
gtccttagtt accagcacgt taaggtgggc actctaagga gactgccggt gacaaaccgg      1140
aggaaggtgg ggatgacgtc aagtcatcat ggcccttacg gcctgggcta cacacgtgct      1200
acaatggtcg gtacaaaggg ttgccaagcc gcgaggtgga gctaatccca taaaaccgat      1260
cgtagtccgg atcgcagtct gcaactcgac tgcgtgaagt cggaatcgct agtaatcgtg      1320
aatcagaatg tcacggtgaa tacgttcccg ggccttgtac acaccgcccg tcacaccatg      1380
ggagtgggtt gctccagaag tagctagtct aaccttcggg gggacggtta ccacggagtg      1440
attcatgact ggggtg                                                     1456
```

<210> SEQ ID NO 49
<211> LENGTH: 1501
<212> TYPE: DNA
<213> ORGANISM: Dechloromarinus chlorophilus

<400> SEQUENCE: 49

```
gagtttgatc ctggctcaga ttgaacgctg gcggtatgct taacacatgc aagtcgaacg        60
gcagcacgag agagcttgct ctcttggtgg cgagtggcgg acgggtgagt aacgcgtaag       120
aatctgcctg gtagtggggg ataactcggg gaaactcgag ctaataccgc atacgccctac      180 cggggggaaag tggggaccct tcgggcctca cgctattaga tgagcttgcg ttggattagc      240
tagttggtag ggtaatggcc taccaaggcg acgatccata gctggtctga gaggacgatc      300
agccacactg ggactgagac acggcccaga ctcctacggg aggcagcagt ggggaatatt      360
ggacaatggg cgcaagcctg atccagcaat accgcgtgtg tgaagaaggc ctgcgggttg      420
taaagcactt tcaattgtga agaaaagctt ggggctaata tcctcgagtc ttgacgttaa      480
ctttagaaga agcaccggct aactctgtgc cagcagccgc ggtaatacag agggtgcgag      540
cgttaatcgg aattactggg cgtaaagcgt gcgtaggcgg tttagtaagt cagatgtgaa      600
agccctgggc ttaacctggg aactgcattt gaaactgctg aactagagtg tggtagaggg      660
aagtggaatt ccgggtgtag cggtgaaatg cgtagatatc cggaggaaca ccagtggcga      720
aggcgacttc ctggaccaac actgacgctg aggtacgaaa gcgtgggtag caaacaggat      780
tagataccct ggtagtccac gccgtaaacg atgtcaacta gttgttggga gcattttggc      840
ttttagtaac gtagctaacg cgataagttg accgcctggg gagtacggcc gcaaggttaa      900
aactcaaagg aattgacggg ggcccgcaca agcggtggag catgtggttt aattcgatgc      960
aacgcgaaga accttaccag cccttgacat cctgcgaact ttctagagat agattggtgc     1020
tttcgggaac gcagtgacag gtgctgcatg gctgtcgtca gctcgtgtcg tgagatgttg     1080
ggttaagtcc cgtaacgagc gcaacccttg tccttagttg ccagcatttc gggatgggaa     1140
ctctagggag actgccggtg ataaaccgga ggaaggtggg gatgacgtca agtcatcatg     1200
gcccttatgg gctgggctac acacgtgcta caatggccgg tacagagggc gcaaacccg      1260 cgaggggag caaatctcac aaaaccggtc gtagtccgga tcgcagtctg caactcgact     1320
gcgtgaagtt ggaatcgcta gtaatcgcga atcagaatgt cgcggtgaat acgttcccgg     1380
gccttgtaca caccgcccgt cacaccatgg gagtgggttg caaagaagt aggtagtcta     1440 accttcggga ggacgcttac cactttgtga ttcatgactg ggtgaagtc gtaacaaggt     1500 a                                                                    1501
```

<210> SEQ ID NO 50
<211> LENGTH: 1532
<212> TYPE: DNA
<213> ORGANISM: Azospira suillum

<400> SEQUENCE: 50

```
agagtttgat cctggctcag attgaacgct ggcggcatgc cttacacatg caagtcgaac      60
ggcagcacgg gagcttgctc ctggtggcga gtggcgaacg ggtgagtaat acatcggaac     120
gtacccagga gtgggggata acgtagcgaa agttacgcta ataccgcata ttctgtgagc     180
aggaaagcgg gggatcgcaa gacctcgcgc tcttggagcg gccgatgtcg gattagctag     240
ttggtgaggt aaaagctcac caaggcgacg atccgtagcg gtctgagag  gatgatctgc     300
cacactggga ctgagacacg gcccagactc ctacgggagg cagcagtggg gaattttgga     360
caatggggggc aaccctgatc cagccatgcc gcgtgagtga agaaggcctt cgggttgtaa     420
agctctttcg gcggggaaga atggcaacg  gctaatatcc gttgttgatg acggtacccg     480
cataagaagc accggctaac tacgtgccag cagccgcggt aatacgtagg gtgcgagcgt     540
taatcggaat tactgggcgt aaagcgtgcg caggcggttt cgtaagacag acgtgaaatc     600
cccgggctca acctgggaac tgcgtttgtg actgcgaggc tagagtacgg cagagggggg     660
tagaattcca cgtgtagcag tgaaatgcgt agagatgtgg aggaataccg atggcgaagg     720
cagcccctg  ggttagtact gacgctcatg cacgaaagcg tggggagcaa acaggattag     780
ataccctcgt agtccacgcc ctaaacgatg tcaactaggt gttggaaggg ttaaaccttt     840
tagtaccgca gctaacgcgt gaagttaccc gcctggggag tacggccgca aggttaaaac     900
tcaaaggaat tgacggggac cgcacaagc  ggtggatgat gtggattaat tcgatgcaac     960
gcgaaaaacc ttacctaccc ttgacatgcc aggaactttc cagagatgga ttggtgcccg    1020
aaagggagcc tggacacagg tgctgcatgg ctgtcgtcag ctcgtgtcgt gagatgttgg    1080
gttaagtccc gcaacgagcg caacccttgt cattaattgc catcattcag ttgggcactt    1140
taatgagact gccggtgaca aaccggagga aggtgggat  gacgtcaagt cctcatggcc    1200
cttatgggta gggcttcaca cgtcatacaa tggtcggtac agagggttgc caagccgcga    1260
ggtggagcca atcccagaaa gccgatcgta gtccggatcg cagtctgcaa ctcgactgcg    1320
tgaagtcgga atcgctagta atcgcggatc agcatgtcgc ggtgaatacg ttcccgggtc    1380
ttgtacacac cgcccgtcac accatgggag tgggttctac cagaagtagt tagcctaacc    1440
gtaaggaggg cgattaccac ggtaggattc atgactgggg tgaagtcgta acaaggtagc    1500
cgtatcggaa ggtgcggctg gatcacctcc tt                                  1532
```

<210> SEQ ID NO 51
<211> LENGTH: 1523
<212> TYPE: DNA
<213> ORGANISM: Dechloromonas sp.

<400> SEQUENCE: 51

```
gtttgatcct cgctcagatt gaacgctggc ggcatgcctt acacatgcaa gtcgaacggc      60
agcacggact tcggtctggt ggcgagtggc gaacgggtga gtaatgcatc ggaacgtacc     120
cggaagtggg ggataactat ccgaaaggat ggctaatacc gcatattctg tacgcaggaa     180
agagggggat cttcggacct cttgctttcg gagcggccga tgtcagatta gctagttggt     240
ggggtaaagg cctaccaagg cgacgatctg tagcgggtct gagaggatga tccgccacac     300
tggaactgag acacggtcca gactcctacg ggaggcagca gtgggaatt  tttggacaatg     360
ggcgcaagcc tgatccagcc atgccgcgtg agtgaagaag gccttcgggt tgtaaagctc     420
tttcggccgg gaaaaatcg  gtgaggctaa tatcctcatc ggatgatggt accgggactaa     480
gaagcaccgg ctaactacgt gccagcagcc gcggtaatac gtagggtgcg agcgttaatc     540
```

-continued

```
ggaattactg gcgtaaagc gtgcgcaggc ggttttttaa gacaggcgtg aaatccccgg      600
gcttaacctg ggaactgcgt ttgtgactgg aaggctagat tacggcagag ggggtggaa      660 ttccacgtgt agcagtgaaa tgcgtagaga tgtggaggaa caccaatggc gaaggcagcc      720
ccctgggtcg atactgacgc tcatgcacga aagcgtgggg agcaaacagg attagatacc      780
ctggtagtcc acgccctaaa cgatgtcaac taggtgttgg gtgggtaaaa ccatttagta      840
ccggagctaa cgcgtgaagt tgaccgcctg ggagtacgg ccgcaaggtt aaaactcaaa       900
ggaattgacg ggacccgca caagcggtgg atgatgtgga ttaattcgat gcaacgcgaa       960
aaaccttacc taccccttgac atgccaggaa cttgccagag atggcttggt gcccgaaagg    1020
gagcctggac acaggtgctg catggctgtc gtcagctcgt gtcgtgagat gttgggttaa    1080
gtcccgcaac gagcgcaacc cttgtcgtta attgccatca ttaagttggg cactttaacg    1140
agactgccgg tgacaaaccg gaggaaggtg gggatgacgt caagtcctca tggcccttat    1200
gggtagggct tcacacgtca tacaatggtc ggtacagagg gttgccaagc cgcgaggtgg    1260
agccaatccc agaaagccga tcgtagtccg gatcgtaggc tgcaactcgc ctgcgtgaag    1320
tcggaatcgc tagtaatcgc ggatcagcat gtcgcggtga atacgttccc gggtcttgta    1380
cacaccgccc gtcacaccat gggagcgggt ccgccagaa gtaggtagcc taaccgcaag    1440
gggggcgctt accacggcgg ggttcgtgac tggggtgaag tcgtaacaag gtagccgtag    1500
gggaacctgc ggctggatca cct                                            1523
```

<210> SEQ ID NO 52
<211> LENGTH: 1500
<212> TYPE: DNA
<213> ORGANISM: Ideonella dechloratans

<400> SEQUENCE: 52

```
attgaacgct ggcggcatgc cttacacatg caagtcgaac ggtaagcggg caacctggcg       60
acgagtggcg aacgggtgag taatgcatcg gaacgtgccc agtagtgggg gatagcccgg      120
cgaaagccgg attaataccg catacgacct gagggtgaaa ggggggggatc gcaagacctc     180 tcgctattgg agcggccgat gtcagattag gtagttggtg gggtaaaggc ctaccaagcc     240
gacgatctgt agctggtctg agaggacgac cagccacact gggactgaga cacgccccag     300
actcctacgg gaggcagcag tggggaattt tggacaatgg gcgcaagcyt gatccagcca     360
tgccgcgtgc ggaagaaggc cttcggttg taaaccgctt ttgtcaggga agaaatcttc     420
tgggctaata cctcgggagg atgacggtac ctgaagaata gcaccggct aactacgtgc      480 cagcagccgc ggtaatacgt agggtgcaag cgttaatcgg aattactggg cgtaaagcgt     540 gcgcaggcg ttttgtaaga cagaggtgaa atccccgggc tcaacctggg aactgccttt     600
gtgactgcaa ggcttgagtg cgcagagggg gatggaattc gcgtgtagc agtgaaatgc      660 gtagatatgc ggaggaacac cgatggcgaa ggcaatcccc tgggcctgca ctgacgctca    720
tgcacgaaag cgtggggagc aaacaggatt agatacctg gtagtccacg ccctaaacga     780
tgtcaactgg ttgttgggaa ggttccttct cagtaacgta gctaacgcgt gaagttgacc    840
gcctggggag tacggccgca aggttgaaac tcaaggaat tgacgggac ccgcacaagc      900 ggtggatgat gtggtttaat tcgatgcaac gcgaaaaacc ttacctaccc ttgacatggc    960
aggaatcctg aagagatttg ggagtgctcg aaagagaacc tgcacacagg tgctgcatgg   1020
ccgtcgtcag ctcgtgtcgt gagatgttgg gttaagtccc gcaacgagcg caacccttgt   1080
cattagttgc tacgaaaggg cactctaatg agactgccgg tgacaaaccg gaggaaggtg   1140
```

```
gggatgacgt caggtcctca tggcccttat gggtagggct acacacgtca tacaatggcc    1200
ggtacagagg gctgccaayc cgcgaggggg agccaatccc agaaaaccgg tcgtagtccg    1260
gatcgcagtc tgcaactcga ctgcgtgaag tcggaatcgc tagtaatcgc ggatcagctt    1320
gccgcggtga atacgttccc gggtcttgta cacaccgccc gtcacaccat gggagcgggt    1380
tctgccagaa gtagttagcc taaccgcaag gagggcgatt accacggcag ggttcgtgac    1440
tggggtgaag tcgtaacaag gtagccgtat cggaaggtgc ggctggatca cctcctttct    1500
```

<210> SEQ ID NO 53
<211> LENGTH: 20
<212> TYPE: PRT
<213> ORGANISM: Dechloromonas agitata

<400> SEQUENCE: 53

Met Ala Arg Leu Ser Arg Arg Asp Phe Leu Lys Ala Ser Ala Ala Thr
1               5                   10                  15

Leu Leu Gly Asn
            20

<210> SEQ ID NO 54
<211> LENGTH: 20
<212> TYPE: PRT
<213> ORGANISM: Dechloromonas aromatica

<400> SEQUENCE: 54

Met Val Gln Met Thr Arg Arg Gly Phe Leu Leu Ala Ser Gly Ala Thr
1               5                   10                  15

Leu Leu Gly Ser
            20

<210> SEQ ID NO 55
<211> LENGTH: 18
<212> TYPE: PRT
<213> ORGANISM: Dechloromonas sp. strain GR1
<220> FEATURE:
<221> NAME/KEY: misc_feature
<222> LOCATION: (17)..(17)
<223> OTHER INFORMATION: Xaa can be any naturally occurring amino acid

<400> SEQUENCE: 55

Ala Asn Val Met Lys Ala Pro Arg Arg Gln Leu Thr Tyr Val Thr Asp
1               5                   10                  15

Xaa Asn

<210> SEQ ID NO 56
<211> LENGTH: 333
<212> TYPE: PRT
<213> ORGANISM: Dechloromonas aromatica

<400> SEQUENCE: 56

Met Ala Asn Val Met Lys Ala Pro Lys Arg Gln Leu Thr Tyr Val Thr
1               5                   10                  15

Asp Leu Asn Lys Cys Ile Gly Cys Gln Thr Cys Thr Val Ala Cys Lys
                20                  25                  30

Lys Leu Trp Thr Thr Gly Pro Gly Gln Asp Phe Met Tyr Trp Arg Asn
            35                  40                  45

Val Glu Thr Thr Pro Gly Leu Gly Tyr Pro Arg Asn Trp Gln Thr Lys
        50                  55                  60

Gly Gly Gly Tyr Lys Asn Gly Glu Leu Gln Lys Gly Lys Ile Pro Pro
65                  70                  75                  80

```
Met Ile Asp Tyr Gly Ile Pro Phe Glu Phe Asp Tyr Ala Gly Arg Leu
             85                  90                  95

Phe Glu Gly Lys Lys Glu Arg Val Arg Pro Ser Pro Thr Pro Arg Ser
            100                 105                 110

Ala Pro Asn Trp Asp Glu Asp Gln Gly Ala Gly Glu Tyr Pro Asn Asn
            115                 120                 125

Ser Phe Phe Tyr Leu Pro Arg Met Cys Asn His Cys Tyr Lys Pro Ala
            130                 135                 140

Cys Leu Glu Ala Cys Pro Asn Glu Ala Ile Tyr Lys Arg Glu Gln Asp
145                 150                 155                 160

Gly Ile Val Val Ile His Gln Asp Lys Cys Lys Gly Ala Gln Ala Cys
                165                 170                 175

Val Gln Ser Cys Pro Tyr Ala Lys Pro Tyr Phe Asn Pro Val Ala Asn
            180                 185                 190

Lys Ala Asn Lys Cys Ile Gly Cys Phe Pro Arg Ile Glu Gln Gly Val
            195                 200                 205

Ala Pro Cys Cys Val Ala Gln Cys Val Gly Arg Ala Met His Val Gly
            210                 215                 220

Phe Ile Asp Asp Thr Asn Ser Ser Val His Lys Leu Ile Arg Leu Tyr
225                 230                 235                 240

Lys Val Ala Leu Pro Leu His Pro Glu Phe Gly Thr Glu Pro Asn Val
                245                 250                 255

Phe Tyr Val Pro Pro Val Leu Gly Pro Arg Met Glu Leu Pro Asn Gly
            260                 265                 270

Glu Leu Ser Thr Asp Pro Lys Ile Pro Leu Ala Gln Leu Glu Gly Leu
            275                 280                 285

Phe Gly Lys Gln Val Arg Asp Val Leu Ala Ile Leu Gln Thr Glu Arg
            290                 295                 300

Glu Lys Lys Met Lys Gly Leu Ala Ser Asp Leu Met Asp Val Leu Ile
305                 310                 315                 320

Gly Arg Arg Ser Ala Asp Met Met Ile Ser Pro Leu Thr
                325                 330

<210> SEQ ID NO 57
<211> LENGTH: 236
<212> TYPE: PRT
<213> ORGANISM: Dechloromonas aromatica

<400> SEQUENCE: 57

Met Ile Lys Ile Leu Ala Leu Ala Thr Leu Leu Ile Ser Gly Phe Leu
1               5                   10                  15

Pro Gly Val Thr Val Ala Gln Gln Ala Glu Tyr Leu Gly Phe Arg Ala
             20                  25                  30

Cys Thr Lys Cys His Asp Ser Gln Gly Glu Thr Trp Arg Ala Ser Ala
             35                  40                  45

His Ala Lys Ala Phe Asp Ser Leu Lys Pro Asn Ala Lys Ser Glu Ala
             50                  55                  60

Lys Thr Lys Ala Lys Leu Asp Pro Lys Asp Tyr Thr Gln Asp Lys
65                  70                  75                  80

Asn Cys Val Gly Cys His Val Thr Gly Tyr Gly Glu Pro Gly Gly Pro
             85                  90                  95

Val Ser Gly Ala Ser Leu Asp Asp Met Lys Thr Leu Val Gly Val Thr
            100                 105                 110

Cys Asx Ser Cys His Gly Ala Gly Gly Lys Phe Arg Asn Leu His Gly
            115                 120                 125
```

-continued

```
Glu Ala Ser Asp Arg Leu Lys Asn Gln Gly Glu Thr Ser Glu Arg Lys
    130                 135                 140

Gln Leu Val Thr Ala Gly Gln Asn Phe Asp Met Glu Lys Ala Cys Ala
145                 150                 155                 160

Arg Cys His Leu Asn Phe Glu Gly Ser Thr Lys His Asp Ala Lys Ala
                165                 170                 175

Pro Phe Thr Pro Phe Ser Pro Ser Val Gly Ser Lys Tyr Gln Phe Asp
            180                 185                 190

Phe Gln Lys Ser Val Met Thr Thr Gly Ala Gly Asn Pro Ile His Thr
        195                 200                 205

His Phe Lys Leu Arg Gly Val Pro Lys Gly Asp Pro Val Pro Ala Val
    210                 215                 220

Arg Ala Lys Leu Gln Glu Asp Ala Pro Glu Pro Glu
225                 230                 235
```